United States Patent
Kumar et al.

(10) Patent No.: US 9,313,332 B1
(45) Date of Patent: Apr. 12, 2016

(54) ROUTING USER COMMUNICATIONS TO AGENTS

(71) Applicant: Angel.com Incorporated, Vienna, VA (US)

(72) Inventors: Praphul Kumar, Daly City, CA (US); Aaron Wellman, Annandale, VA (US); Ahmed Tewfik Bouzid, McLean, VA (US)

(73) Assignee: ANGEL.COM INCORPORATED, Vienna, VA (US)

( * ) Notice: Subject to any disclaimer, the term of this patent is extended or adjusted under 35 U.S.C. 154(b) by 0 days.

(21) Appl. No.: 14/051,901

(22) Filed: Oct. 11, 2013

Related U.S. Application Data

(60) Provisional application No. 61/730,671, filed on Nov. 28, 2012, provisional application No. 61/730,679, filed on Nov. 28, 2012.

(51) Int. Cl.
*H04M 3/00* (2006.01)
*H04M 3/523* (2006.01)

(52) U.S. Cl.
CPC .................................. *H04M 3/5232* (2013.01)

(58) Field of Classification Search
CPC . H04M 3/51; H04M 3/5175; H04M 2201/40; H04M 1/271; H04M 3/493
USPC .......................................... 379/88.01, 265.07
See application file for complete search history.

(56) References Cited

U.S. PATENT DOCUMENTS

| | | | | |
|---|---|---|---|---|
| 8,787,534 B1* | 7/2014 | Witt-Ehsani | ........ | H04M 3/5166 379/265.01 |
| 2005/0238161 A1* | 10/2005 | Yacoub | ............... | H04M 3/5166 379/265.06 |
| 2012/0051536 A1* | 3/2012 | Chishti | ............... | H04M 3/5175 379/265.06 |

* cited by examiner

*Primary Examiner* — Van D Huynh
(74) *Attorney, Agent, or Firm* — Lewis Roca Rothgerber Christie LLP

(57) ABSTRACT

A call handling platform receives a call placed by a caller to a calling number and computes an experience score for the caller based on measuring a subset of data points corresponding to an interaction between the caller and an interactive voice response (IVR) module. The experience score provides a numerical measure of a level of satisfaction of the caller in interacting with the IVR module during the call. Determining to route the call to a human agent based on the experience score, the call handling platform accesses historical data corresponding to past calls placed by the caller and received by human agents, and obtains agent scores associated with the human agents. The call handling platform matches the caller to a human agent at a call center based on one or both of the historical data and the agent scores, and routes the call to the human agent.

18 Claims, 20 Drawing Sheets

ROUTING USER COMMUNICATIONS TO AGENTS

CROSS-REFERENCE TO RELATED APPLICATIONS

This application claims priority from U.S. Provisional Application No. 61/730,671, filed Nov. 28, 2012, and titled UNIFIED PHONE AND WEB LEAD TRACKING and U.S. Provisional Application No. 61/730,679, filed Nov. 28, 2012, and titled SECURE ORDERING OF MEDICAL SAMPLES USING MOBILE DEVICES. Both of these prior applications are incorporated by reference in their entirety.

TECHNICAL FIELD

This disclosure relates to routing user communications to human agents.

BACKGROUND

A user may use a personal communications device to contact a company to discuss a service or a product provided by the company. The user may contact the company by establishing electronic communications with the company through use of one or more of multiple different communications modes (e.g., phone, email, web chat, or Short Message Service (SMS) that support communications).

SUMMARY

In a general aspect, a call handling platform receives a first call placed by a first caller to a first calling number. The call handling platform computes a first experience score for the first caller based on measuring a first subset of data points corresponding to an interaction between the first caller and an interactive voice response (IVR) module associated with the call handling platform, wherein the first experience score provides a numerical measure of a level of satisfaction of the first caller in interacting with the IVR module during the first call. The call handling platform determines to route the first call to a human agent based on the first experience score.

In response to determining to route the first call to a human agent, the call handling platform accesses historical data corresponding to past calls placed by the first caller and received by human agents. The historical data includes information on interactions between the first caller and the human agents during the past calls. The call handling platform obtains agent scores associated with the human agents, wherein the agent scores provide information on a level of performance skills associated with the human agents in interacting with callers. The call handling platform matches the first caller to a first human agent at a first call center based on one or both of the historical data and the agent scores. The call handling platform routes the first call to the first human agent at the first call center.

Particular implementations may include one or more of the following features. A first customer of the call handling platform that is associated with the first calling number is enabled to select the first subset of data points from a group of data points available at the call handling platform. The first customer of the call handling platform is enabled to configure values for the first subset of data points. Enabling the first customer of the call handling platform to configure the values for the first subset of data points may include enabling the first customer to use an Internet-based browser user interface associated with the call handling platform to configure the values for the first subset of data points.

The first subset of data points may be selected from the group consisting of: a number of no inputs by a caller placing a call to the call handling platform, wherein each no input corresponds to an instance of failure of the caller to respond to a query by the call handling platform, a number of no matches by a caller placing a call to the call handling platform, wherein each no match corresponds to an instance of the caller providing a response to a query by the call handling platform that does not match a pre-determined response expected by the call handling platform, a number of tasks not completed by a caller placing a call to the call handling platform, wherein each task not completed indicates an instance of the caller failing to complete successfully a task that has been requested by the call handling platform, a number of zero actions by a caller placing a call to the call handling platform, wherein each zero action corresponds to an instance of the caller providing a preconfigured input indicating an attempt to connect to a human agent irrespective of a query by the call handling platform, a time to zero out by a caller placing a call to the call handling platform, wherein the time to zero out indicates how quickly the caller attempts to talk to a human agent after the call is connected, and a wait time of a caller placing a call to the call handling platform, wherein the wait time of the caller indicates how long the caller has to wait before being connected to a human agent.

Determining to route the first call to a human agent based on the first experience score may include accessing a predetermined first threshold that indicates a minimum level of caller satisfaction, wherein the first threshold is configured by a first customer of the call handling platform that is associated with the first calling number. The first experience score may be compared to the first threshold. The call handling platform may determine, based on the comparing, that the first experience score for the first caller indicates that the first caller has a lower level of satisfaction than the minimum level of satisfaction. The first call may be routed to the human agent conditioned on determining that the first experience score for the first caller indicates that the first caller has a lower level of satisfaction than the minimum level of satisfaction.

Obtaining the agent scores associated with the human agents may include the call handling platform measuring a first subset of agent skills that are configured by a first customer of the call handling platform that is associated with the first calling number. The call handling platform may compute an agent score for each human agent trained to answer the first call as a numerical score based on the measuring the first subset of the agent skills.

Measuring the first subset of agent skills may include measuring, by the call handling platform the first subset of agent skills using speech analytics. The first subset of agent skills may be selected from the group consisting of: courtesy of a human agent in interacting with a caller, which indicates how politely an agent speaks while interacting with a caller, skill of a human agent in calming an agitated caller, which indicates how well an agent is able to soothe an agitated caller while interacting with the caller, skill of a human agent in up-selling products to caller, which indicates whether an agent successfully sells a product or service to a caller while interacting with the caller, skill of a human agent in providing explanations to a caller, which indicates how well an agent is able to answer questions from a caller while interacting with the caller and clarity of speech in interacting with a caller which indicates how clearly an agent speaks while interacting with a caller.

Accessing the historical data corresponding to past calls placed by the first caller may include the call handling platform determining a subject matter of the first call. The call handling platform may identify human agents who are trained to handle calls corresponding to the determined subject matter. The call handling platform may determine whether the first caller had interacted with each of the identified human agents in the past. The call handling platform may obtain historical data of interactions between the first caller and the identified human agents with whom the first caller had interacted in the past. The historical data may include second experience scores for the first caller. Each of the second experience scores may be specific to one of the identified human agents with whom the first caller had previously interacted and reflecting an estimated level of satisfaction of the first caller with past interactions with the corresponding one of the identified human agents.

A first customer of the call handling platform that is associated with the first calling number may be enabled to configure one or more predetermined keywords. The second experience scores may be generated using a speech analysis module that is operable to detect the one or more predetermined keywords in voice speech made by the first caller or a human agent during a call.

Matching the first caller to a first human agent at a first call center may include identifying the first human agent based on the call handling platform determining that a second experience score indicating that a level of satisfaction of the first caller regarding past interactions with the first human agent is greater than that of the first caller regarding past interactions with other of the identified human agents with whom the first caller had interacted in the past.

The call handling platform may determine that the first human agent is not available to answer the first call based on the first human agent not answering the first call within a predetermined wait period. A second human agent at a second call center may be identified based on identification of a second experience score that indicates that a level of satisfaction of the first caller with past interactions with the second human agent is less than that of the first caller with past interactions with the first human agent but is greater than that of the first caller with past interactions with the remaining identified human agents with whom the first caller had interacted in the past. Based on determining that the first human agent is not available to answer the first call, the call handling platform may route the first call to the identified second human agent at the second call center.

Matching the first caller to a first human agent at a first call center may include the call handling platform determining that no suitable human agent is available based on the historical data corresponding to calls placed by the first caller. In response to determining that no suitable human agent is available based on the historical data, a human agent having an agent score deemed most compatible with the first call from among the obtained agent scores may be identified as the first human agent.

The historical data may include demographic information associated with the first caller. Matching the first caller to a first human agent at a first call center may include the call handling platform identifying, as the first human agent, a human agent who is trained to handle calls from callers with demographic information matching the demographic information associated with the first caller.

The historical data may include a speech accent associated with the first caller. Matching the first caller to a first human agent at a first call center may include the call handling platform identifying, as the first human agent, a human agent who is trained to handle calls from callers with speech accents matching the speech accent associated with the first caller.

In another general aspect, a functionality is included in a webpage of a website which, when selected, initiates a telephone communication session. An interaction of a user with the website is analyzed. The interaction includes a selection of the functionality. An interest of the user in the website is categorized based on the interaction.

Particular implementations may include one or more of the following features. Analyzing the interaction may include determining a web context that resulted in selection of the functionality to initiate the telephone communication. Categorizing the interest of the user in the website may include categorizing the interest of the user based on the web context and based on information about the telephone communication session.

The web context may include an identity of the user captured by the website. The web context may include a browsing history of the user on the website. The web context may include documents downloaded from the website by the user. The web context may include interactions with the user in a chat session provided through the website. The web context may include the webpage with which the user was interacting upon selection of the function to initiate the telephone communication session.

The information about the telephone communication session may include a duration of the telephone communication session. The information about the telephone communication session may include interactive voice response selections made by the user during the telephone communication session. The information about the telephone communication session may include an identity of a call agent that handled the telephone communication session.

Categorizing the interest of the user based on the interaction may include categorizing a level of interest of the user in a product or a service offered by or through the website based on the interaction. Categorizing the level of interest of the user in the product or service may include categorizing the level of interest in real time upon the user selecting the function to initiate the telephone communication session such that the level of interest is available in real time for controlling handling of the telephone communication session. The level of interest may be selected from among a set of predetermined levels that include a first level representing a relatively low interest, a second level representing a relatively intermediate interest, and a third level representing a relatively high interest.

In another general aspect, a computer-readable medium tangibly stores a computer software program executable by data processing apparatus to perform operations that include tracking an interaction between a user and a website. The interaction includes a selection of a selectable functionality on a webpage of the website that initiates a telephone communication when selected. The user is categorized based on the interaction.

In another general aspect, input is received through a mobile device to procure medical samples. The input includes a voice sample of a user attempting to procure the medical samples. The voice sample of the user is analyzed to determine whether the received voice sample matches a voice sample previously received from an authorized user. A determination is made whether the voice sample was received from the authorized user based on the analyzing. If the voice sample is determined to have been received from the authorized user, the user is enabled to conduct a transaction using the mobile device to procure the medical samples.

In another general aspect, input is received through a mobile device to order medical samples. The input includes a voice sample of a user attempting to order the medical samples, location data indicating a physical location of the mobile device, and user login information. The voice sample of the user is analyzed to determine whether the received voice sample matches a voice sample previously received from an authorized user. The location data is analyzed to determine whether the received location data matches a location previously identified by the authorized user as being an authorized location from which to submit an order for medical samples. A determination is made whether the voice sample was received from the authorized user based on the analyzing of the voice sample. A determination is made, based on the analyzing of the location data, whether the location data matches a location previously identified by the authorized user as being an authorized location from which to submit an order for medical samples. If the voice sample is determined to have been received from the authorized user and if the location data matches a location previously identified by the authorized user as being an authorized location, a communication is sent to a user identity corresponding to the authorized user that informs the authorized user of the order and requests that the authorized user confirms the order. A response communication is received from the user identity corresponding to the authorized user. If the response communication indicates that the order is confirmed, the order of medical samples is communicated to a source of medical samples.

Implementations of the above techniques include methods, systems and computer program products. One such system comprises a call handling platform that includes a first processor and first instructions stored in a machine-readable medium that, when executed by the first processor, are operable to perform one or more of the above described actions. The system also comprises an IVR module, which includes second instructions stored in a machine-readable storage medium that, when executed by a second processor, are configured to cause the second processor to perform one or more of the above described actions.

One such computer program product is suitably embodied in a non-transitory machine-readable medium and includes instructions executable by one or more processors. The instructions are configured to cause the one or more processors to perform the above described actions.

The details of one or more disclosed implementations are set forth in the accompanying drawings and the description below. Other features, aspects, and advantages will become apparent from the description, the drawings and the claims.

DETAILED DESCRIPTION

Figure 1:
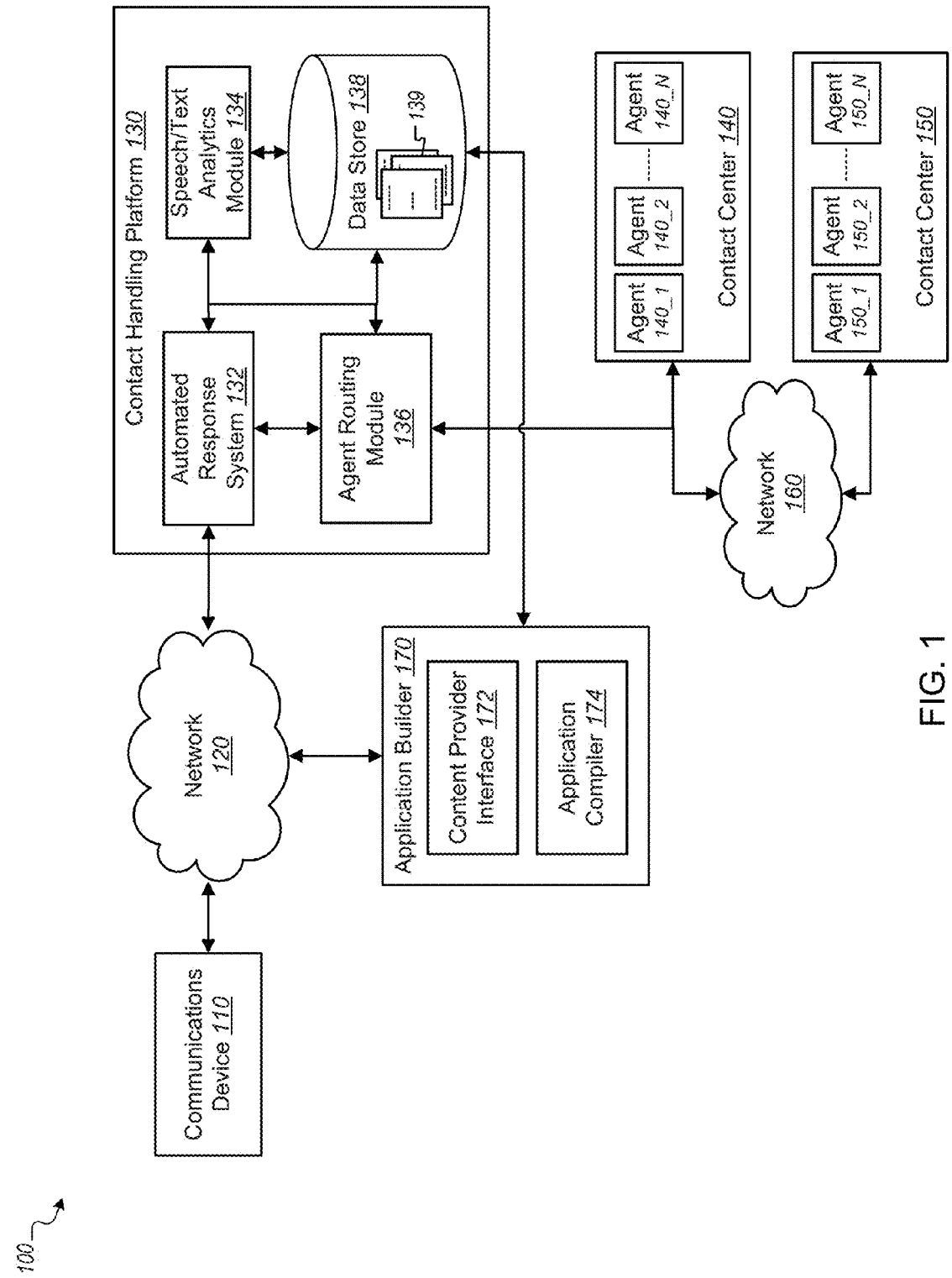
FIG. 1 is a block diagram of a communications system that enables routing user communications to human agents.

A company (e.g., a service provider or a product provider) may wish to enable its customers to contact it through use of any of multiple different communications modes (e.g., phone, email, web chat, SMS or another communications mode that supports communications between a customer and a service or product provider). During a communication session with a customer, the company may wish to interact with customers, at least initially, using an automated response system. In some implementations, use of such an automated response system may decrease the costs associated with responding to customer contacts by decreasing the number of human agents that need to be employed to respond to the customer contacts. This may be the case, for example, when the customer contacts are for routine inquiries (e.g., a customer contacts the company to check the balance of a checking account or of a credit card) and, therefore, lend themselves well to being efficiently and cost-effectively handled through use of an automated response system.

Each of the multiple different communications modes may offer a similar interactive experience to customers. For example, a customer may interact with the company by any one of phone, email, text messaging, and chat/instant messaging through a web browser (also referred to as web chat) to check his bank account balance or his credit card balance. The interaction flow for these multiple different communications modes, therefore, may share many common states and characteristics.

Situations may arise where interaction with a customer using an automated response system is not sufficient, and the communication session with the customer therefore may be routed to human agents for handling. This may be the case, for example, for more complex customer contacts, such as when a customer contacts customer service for the company to troubleshoot a problem the customer is experiencing in using the product or service. The automated response system may not have the resources to provide a solution to the customer's problem, and, therefore, the customer communication may get routed to a human agent with expertise in solving such problems. As another example, a customer may have difficulty navigating the options provided by the automated response system and, therefore, may wish to talk to a human agent. Conversely, in some cases, the automated response system may not understand the customer input (e.g., due to erroneous option selections by the customer during the interaction or due to an inability to understand the customer's accent during a speech-based interaction).

Given the above, it may be useful to provide such companies with the ability to design, and develop a single interaction site that enables customers to interact with the company in an automated fashion via any one of multiple different communications modes, and provides a mechanism to route the customer communication to a human agent when automated interaction is insufficient to address the customer's issues.

The mechanism may implement features that analyze the customer interaction with the automated response system and determine threshold points at which the customer communication should be routed from the automated response system to human agents. The mechanism also may implement features that match a particular customer's communications to specific human agents based on one or more parameters, such as, for example, a type of the communications, an analysis of the customer's state of mind, a history of the customer's past interactions with different human agents, and experience levels of the human agents, among others.

For ease of exposition, the following description begins by describing a voice communications mode involving a voice site, which is configured to receive and respond to telephonic contacts, and then expands the description to cover an interaction site that supports contacts over any one of multiple different communications modes (e.g., email contacts, web chat contacts, and SMS contacts). In a voice communications mode, a customer may call a known customer service number for a product or service. By calling the customer service number, the customer may get connected to a call handling system that enables the customer to interact with a voice site associated with the product or service.

A voice site is a set of scripts or, more generally, programming language modules corresponding to one or more linked pages that collectively interoperate to produce an automated interactive experience with a user. A standard voice site includes scripts or programming language modules corresponding to at least one voice page and limits the interaction with the user to an audio communications mode. Because customers typically access a voice site by calling a telephone number using a voice communications device such as a telephone, a standard voice site is typically referred to as a single mode interaction site, i.e., an interaction site that supports a single type of contact. An enhanced voice site may include scripts or programming language modules corresponding to at least one voice page and at least one multimodal action page linked to the at least one voice page that enable interaction with the user to occur via an audio communications mode and at least one additional communications mode (e.g., a text communications mode, an image communications mode or a video communications mode). An enhanced voice site, therefore, may be referred to as a single mode interaction site that has been enhanced to enable some portions of the interaction flow to involve the communication of multimedia information. Notably, a call may said to be directed to a voice site if it is directed to a telephone number that has been defined as corresponding to the voice site.

The voice site called by the customer may be an automated interactive voice site that is configured to process, using pre-programmed scripts, information received from the customer that is input through the voice communications device being used by the user, and, in response, provide information to the user that is conveyed to the user through the voice communications device. The interaction between the customer and the voice site may be done using an interactive voice response system (IVR) that is included in a contact handling platform (also referred to as a contact handling system) that is hosting the voice site. The contact handling platform is said to be "hosting" the voice site in that it receives and processes the various programming language modules corresponding to the voice site in order to perform the functionality of the voice site. In some implementations, the contact handling platform also may be referred to as a call handling platform, for example, when the contact handling platform is configured to handle primarily voice communications, even though the platform may support other communications modes. The contact handling platform may be provided by a third party service provider, which is referred to as a contact handling platform provider (or simply as a platform provider) in this context.

The IVR is configured to support voice commands and voice information using text-to-speech processing and natural language processing by using scripts that are pre-programmed for the voice site, for example, voice-extensible markup language (VoiceXML) scripts. The IVR interacts with the customer by using audible commands to prompt the customer to provide information and enabling the customer to input the information by speaking into the voice communications device or by pressing buttons on the voice communications device (when using, for example, a touch-tone telephone). The information input by the customer is conveyed to the IVR over a voice communications session that is established between the voice communications device and the IVR when the call is connected. Upon receiving the information, the IVR processes the information using the pre-programmed scripts. The IVR may be configured to send audible responses back to the customer via the voice communications device.

In some implementations, the voice site may be an enhanced voice site that is configured to support multimedia information including audio, video, images and text. In these implementations, the IVR of the contact handling platform is a multimodal IVR that is configured to support the exchange of multi-media information under the direction of the programming language modules of the enhanced voice site. An example of such a multimodal IVR is described in U.S. application Ser. No. 13/092,090, which is incorporated herein by reference for all purposes. The voice communications device also may be an advanced telephonic device (e.g., a smart phone) provided with a display for conveying visual information to the customer, and a processor capable of performing complex tasks such as logic processing wherein the associated instructions may be stored in memory included in the voice communications device. In such circumstances, the advanced voice communications device and the contact handling platform hosting the enhanced voice site can interact using one or more of voice, video, images or text information and commands.

In some implementations, the voice site may be configured to enable the contact handling platform to compute one or more metrics based on the interaction between a customer and the IVR of the contact handling platform when a communication from the customer is received by the IVR. The metrics may be based on various parameters that may be tailored to the voice site by the designer of the voice site. Based on the computed metrics, the contact handling platform hosting the voice site may determine whether to continue interacting with the customer using the IVR, or whether to route the call to a human agent, who may be available at a contact center that is connected to the contact handling platform. For example, the voice site may compare the measured metrics to one or more pre-configured threshold values. If the values of the metrics are below the threshold values, the contact handling platform hosting the voice site may route the customer communication to a human agent. On the other hand, if the values of the metrics are above the threshold values, then the interaction with the customer may be continued using the IVR.

In some implementations, multiple human agents may be available to handle communications from customers that are routed by the contact handling platform to the human agents. For example, several contact centers may be connected to the contact handling platform hosting the voice site, and several agents may be in each contact center. In such implementations, when the contact handling platform hosting the voice site determines to route a customer communication to a human agent, the contact handling platform may perform additional processing in accordance with parameters set for the voice site to select a human agent most suited to handle the particular customer communication. For example, the contact handling platform may execute one or more matching algorithms that consider agent experience levels (represented, for example, using numerical scores), past history of interactions between the particular customer and different available agents, specific agent skills in handling different types of calls (e.g., an agent may have more expertise in handling sales calls while another agent may be adept at handling technical support calls), among other factors.

As noted previously, a customer typically accesses a voice site by calling a telephone number using a voice communications device, such as a telephone. A voice site, therefore, is a single-mode interaction site in that it enables the contact handling platform to receive and respond to customer contacts that are voice calls. In contrast, a multi-modal interaction site enables the contact handling platform to receive and initiate responses to customer contacts in an automated fashion via any one of multiple different communications modes supported by the contact handling platform. For example, a multi-modal interaction site may receive and respond to customer contacts that are voice calls, email messages, SMS messages, web chat messages, or any suitable combination of the above.

A multi-modal interaction site may be a set of scripts or programming modules that offer a common interaction flow for handling customer contacts received in different communications modes. The set of scripts or programming modules may then be translated by an interaction flow processor of the contact handling platform into a corresponding set of mode-specific scripts or programming modules for each communications mode supported by the interaction site, and these translated mode-specific scripts or programming modules may then be executed by the respective sub-systems of the contact handling platform to enable automated interactions with customers over the different modes. For example, the pre-programmed scripts of the interaction site may be extensible markup language (XML) scripts. If the customer contacts the contact handling platform by using a telephone to call a telephone number associated with the interaction site, the interaction flow processor of the contact handling platform may translate the XML scripts of the interaction site to VoiceXML scripts for processing by an IVR to interact with the calling customer. Implementation examples of contact handling platforms able to host multi-modal interaction sites are described in U.S. application Ser. No. 14/032,443, which is incorporated herein by reference for all purposes.

Irrespective of the mode being used for a customer communication, the multi-modal interaction site may implement features to measure various metrics about the automated interaction with the customer, and determine whether to route the communication to a human agent based on the measured metrics. In some implementations, a human agent to whom a communication is routed may be selected from the same pool of human agents available for supporting disparate communications modes. For example, the same human agent may be selected to handle a voice call at one time, respond to an email message from another customer, or chat with a third customer using a web-based chat session. However, in some other implementations, different human agents may be used for supporting disparate communications modes.

The platform provider facilitates the creation and hosting of interaction sites on servers owned and operated by it. The platform provider may provide software or hardware, or both as a means to enable the design and development of an interaction site and to enable the hosting of the interaction site by the contact handling platform. The contact handling platform also may be connected to or may otherwise be in communication with one or more contact centers where human agents are present. The software and/or hardware means also may enable communications/connections between the contact handling platform and the contact centers, such that a customer communication received by the interaction site may be seamlessly routed to a human agent at a contact center.

The software and/or hardware means also may enable the design and development of applications that run a thin client on the communications device used by the customer. The thin client allows a communications interaction between the customer's communications device and an interaction site hosted by the contact handling platform using any one of the communications modes supported by the interaction site.

In the above scenario, the role of the entity (e.g., the company) providing customer service through the interaction site is that of a content provider. The developer of the entity or company (hereinafter referred to interchangeably as the "content provider") configures the interaction site that is to be used for the particular product or service and provides the logic for the interaction site that is to be executed by the contact handling platform. As part of configuring the interaction site, the content provider may select various parameters for which metrics will be computed during an interaction with a customer. The content provider also may specify threshold values for the metrics that may be used to trigger routing a communication to a human agent.

The content provider may configure the interaction site by using a graphical user interface (GUI) provided by the platform provider for configuring the interaction site. The platform provider handles the interpretation and compilation of the information provided by the content provider, and the creation and hosting of the interaction site based on the information. Since the platform provider manages the contact handling platform, the platform provider may enable the content provider to design an interaction site that supports communications with customers over any one of multiple different communications modes using a single, unified GUI.

The software or hardware means provided by the platform provider thus enable the deployment of interaction-enabled solutions on communications devices without requiring the content provider to engage in complex programming Applications, or interaction sites, may be designed by the content provider using a web-based or some other remotely-accessible interface, and served on demand to client applications. In some implementations, the client applications can be add-ons that other smartphone applications can plug into. In some implementations, the software or hardware means enable customers to interact with a multi-modal application. The application is referred to as multi-modal in that it enables an application user (i.e., a customer of the content provider) to contact and interact with the contact handling platform via any of multiple different communications modes (e.g., phone, email, chat, Short Message Service (SMS), or another communications mode that support communications between the user and the interaction site). For example, the user may contact the contact handling platform by phone, provide information to the multi-modal platform by speaking, and receive information from the contact handling platform by hearing. Alternatively, the user may contact the contact handling platform by email (or SMS or web chat), and provide the same information to the contact handling platform by typing text and receive the same information from the contact handling platform by reading text.

FIG. 1 is a block diagram of a communications system 100 that enables routing user communications to human agents. The communications system 100 allows a content provider to configure an interaction site that is operable to handle communications from customers of the content provider using an automated response system, while routing some of the communications to human agents.

The communications system 100 is a multi-modal communications system, i.e., it enables a user to communicate with an interaction site using different modes of communication. Regardless of which mode of communication is used, the communications system 100 facilitates the routing of an established communications session from an automated response system to a human agent as needed.

A customer using a communications device 110 (e.g., a smartphone) is able to interact with the communications device 110 to request communication with an interaction site that is provided, for example, by a content provider. The communication may be, for example, to purchase a particular product or request a service offered by or made available by the content provider through the interaction site. For example, the user may indicate a desire to communicate with the interaction site by selecting a graphically displayed icon on a graphical user interface (GUI) of the communications device 110 to thereby invoke an application stored in the communications device 110 with which the user can interact to initiate a service request. Additionally or alternatively, the user may indicate a desire to communicate by inputting, via manual selection or otherwise, a telephone number associated with a customer service department of the content provider into the communications device 110 and initiating a call directed to the inputted telephone number. Additionally or alternatively, the user may indicate a desire to communicate by inputting and sending, via manual selection or otherwise, a SMS message that includes a short code and a keyword associated with the customer service department into the communications device 110. Additionally or alternatively, the user may indicate a desire to communicate by inputting, via manual selection or otherwise, a uniform resource locator (URL) associated with the customer service department into the communications device 110 to initiate a web chat session with the customer service department. Additionally or alternatively, the user may indicate a desire to communicate by inputting and sending, via manual selection or otherwise, an email that includes an email address associated with the customer service department into the communications device 110. Additionally or alternatively, the user may indicate a desire to communicate via a communications mode not listed in the above examples.

In some implementations, the communications request may be handled by a contact handling platform that hosts the interaction site for the content provider, and communicates with the communications device 110 to provide the requested service. As mentioned previously, an interaction site may be hosted by a third party platform provider that facilitates the creation and hosting of interaction sites on servers owned and operated by the platform provider. Depending on the communications means that a customer uses to access an interaction site, a corresponding handling system included in the contact handling platform may be used to process the request. Each handling system may present the interaction site to the customer in a different manner. For example, a call handling system may present the interaction site to the customer using voice messages that are generated by VoiceXML scripts. On the other hand, an SMS handling system may present the interaction site to the customer using SMS messages that are generated by XML scripts.

However, in many applications, the flow for providing a service to the customer includes the same or similar steps regardless of which communications mode the customer is using. In any of the communications modes being used, the contact handling platform may compute metrics based on the interaction of the customer with the corresponding handling system being used. Depending on whether the computed metrics are above or below pre-configured thresholds, the contact handling platform may route the communications session from the handling system to a human agent for a live person-to-person interaction between the customer and the human agent.

From a content provider's perspective, developing an interaction site for each of the communications modes using different tools or scripting languages can be burdensome. From a platform provider's perspective, the storage and management of an interaction site having different versions for each of the communications modes may be complicated. Accordingly, a communications system that can integrate the development of an interaction site for each of the communications modes using one development platform, and compile the developed interaction site into one scripting language that can be translated based on the communications mode used by a customer may enable a content provider and/or a platform provider to enjoy a decrease in costs associated with developing and managing interaction sites without compromising the quality of the user experience with the interaction site.

The communications system 100 includes a communications device 110 that connects, through a network 120, to a contact handling platform 130. The contact handling platform 130 is directly connected to a contact center 140. The contact handling platform 130 is also connected, over a network 160, to contact center 150. The communications system 100 also includes an application builder 170, which comprises a content provider interface 172 and an application compiler 174.

The communications device 110 is configured to allow a customer to interact with an interaction site hosted by the contact handling platform 130 over the network 120. The communications device 110 may be a voice communications device, such as a telephone, a cellular phone or a satellite phone. The communications device 110 alternatively may be an electronic tablet, electronic book reader, a personal digital assistant (PDA), a portable music player, or a computer, which includes one or more software or hardware applications for performing communications between the communications device 110 and the contact handling platform 130. The communications device 110 may have various input/output devices with which a user may interact to provide and receive audio, text, video, and other forms of data.

The network 120 is configured to allow connections between the communications device 110 and an interaction site hosted by the contact handling platform 130. In some implementations, the network 120 is also configured to allow connections between the application builder 170 and the contact handling platform 130. The network 120 may include a circuit-switched voice or data network, a packet-switched voice or data network, or any other network able to carry voice and/or data, for example, Internet Protocol (IP)-based or asynchronous transfer mode (ATM)-based networks, including wired or wireless networks. The network 120 may be configured to handle voice traffic, for example, Voice over IP (VOIP) network. The network 120 also may be configured to handle web traffic such as hypertext transfer protocol (HTTP) traffic and hypertext markup language (HTML) traffic. The network 120 may include the Internet, Wide Area Networks (WANs), Local Area Networks (LANs), analog or digital wired and wireless networks (e.g., IEEE 802.11 networks, Public Switched Telephone Network (PSTN), Integrated Services Digital Network (ISDN), and Digital Subscriber Line (xDSL)), Third Generation (3G) or Fourth Generation (4G) mobile telecommunications networks, a wired Ethernet network, a private network such as an intranet, radio, television, cable, satellite, and/or any other delivery or tunneling mechanism for carrying data, or any appropriate combination of such networks.

A contact handling platform 130 receives a communications request from the communications device 110 that is directed to an interaction site hosted by the contact handling platform 130, and interacts with the communications device 110 to provide the requested service through the interaction site. The contact handling platform 130 includes several modules, such as the Automated Response System (ARS) 132, speech/text analytics module 134, agent routing module 136, and a data store 138, which stores scripts or, more generally, programming language modules 139 corresponding to interaction sites hosted by the contact handling platform 130.

The ARS 132 is configured to process the communications request from the communications device 110 and interact with the communications device 110 using an automated response system. The ARS 132 may include one or more processors and instructions stored in machine-readable media that are executed by the processors to perform various operations. In some implementations, the machine-readable media may include non-transitory storage media, such as hard disks and hardware memory modules.

In some implementations, the ARS 132 includes an interactive voice response (IVR) system that handles a call from the communications device 110 when the communications device 110 is operating in a voice communications mode. In such implementations, the IVR may include a voice gateway that receives user calls from or places calls to voice communications devices, such as the communications device 110, and responds to the calls in accordance with a voice program that corresponds to a flow of an interaction site. The voice program may be accessed from local memory within the voice gateway or from other storage media in the contact handling platform 130. In some implementations, the voice gateway processes voice programs that are script-based voice applications. The voice program, therefore, may be a script written in a scripting language, such as voice extensible markup language (VoiceXML) or speech application language tags (SALT). The IVR also may be configured to communicate with the data store 138 to read and/or write user interaction data (e.g., state variables for a data communications session) in a shared memory space.

In some implementations, the IVR includes a voice application server and computer systems that interface and provide data to the voice application server. The IVR may process voice application programs or scripts for communicating with the communications device 110. User responses received by the IVR may be analyzed and new programs or scripts that correspond to the user responses may then be processed.

In some implementations, the IVR may initiate an outbound call to the communications device 110. When the outbound call is established, the IVR may interact with the call recipient using the voice program.

In some implementations, the ARS 132 comprises an SMS handling system that is configured to handle a request to interact with an interaction site using an SMS mode. The SMS handling system may include an SMS gateway that receives user SMS messages from, or sends SMS messages to, communications devices, such as the communications device 110, and responds to the SMS messages in accordance with an SMS program that corresponds to a flow of an interaction site. The SMS program may be accessed from local memory within the SMS gateway or from other storage media in the contact handling platform 130. In some implementations, the SMS gateway processes voice programs that are script-based SMS applications. The SMS program, therefore, may be a script written in a scripting language such as, for example, extensible markup language (XML). The SMS handling system also may be configured to communicate with the data store 138 to read and/or write user interaction data (e.g., state variables for a data communications session) in a shared memory space.

In some implementations, the ARS 132 comprises an email handling system that is configured to handle a request to interact with an interaction site using an email communications mode. The email handling system 172 may include an email gateway that interfaces with the network 120. The email gateway is a gateway that receives user emails from or sends emails to communications devices, such as the communications device 110, and responds to the emails in accordance with an email program that corresponds to a flow of an interaction site. The email program may be accessed from local memory within the email gateway or from other storage media in the contact handling platform 130. In some implementations, the email gateway processes email programs that are script-based email applications. The email program, therefore, may be a script written in a scripting language such as, for example, extensible markup language (XML). The email handling system 172 may also be configured to communicate with the data store 138 to read and/or write user interaction data (e.g., state variables for a data communications session) in a shared memory space.

In some implementations, the ARS 132 comprises a chat handling system that is configured to handle a request to interact with an interaction site using a chat channel. The chat handling system may include a chat gateway that interfaces with the network 120. The chat gateway is a gateway that receives user chat messages from communications devices, such as the communications device 110, and delivers chat messages in response to the received user chat messages in accordance with a chat program that corresponds to a flow of an interaction site. The chat program may be accessed from local memory within the chat gateway or from the other storage media in the contact handling platform 130. In some implementations, the chat gateway processes chat programs that are script-based chat applications. The chat program, therefore, may be a script written in a scripting language such as, for example, extensible markup language (XML). The chat handling system also may be configured to communicate with the data store 138 to read and/or write user interaction data (e.g., state variables for a data communications session) in a shared memory space.

The speech/text analytics module (STAM) 134 is configured to perform speech, or text, or both, recognition and grammar matching for the customer communications that are handled by the contact handling platform 130. The STAM 134 may include one or more processors and instructions stored in machine-readable media that are executed by the processors to perform various operations. In some implementations, the machine-readable media may include non-transitory storage media, such as hard disks and hardware memory modules.

In some implementations, the communications data (e.g., voice data, SMS text, web chat text, email text or any suitable combination of the above) that is received as part of a customer communications handled by the ARS 132 is forwarded to the STAM 134. The communications data may be, for example, answers by the call recipient to questions that are presented by the ARS 132 based on the pre-programmed scripts or, more generally, the programming language modules implementing the interaction site. Alternatively or additionally, the communications data may be voice speech that is spoken by the customer, or a human agent, or both, after a customer has been routed to a human agent and the communications session proceeds based on voice interaction between the customer and the human agent.

The STAM 134 may have access to grammars for all possible answers for each question that might be presented by the ARS 132. The STAM 134 also may have access to grammars for various topics or phrases that are configured by the content provider while generating the interaction site. These topics or phrases correspond to topics or phrases that customers of the content provider are likely to query. For example, the content provider may be a mortgage company that configures a phrase to be "Can I reduce my mortgage rate?" or "Can I reduce my rate?" The phrase may be detected as spoken words, or as written text.

In addition, the STAM 134 may have access to grammars for common words or phrases that are likely to be uttered by a customer while communicating with a generic interaction site. These words or phrases may be made available by the platform provider to the content providers as a convenience to thereby allow the content providers to easily incorporate recognition of these common words or phrases into the functionality of their interaction sites. For example, such a topic or phrase may be "I want to talk to an agent" or "I need help," which are topics or phrases that are typically universally applicable to all content providers.

The grammars may be stored in the data store 138, or in memory local to STAM 134, or in other machine-readable media coupled to the contact handling platform 130. The grammars also may be dynamically generated.

The STAM 134 analyzes the communications data received from the communications device 110 during interaction between the customer and the ARS 132 and/or during interaction between the customer and a human agent. The STAM 134 attempts to match the communications data to the grammar that is known to it, or to grammar that is dynamically generated, or to a suitable combination of both. The STAM 134 sends grammar matches for the communications data to the Agent Routing Module (ARM) 136 with a confidence interval. The confidence interval may indicate an extent of match between the communications data and the particular grammar.

The ARM 136 is configured to process customer response data during customer communications that are handled by the contact handling platform 130. The ARM 136 is configured to determine, based on processing the customer response data, whether to route a communications session to a human agent. In some implementations, the ARM 136 is also configured to track agent performance metrics during interactions with customers. In addition, the ARM 136 may be configured to execute agent matching algorithms to route a customer communications session to a human agent most suitable for handling the communications session.

The ARM 136 may include one or more processors and instructions stored in machine-readable media that are executed by the processors to perform various operations. In some implementations, the machine-readable media may include non-transitory storage media, such as hard disks and hardware memory modules.

In some implementations, the ARS 132 forwards to the ARM 136 the customer data (e.g., information corresponding to button presses on the communications device 110) that is received during interaction between the customer and the automated response system. The customer data may be, for example, answers by the call recipient to questions that are presented by the automated response system based on the pre-programmed scripts or, more generally, programming language modules implementing the interaction site. Alternatively or additionally, the STAM 134 forwards results of grammar matches corresponding to vocal or textual data generated by the customer, or a human agent, or both, during a customer communications session involving the customer and one or more of the ARS 132 and an agent in contact center 140 or contact center 150. The grammar matches may each include an identity of the grammar that was matched along with a confidence level indicating an extent of the match between the communications data and the corresponding identified grammar.

Based on the customer data received from the ARS 132, or the grammar matches received from the STAM 134, or both, the ARM 136 computes one or more metrics that provide a measure of the customer's experience during the communications session. In some implementations, the parameters for which the metrics are computed are configured by the content provider while creating the interaction site. In other implementations, the parameters are instead pre-configured by the platform provider hosting the interaction site. The parameters, which are described in greater detail in the following sections, may be associated with or indicative of the customer's satisfaction level during the call.

In some implementations, the ARM 136 determines the customer's satisfaction level during a communications session based on the computed metrics. The customer's satisfaction level may be represented, for example, by a numerical score, which may be referred to as a customer experience score. The numerical score may be an aggregate of the values of the computed metrics. For example, if there are five metrics computed with values 8, 17, 3, 7 and 18 (on a scale of 1-20 each), then the customer experience score is 53 on a scale of 1-100. Alternatively, the base numerical score may be a 100 from which the computed values are subtracted to arrive at the customer experience score. For example, considering the same values for the metrics as above, if the base score is 100, then the customer experience score is 47.

Based on the manner in which the customer experience score is computed, a higher experience score may indicate greater satisfaction of the customer in interacting with the ARS 132, or with a human agent, or both, during a communications session, as compared to a lower experience score. In some implementations, the reverse may be true. In some implementations, more than one customer experience score may be computed. For example, a first customer experience score may be computed based on the interaction of the customer with the ARS 132, and a second customer experience score may be computed based on the interaction of the customer with a human agent. A third customer experience score also may be computed as a sum of the above two customer experience scores.

The ARM 136 may compare the customer experience score to a threshold value and, based on the results of the comparison, decide whether to route the communications session to a human agent. As described previously, the threshold value may be configured by the content provider, who may specify the threshold during creation of the interaction site, or who may configure the threshold to be updated periodically, for example, during regular maintenance of the interaction site configuration. In some implementations, the threshold value may be dynamically generated, or updated, or both, during or based on the operation of the interaction site. For example, the ARM 136 may itself generate or update the threshold value by analyzing customer experience scores from various communications sessions that were initiated as a result of a customer accessing or interacting with the interaction site and/or with other interaction sites. In some implementations, the content provider may specify a range within which the threshold value may be dynamically varied by the ARM 136. In some implementations, there may be several different customer experience scores as noted above, which are compared against several different threshold values.

As noted above, the ARM 136 may decide to route the communications session to a human agent upon comparing a customer experience score to a threshold value. For example, a single threshold value may be specified to be 60, on a scale of 1-100, by the content provider. If a customer's experience score is above 60, the associated communications session is handled by the ARS 132, but if the score is 60 or below, the ARM routes the communications session from the ARS 132 to an agent at a contact center, e.g., 140 or 150.

In some implementations, the ARM 136 also may track performance of the agents based on their interactions with customers during communications sessions. For example, the ARM 136 may compute agent scores that provide a numerical measure of agent performance. The agent scores may be computed by measuring one or more metrics corresponding to agent parameters, which may be configured by the content provider, or pre-configured by the contact handling platform 130, or, by a suitable combination of both.

In some implementations, the agent parameters may include experience level, which provides a quantitative measure of the amount of experience agents have (e.g., in terms of duration of employment, or number of calls, or both) in handling customer communications. For example, the value of the experience level parameter may correspond to "high experience," "medium experience," or "low experience," which may correlate to pre-configured thresholds. An agent with "high experience" may have a higher value assigned to the experience level parameter compared to an agent with "medium experience," who in turn may have a higher value assigned to the experience level parameter compared to an agent with "low experience."

The agent parameters may include skills for handling customer communications in specific categories. For example, expertise in handling customer communications related to sales or technical support may be parameters that are used in computing agent scores.

The agent parameters also may include skills for handling different types of customers. For example, expertise in handling voice communications from customers with certain accents may be an agent parameter used in computing agent scores. In such implementations, the customer accents may be determined by the STAM 134 using speech recognition algorithms. As another example, skill in handling customer communications from customers who are agitated may be an agent parameter used in computing agent scores. This skill may indicate how well (i.e., how successfully and/or quickly) an agent is able to soothe an agitated customer while interacting with the customer.

Another agent parameter that may be considered is the skill of a human agent in up-selling products to a customer, which indicates whether an agent successfully sells a product or service to a customer while interacting with the customer. In addition, this skill may indicate whether the agent is successful in selling additional products or services, or more premium versions of the products or services, to the customer.

The skill of a human agent in providing explanations to a customer may be configured as an agent parameter. This parameter indicates how well an agent is able to answer questions from a customer while interacting with the customer.

In some implementations, the agent parameters may include clarity of speech in interacting with a customer during a customer communications. This parameter indicates how clearly an agent speaks while interacting with a customer using a voice communications mode.

In some implementations, the content provider may configure specific weights for agent parameters corresponding to different skills, which are used in computing agent scores. For example, sales skills may be given a 5% weightage, technical support skills may be given a 7% weightage, and expertise in handling customers with accents may be given a 10% weightage.

The ARM 136 may arrange the agents in an order based on the agent scores. For example, in one implementation the agents may be arranged in a descending order from the agent with the highest agent score to the lowest, while in other implementations the agents may be arranged in a reverse order, i.e., from the agent with the lowest agent score to the highest.

In some implementations, when the ARM 136 determines that a communications session should be routed from the ARS 132 to a human agent, the ARM 136 may perform additional processing to select the most suitable human agent for the communications session. The selection may be based on various factors, which include, among others, agent scores, history of customer experience scores during past interactions with different agents (i.e., the second customer experience score as mentioned previously), the type of the communications (e.g., whether the customer is seeking technical support or has billing questions) and the skills of different agents in handling different types of communications, as mentioned previously.

The ARM 136 may store the customer experience scores, the agent scores, and/or the historical data on customer experience with different agents, in the data store 138 or in memory local to STAM 134, or in other machine-readable media coupled to the contact handling platform 130.

The data store 138 is configured to store instructions executed by the contact handling platform 130 for hosting interaction sites configured by various content providers. For example, the data store 138 may store pre-programmed scripts or, more generally, programming language modules 139 corresponding to interaction sites hosted by the contact handling platform 130. Additionally or alternatively, the data store 138 may be configured to store interaction data corresponding to customer interactions associated with communications sessions, for example, the customer experience scores, the agent scores, and/or other suitable data that are used by the ARM 136.

In some implementations, the data store 138 may store interaction data associated with particular customers of a content provider. The interaction data may include information about the characteristics of the customer and also may include information about the customer's interactions with one or more of the interaction sites of the content provider. For example, the interaction data may include the gender, age, and/or accent of the customer, the choices made by the customer during each state of the interaction with an interaction site (e.g., whether the customer completed specific tasks while interacting with the ARS, or how soon the customer pressed the zero button on the communications device 110 to connect to an agent), and the resources utilized during each state of the interaction with the interaction site (e.g., whether the customer interaction was limited to the ARS 132, or to a human agent, or both). In some implementations, the data store 138 may store aggregated interaction data associated with a particular interaction site. For example, the aggregated interaction data may include data specifying a breakdown of genders among all customers that accessed the particular interaction site. In some implementations, a user may opt-out such that his or her interaction data is then not stored in the data store 138 while in some other implementations, a user may opt-in to have his or her interaction data stored in the data store 160.

In some implementations, the data store 138 may be implemented as one or more database servers, while in some other implementations it may be implemented as a file system. In other implementations, the data store 138 may be implemented as an array of hard disks or other suitable memory modules that are either included within, or coupled to, the contact handling platform 130.

In some implementations, the contact center 140 or the contact center 150, or both, may include a specific physical location, such as a building or an office campus. One or more agents may be physically present in each contact center for interacting with customers when associated customer communications are routed to the agents. For example, agents 140_1, 140_2 through 140_N are present in contact center 140, while agents 150_1, 150_2 through 150_N are present in contact center 150.

In other implementations, one or more of the contact centers 140 or 150 may be a logical grouping of agents who are present in disparate locations. For example, some of the agents 140_1, 140_2 through 140_N may work remotely, e.g., from their respective residences, while some other of the agents 140_1, 140_2 through 140_N may be present in an office building or campus associated with the contact center 140. In some implementations, all of the agents 140_1, 140_2 through 140_N that are managed by the contact center 140 may work remotely, with the contact center 140 providing the infrastructure for coordinating and managing the agents, such as interfacing with the contact handling platform 130, routing to specific agents communications sessions that are received from the ARM 136, and the like.

Some contact centers, such as 140, may be directly connected to the contact handling platform 130, while some other contact centers, such as 150, may be connected remotely, for example through the network 160. In some implementations, the contact center 140 may be co-located with the contact handling platform 130.

The network 160 is configured to allow connections between interaction sites hosted by the contact handling platform 130 and the contact center 150. In some implementations, the network 120 is also configured to allow connections between the contact center 140 and the contact center 150. The network 120 may include a circuit-switched voice or data network, a packet-switched voice or data network, or any other network able to carry voice and/or data, for example, Internet Protocol (IP)-based or asynchronous transfer mode (ATM)-based networks, including wired or wireless networks. The network 120 may be configured to handle voice traffic, for example, Voice over IP (VOIP) network. The network 120 also may be configured to handle web traffic such as hypertext transfer protocol (HTTP) traffic and hypertext markup language (HTML) traffic. The network 120 may include the Internet, Wide Area Networks (WANs), Local Area Networks (LANs), analog or digital wired and wireless networks (e.g., IEEE 802.11 networks, Public Switched Telephone Network (PSTN), Integrated Services Digital Network (ISDN), and Digital Subscriber Line (xDSL)), Third Generation (3G) or Fourth Generation (4G) mobile telecommunications networks, a wired Ethernet network, a private network such as an intranet, radio, television, cable, satellite, and/or any other delivery or tunneling mechanism for carrying data, or any appropriate combination of such networks.

The application builder 170 facilitates the creation of interaction sites. The application builder 190 utilizes various components to enable the creation of interaction sites, such as a content provider interface 172 and an application compiler 174. The different components of the application builder 170 may be co-located in a single physical location, or they may be geographically distributed, with dedicated high capacity links interconnecting the various components. In some implementations, the application builder 170 may be co-located with the contact handling platform 130, such that the two are parts of the same cohesive unit.

A content provider may access the application builder 170 over the data network 120, for example using a computing device that includes one or more software or hardware applications for performing communications with the application builder 170. The computing device used by the content provider may have various input/output modules to exchange audio, text, video, and other forms of data with the application builder 170.

The content provider interface 172 is a GUI front-end for an application builder tool that can be used to build an interaction site that is capable of handling interactions using multiple communications modes. In some implementations, the content provider may access the content provider interface 172 using a web browser that runs on the computing device used by the content provider. By accessing the application builder using the content provider interface 172, the content provider may create interaction sites and interaction pages that will be used by the multi-modal communications system 100 when processing a communications request from a customer to the interaction site created by the content provider.

In the context of this discussion, a "page" is a discrete programming routine configured to perform a discrete function. A page may be defined by a user of the contact handling platform 130 (e.g., a content provider) through an interaction with, for example, a GUI in which the user may indicate the type of programming routine for the page and may optionally further indicate one or more other pages linked to the page. Processing may then proceed to the one or more other linked pages after completion of execution of the page or, alternatively, after initiation of execution of the page but before completion of execution of the page. A page may be compiled into one or more programming language modules or scripts after the page is defined by the user through interaction with the GUI. The one or more programming language modules or scripts may be used, for example, by a handling system to execute the discrete programming routine to perform the discrete function of the page. Examples of different pages include message pages, question pages, logic pages, transaction pages, call queue pages and multimodal action pages. These different pages are described in further detail in the co-pending U.S. application Ser. No. 13/092,090, which is incorporated herein by reference for all purposes.

An interaction page is a particular type of page that is configured to perform the function of delivering content to, or receiving content from, a customer via a communications mode used by the customer to contact the contact handling platform 130 (e.g., voice communications mode for telephone contacts, web chat communications mode for chat contacts, email communications mode for email contacts, and SMS communications mode for SMS contacts). A "voice page" is a particular type of interaction page that is configured to perform the function of delivering audible content to and/or receiving audible content from a customer that called a telephone number assigned to the interaction site. The customer is typically a caller to an IVR and the audible content is typically speech. FIGS. 2A-2H illustrate examples of one or more pages provided by a GUI of an application builder tool, such as the application builder 170.

The interaction sites and pages created by the content provider using the content provider interface 172 are interpreted and/or compiled by an application compiler 174 to generate scripts or, more generally, programming language modules that are executed by the contact handling platform 130 to interact with a user accessing the interaction site. In some implementations, the application compiler 174 may generate an interaction flow document, which may include XML scripts or code that correspond to pages (i.e., programming modules) of an interaction site created by the content provider. The interaction flow document may be stored in the data store 138. The one or more processors included in the contact handling platform 130 may access the scripts from the data store 138 and translate them into a language that can be processed by a particular handling system when the contact handling platform 130 interacts with a customer communicating with the interaction site.

In addition to the XML scripts, the application compiler 174 may also generate other types of scripts (e.g. Java scripts) and other types of executable code using other programming languages based on pages created for the interaction site by the content provider (e.g., based on transaction pages). The other types of scripts may be used by the contact handling platform 130 to interact with the customer communicating with the interaction site over the data network 120.

FIGS. 2A-2H illustrate an example GUI 200 for an application builder tool that is used by a content provider to create an interaction site for a communications system that enables routing user communications to human agents. In general, each interaction site includes a flow of the interaction states that provide an overview of how users interact with the interaction site during the execution of the interaction site. A state may be configured using a page, such as, for example, a voice page or, more generally, an interaction page. In some implementations, the states of the flow for an interaction site are the same across multiple communications channels. For example, a first customer may access an interaction site using a voice communications device, and in the first state, the first customer would experience a "Say Greeting" interaction page that greets the first user via voice. A second customer may access the same interaction site using SMS, and according to the flow, the second customer would also interact with the "Say Greeting" interaction page that greets the second customer via a SMS message.

It may be a tedious process if the content provider is required to configure the same greeting message for each of the communications channels. The content provider interface 172 of the application builder 170 provides the content provider with a unified interface to create and configure pages that are common to the various communications modes without the need to enter duplicate information for these communications modes. For example, the GUI 200 may be implemented by the content provider interface 172 included in the application builder 170 that is used by content provider for creating and managing an interaction site hosted by the contact handling platform 130. Accordingly, the following sections describe the GUI 200 with respect to the communications system 100. As a specific example, the components of the GUI 200 are described as used by a cellular service provider, referred to as "Exemplary Cellular," to create an interaction site for providing customer service to its cellular subscribers. However, the GUI 200 and the associated application builder tool may be used by other systems, content providers or application developers to create any interaction site to perform any desired automated interaction flow in response to a customer contact.

Figure 2A:
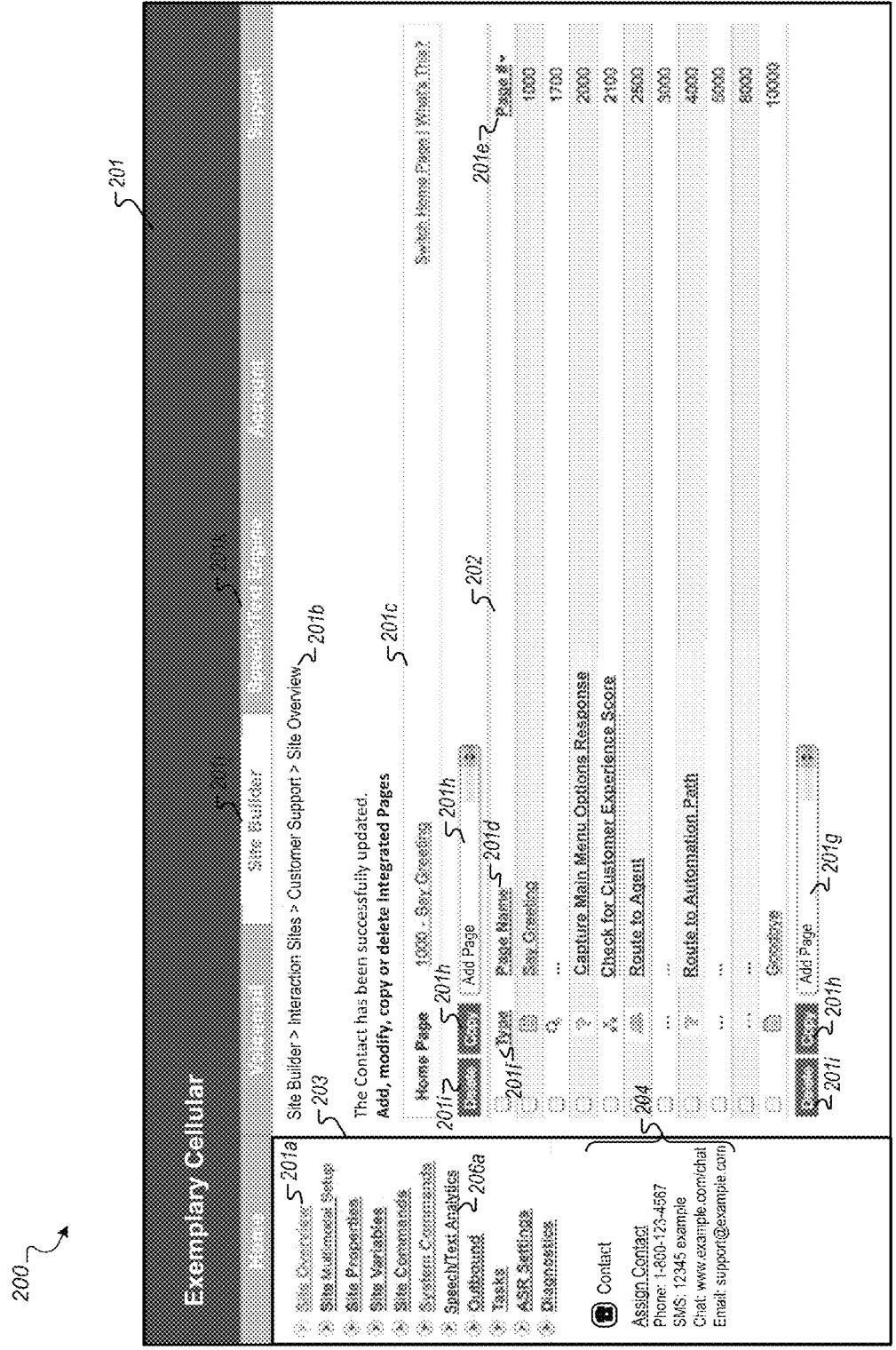
FIGS. 2A-2H illustrate an example GUI for an application builder tool that is used by a content provider to create an interaction site for a communications system that enables routing user communications to human agents.

FIG. 2A illustrates an example GUI 200 showing a site overview page 201 that is presented to the content provider when the content provider logs into the application builder 170 (e.g., by inputting a user identifier and a password) via, for example, a web browser running on the computing device used by the content provider. The Site Overview page 201 may be accessed by the content provider by selecting an interaction site from among a displayed list of interaction sites associated with (e.g., designed by, or for) the content provider, clicking on the desired interaction site (e.g., "Customer Support") and then clicking on the "Site Overview" link 201a in the navigation panel 203. In some implementations, the content provider may have to click on a top level tab, such as "Site Builder" 201j, before clicking on the "Site Overview" link 201a. In some implementations, the navigation panel 203 is present to the left of the page currently displayed (e.g., the Site Overview page 201) and provides links to various system pages that can be directly accessed by the content provider from the page currently displayed.

The Site Overview page 201 provides a listing, referred to as the page flow 202, of all the different pages created by the content provider to define the particular interaction site (e.g., "Customer Support" in the example shown). The name of the interaction site is specified in the heading 201b of the Site Overview page 201 (e.g., "Customer Support").

When a customer communicates with the "Customer Support" interaction site, the first page that is processed is identified in the "Home Page" field 201c. The content provider may specify any page that the content provider wants to be processed first as the Home Page 201c. In some implementations, the first page in the listing of pages is the same page that is listed as the "Home Page" 201c. However, in other implementations, the page that is the "Home Page" 201c is not the first page in the listing of the pages in the Site Overview page 201.

The order in which the various pages are processed is determined by the links in the respective pages. Each page usually contains a link to the next page that is to be processed. For example, the interaction site illustrated in the Site Overview page 201 has a page flow 202 of several interaction pages, including the interaction pages "Say Greeting", "Capture Main Menu Options Response", "Check for Customer Experience Score," "Route to Agent," "Route to Automation Path" and "Goodbye." A descriptive page name, which is shown by the Page Name field 201d, is associated with each page and helps to identify the function of the corresponding page. In addition, each page also may be identified by a page number that is shown in the Page # field 201e. The page name and page number of a page are specified by the content provider when creating the pages for the interaction site. A page may have a unique page name, or it may have a page name that is similar to the page name of another page. In case two or more pages share the same page name, they may be differentiated based on the page numbers. In some implementations, a page may be referred to by different names in different linking pages. However, the page number for each page uniquely identifies a page. A user may access and modify any of the pages displayed in the page flow 202 by selecting them from the displayed list.

In some implementations, the type of each page is denoted by a graphical icon that is shown by the Type field 201f. Pages of different types may have different icons. For example, the pages "Say Greeting" and "Goodbye" are message pages, "Capture Main Menu Options Response" and "Route to Automation Path" are question pages, "Check for Customer Experience Score" is a logic page and "Route to Agent" is a call queue page, as indicated by their different icons.

Additionally or alternatively, in some implementations the Site Overview page 201 may present the pages in a two dimensional or three dimensional display that visually depicts the links between the pages. For example, each page may be displayed as a page graphical element, such as, for example, a rectangle or a block, with one or more link graphical elements, such as, for example, lines, connecting the page graphical elements to other page graphical elements to which they are linked. Text may be overlaid on or displayed in proximity to the page and/or link graphical elements to communicate the identity of the corresponding page and/or the nature of the link between the elements.

The content provider may create a new page by clicking the "Add Page" button icon 201g. When the "Add Page" button icon 201g is clicked, a new page is added to the page flow 202. In response to selecting the button icon 201g, the GUI 200 may present a set of page templates for selection in, for example, a drop-down list. The page templates may include, for example, message pages, question pages, logic pages, call queue pages, transaction pages, and multimodal action pages. The user may select a page template from the list to generate a page of the corresponding type using the template. The template presents to the user the necessary fields and/or controls for that page type and the user may populate the fields (e.g., by typing text into the fields) and/or select the controls to generate a page of the corresponding type.

Alternatively, a new page may be created by copying a previously created page. The content provider may select the page to be copied by checking the checkbox to the left of the page to be copied and then selecting the "Copy" button 201h. An existing page can be deleted by checking the checkbox to the left of the page, and then clicking the "Delete" button 201i.

In some implementations, the contact information for the interaction site is provided by the contact field 204 in the navigation panel 203. The contact field 204 includes information corresponding to each communications mode supported by the interaction site. In the example shown in FIG. 2A, the "Customer Support" interaction site supports telephone, SMS, web chat and email communications modes, and therefore the contact field 204 includes information for each of these modes. A customer communicating with the interaction site may either call the telephone number 1-800-123-4567, send an SMS to "12345 example," send web chat messages to www.example.com/chat, or send an email to support@example.com, as shown by the contact field 204, or use any suitable combination of all of the above.

Figure 2B:
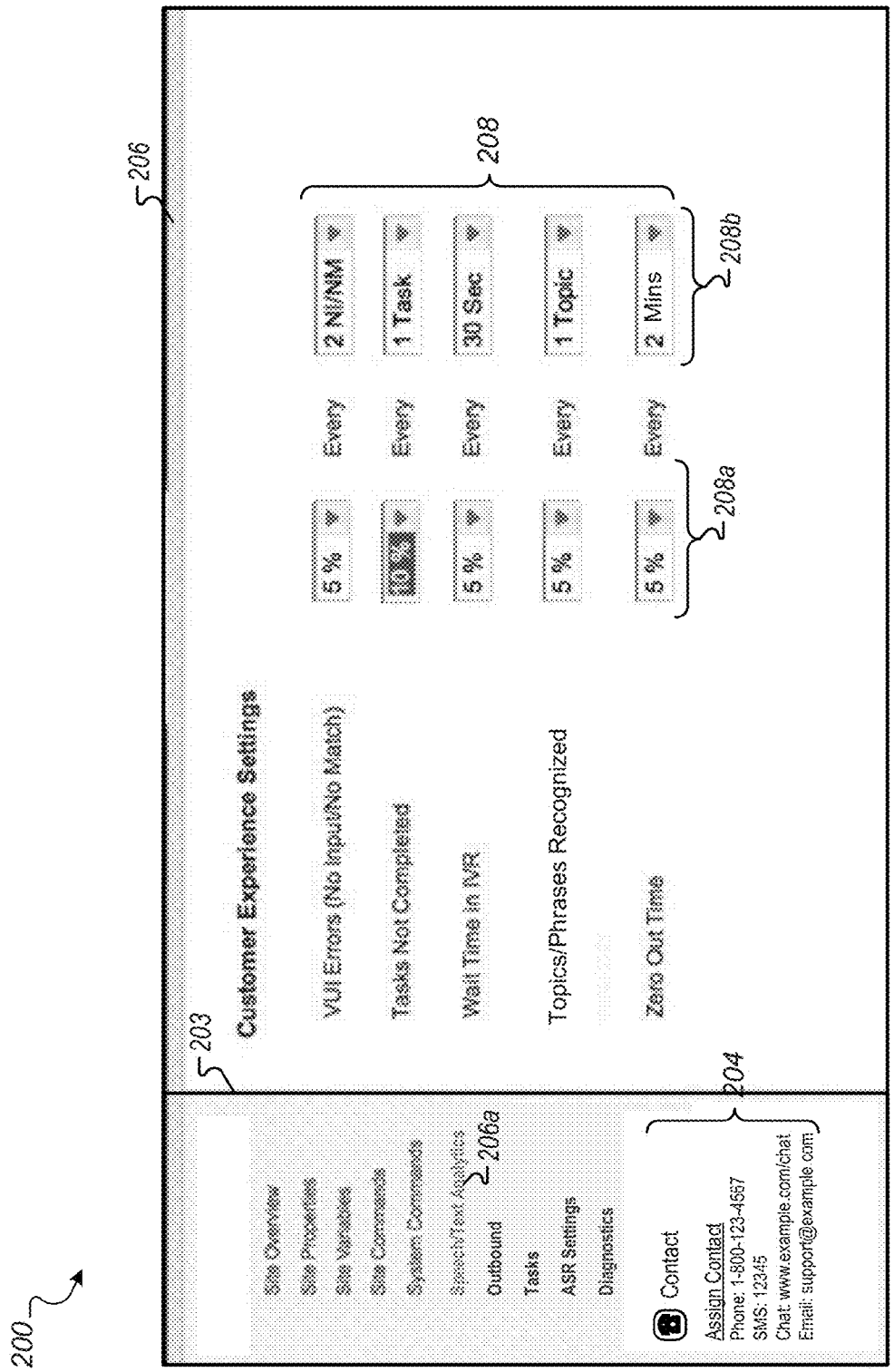

As described previously, as part of generating the interaction site, the content provider may configure various parameters that are to be used by the contact handling platform 130 for computing performance metrics for customer communications with the interaction site. In some implementations, the content provider may configure these parameters using settings interfaces. FIG. 2B illustrates an example GUI 200 showing a settings interface "Customer Experience Settings" 206 that is presented to the content provider when the content provider configures parameters used by ARM 136 in computing metrics for customer communications. In this context, a settings interface is an interface (e.g., a web page) accessible through a web browser that provides various application-level data points or parameters, which are used by scripts or, more generally, programming language modules implemented by the interaction pages in computing a customer experience score. The customer experience score is a system variable that is used by the application (i.e., the interaction site) in determining whether to route a customer's communications from the ARS 132 to a human agent. In particular, the customer experience score is used by the ARM 136 in determining the routing path for a customer's communications made to an interaction site hosted by the contact handling platform 130. A settings interface is differentiated from an interaction page in that a settings interface does not describe scripts or, more generally, programming language modules that are executed as part of an interaction flow between a customer and an interaction site.

A content provider may access the interface 206 by selecting an interaction site from among a displayed list of interaction sites associated with (e.g., designed by, or for) the content provider, clicking on the desired interaction site (e.g., "Customer Support") and then clicking on the "Speech/Text Analytics" link 206a in the navigation panel 203. In some implementations, the content provider may have to click on a top level tab, such as "Site Builder" 201j, before clicking on the "Speech/Text Analytics" link 206a in the navigation panel 203.

The interface 206, as shown, includes application-level settings or parameters 208 that are used when a customer interacts with a call handling system, such as an IVR, during a communications session using voice communications mode. In some implementations, the GUI 200 may include different settings interfaces for different handling systems, such as SMS, email, or web chat, that are used for computing metrics when the corresponding communications mode is used during interaction between the customer and the interaction site. In some implementations, different parameters may be configured for the different settings interfaces, while in other implementations, the different settings interfaces may use the same parameters, but with different configured values for the different communications modes. In some implementations, the GUI 200 may include a single settings interface to set the parameters that will be used for all of the different handling systems.

In some implementations, the platform provider may pre-configure the parameters that are shown in a settings interface. In other implementations, the platform provider may enable the content provider to select from a set of parameters that are to be included in a settings interface, or enable the content provider to create its own parameters, or a suitable combination of both.

Referring to the interface 206, the parameters 208 include "VUI (Voice User Interface) Errors (No Input/No Match)," "Tasks Not Completed," "Wait Time in IVR," "Topics/Phrases Recognized," and "Zero Out Time." The ARM 136 measures "VUI Errors (No Input/No Match)" when a customer, while interacting with an IVR during a voice call, either does not provide an input (i.e., "no input" (NI)) in response to a query from the IVR, or provides an incorrect input that does not match (i.e., "no match" (NM)) the response expected by the IVR. For example, when interacting with the customer regarding billing, the IVR may query "Press 1 to hear your bill; press 2 to make a payment; press 3 to return to the main menu." After making this statement, the IVR waits for a pre-determined time period (e.g., 5 seconds)

for the customer to press one of the buttons numbered 1, 2, or 3 on the communications device 110. However, the customer may not press any button before the time period expires, in which case the IVR may log the lack of response as one occurrence of a "no input" (NI) VUI error. Alternatively, the customer may press button numbered 5 on the communications device 110, which is different from any of the selections expected by the IVR in response to the query. In this case, the IVR may log the response as one occurrence of a "no match" (NM) VUI error. In some implementations, after such an error occurs, the IVR may repeat the query to allow the customer to make a correct selection in a fresh attempt. In some implementations, the content provider may configure whether the IVR repeats the query or how many times the IVR repeats the query.

The "VUI Errors (No Input/No Match)" may occur, for example, when the IVR is not well-designed such that the customer is confused, or when the customer is frustrated or angry and does not want to interact with the IVR. For these reasons, ARM 136 can use "VUI Errors (No Input/No Match)" as a metric indicating a degree of satisfaction, or ease of use, of the customer in interacting with the IVR. A number of "VUI Errors (No Input/No Match)" above a certain threshold may indicate that the customer is unhappy or having difficulty with the automated response system, and therefore the call should be routed to a human agent who may be better able to meet the customer's needs.

The "Tasks Not Completed" parameter is measured when a customer does not complete a task, which may comprise series of interactions with the automated response system. For example, a task may be that the customer provides her credit card information for a transaction, which includes the customer making a series of button presses on her voice communications device to enter the credit card number. In this exemplary situation, "Tasks Not Completed" may be measured when, instead of completing entering the credit card number, the customer repeatedly presses some non-numeric button, such as "#" or "*," on her voice communications device, which may be an expression of the customer's dissatisfaction or difficulty in interacting with the automated response system. In this particular example, the "Task Not Completed" measurement also corresponds to a "VUI Error (No Match)" measurement. A number of "Tasks Not Completed" measurements above a certain threshold may indicate that the customer is unhappy or having difficulty with the automated response system, and therefore the call should be routed to a human agent who may be better able to meet the customer's needs.

In some implementations, a content provider, while designing or modifying an interaction site, may identify tasks of the interaction site as a group of interlinked pages of the interaction site. Specifically, the content provider may define a set of different tasks for an interaction site, with each task in the set corresponding to a different grouping of one or more interlinked pages. For example, the task of requesting a checking account balance may be identified as pages #1000 through #4200 of a bank's interaction site, and the task of transferring money between bank accounts may be identified as pages #7200 through #7700 of the bank's interaction site. A customer's progression through the pages corresponding to a task may be tracked to determine whether or not a task is successfully completed.

A task may, therefore, be defined as a sequence of interactions with the IVR that may correspond to, for example, a set of interlinked pages. If a customer fails to complete the full sequence of interactions corresponding to the task, the task may be deemed not completed. For example, if the customer provides the input for the first two pages of a task that constitutes 4 interlinked pages but then fails to provide the desired input for the third page of the task by, for example, choosing an option that results in the interaction flow instead going back to a main menu of the IVR, the task will be deemed not completed. Such behavior constitutes a "Task Not Completed" measurement and not a "VUI Error (No Input/No Match)" measurement.

In some implementations, a series of "VUI Errors (No Input/No Match)" may constitute a "Tasks Not Completed" measurement. This may be the case, for example, when the task at issue includes a number of sub-tasks. Each sub-task may be an IVR query, with the IVR expecting the customer to make a specific button press on the customer communications device in response to the query. However, on the first attempt for some of these sub-tasks, either the customer does not provide an input within the time out period, leading to a "no input (NI)" error, or the customer makes a button press different from that expected by the IVR, leading to a "no match (NM)" error. The task may be deemed not completed if a threshold number of VUI errors occur, causing the IVR to terminate the task prematurely and return to, for example, a main menu.

When the ARM 136 routes a customer communications to a human agent, but the customer has to wait before he or she is connected to the agent, the "Wait Time in IVR" parameter is measured. In some implementations, the metric provides an indication of the customer's dissatisfaction as the customer waits in a connection queue before he or she is connected to an agent. The higher the value of the "Wait Time in IVR" metric, (i.e., the longer the customer has to wait in queue), the more dissatisfied the customer is likely to be. Therefore, in some implementations, the metric is provided to the human agent when the call is connected such that the agent is aware of the customer's potential heightened dissatisfaction with the communications session.

The "Topics/Phrases Recognized" parameter corresponds to words spoken by the customer that form part of topics or phrases configured to escalate, i.e., speedily route, the customer communications session to a human agent. In some implementations, the STAM 134 records and analyzes the customer speech when the customer interacts with the ARS 132. In analyzing the customer's speech, the STAM 134 looks for certain words or phrases spoken by the customer that are identified by the content provider, or the platform provider, or both, as indicative of the customer's level of dissatisfaction in interacting with the ARS 132. For example, when the ARS 132 asks the customer to make a certain button press on his or her voice communications device to respond to an ARS query, the customer, instead of making the button press, may say "I hate this," or "I want to talk to an agent." The STAM 134 may find a match for this customer utterance with a phrase configured by the content provider, and provide this information to the ARM 136.

In some implementations, upon receiving the information from the STAM 134, the ARM 136 may route the call immediately to a human agent. In other implementations, the ARM 136 may update the value of the metric corresponding to "Topics/Phrases Recognized." When the value of the metric reaches a pre-determined threshold, it may indicate that the customer is dissatisfied. Consequently, at this point the ARM 136 may route the call to a human agent, who may be better able to handle the call.

The "Zero Out Time" parameter measures how quickly a customer attempts to talk to a human agent after a communications session is established with the contact handling platform 130. In some implementations, when the ARS 132 initiates interaction with the customer after a call is connected, the customer may not want to interact with the automated response system, but instead want to talk to an agent. The customer may indicate his or her intention by pressing the zero or other well-known button on his or her voice communications device, which, in some implementations, may indicate a connection to an agent. Upon detecting the customer pressing the zero or other well-known button, the ARS 132 may log the input and forward the information to the ARM 136, which updates the measurement of the metric corresponding to "Zero Out Time."

In some implementations, the ARM 136 may route the call immediately to a human agent, while in other implementations the ARM 136 may wait till the value of the metric reaches a certain threshold, at which point the call is routed to a human agent. A high value of the metric above the threshold may indicate that the customer is dissatisfied, and therefore the call should be routed to a human agent who may be better able to handle the call.

Each of the parameters 208 is characterized by a weight 208a, and a unit of measurement 208b. The weight 208a indicates the numerical value that is assigned to a parameter by the ARM 136, while the unit 208b indicates the granularity at which the value is assigned, for occurrence of the condition corresponding to the parameter during a communications session. The assigned value is used to compute the overall customer experience score. For example, as shown, considering the "Topics/Phrases Recognized" parameter, for every detection of words or phrases in the customer's speech that matches one topic or phrase (i.e., the unit 208b) pre-configured in the system, a 5% weight 208a is assigned to the parameter.

Considering the "Zero Out Time" parameter, if the ARS 132 detects that the customer has pressed the zero button, for example to indicate that he or she wants to talk to an agent, a 5% weight 208a is assigned if a positive detection is made in every 2 minute time interval (i.e., the unit 208b). In some implementations, the time interval for the "Zero Out Time" parameter indicates the frequency at which occurrences of the zero button press is measured. In such cases, the weight assigned to the parameter will be 5% in a 2 minute time interval even if the customer presses the zero button 10 times within that time interval. In the another 2 minute time interval, the weight assigned also will be 5%, even if the customer presses the zero button 1 time within that time interval. However, in some other implementations, every press of the zero button is measured. For example, if the customer presses the zero button 10 times within a 2 minute time interval, then weight assigned to the parameter will be 5%×10, i.e., 50%. In such cases, the time interval may not be used in computing the value of the "Zero Out Time" parameter.

In the above example, the ARM 136 may set the default value of the overall customer experience score to 100%, which indicates that the customer is fully satisfied in interacting with the ARS 132. If a 5% weight is assigned to the "Topics/Phrases Recognized" parameter, the ARM 136 updates the customer experience score to 100%–5%=95%. Then, if a 5% weight is assigned to the "Zero Out Time" parameter, the ARM 136 updates the customer experience score to 95%–5%=90%. In this manner, for every assignment of a weight to one of the parameters 208 by the contact handling platform 130, the customer experience score is updated to reflect the occurrence of the condition being measured by the corresponding parameter.

In some implementations, the weights 208a and the units 208b are pre-determined by the contact handling platform 130, and provided to the content provider when the corresponding parameters are selected by the content provider. In some implementations, the content provider may be allowed to set its own weights and/or units, or change the values of the weights and/or units provided by the contact handling platform. This may be useful in situations where the content provider wants to customize the response of its interaction site to suit the perceived needs of its customers, which may differ from content provider to content provider, or from interaction site to interaction site, or both.

For example, the contact handling platform 130 may set the default weight 208a and unit 208b of the "Topics/Phrases Recognized" parameter to 20% for every 3 topics, respectively, in which case the ARM 136 will assign a weight of 20% to the parameter in intervals of every three detections of words or phrases in the customer's speech that matches topics or phrases pre-configured in the system. However, these values may be unsuitable for a particular content provider, who may consider that either the default weight is too high, or the frequency of detection (i.e., the unit) is too low, or both. Therefore, the content provider may change the weight 208a and unit 208b of the "Topics/Phrases Recognized" parameter to 5% for every 1 topic, as shown and discussed previously.

In this manner, the content provider may customize the weights and/or units of measurement for the parameters that it selects. In some implementations, such as when all the parameters available in the system are provided in the setting interface 206, the content provider may de-select a parameter by setting its weight to 0%. Therefore, for every occurrence of the associated condition, a 0% weight will be assigned to the parameter based on the unit of measurement. Consequently, the customer experience score that is computed will be unchanged, since, for example, 90%–0%=90%.

As indicated previously, other parameters may be available in and used by the system, which are not selected by the content provider and therefore are not shown by the settings interface 206. For example, "Navigation Pattern" is a parameter that is used for measuring the customer's responses and actions when interacting with the ARS 132. This parameter may measure what buttons the customer is pressing on his or her communications device during the interaction, and whether these customer inputs match the pattern of behavior expected by the ARS 132. Customer inputs that do not match the expected pattern of behavior (i.e., they are unrecognized by the ARS 132) potentially indicate that the customer is having difficulty in interacting with the automated system. In some implementations, the "Navigation Pattern" parameter may include the "Tasks Not Completed" parameter as a subset.

Another parameter is "Zero Action," which may be measured when the customer provides some pre-configured input to indicate a desire to connect to a human agent during an interaction with the ARS 132, irrespective of whether the ARS 132 expects some other input in response to ARS queries. For example, the interaction site may be configured such that in voice communications mode, a '0' button press on a customer's voice communications device may be reserved for an agent connection request. The customer may press the '0' button one or more times while interacting with the ARS 132, even if the ARS may be requesting some other input. This may potentially indicate strong desire on the customer's part to talk to an agent, instead of the ARS.

In some implementations, the weights 208a are not assigned as percentages but rather are assumed using some other unit, such as absolute values. This may be the case, for example, when the customer experience score is computed as a sum of the weights, instead of by subtracting the weights from a default customer experience score as shown in FIG.

2B. In such a case, the default customer experience score may be 0, and for every weight assigned to a parameter, the customer experience score is updated by adding the weight to the score. For example, the "Topics/Phrases Recognized" parameter may have a weight of 5. When the corresponding condition is detected by the system, the customer experience score is updated to 0+5=5. The "Tasks Not Completed" parameter may have a weight of 10. When the corresponding condition is detected by the system, the customer experience score is updated to 5+10=15.

Figure 2C:
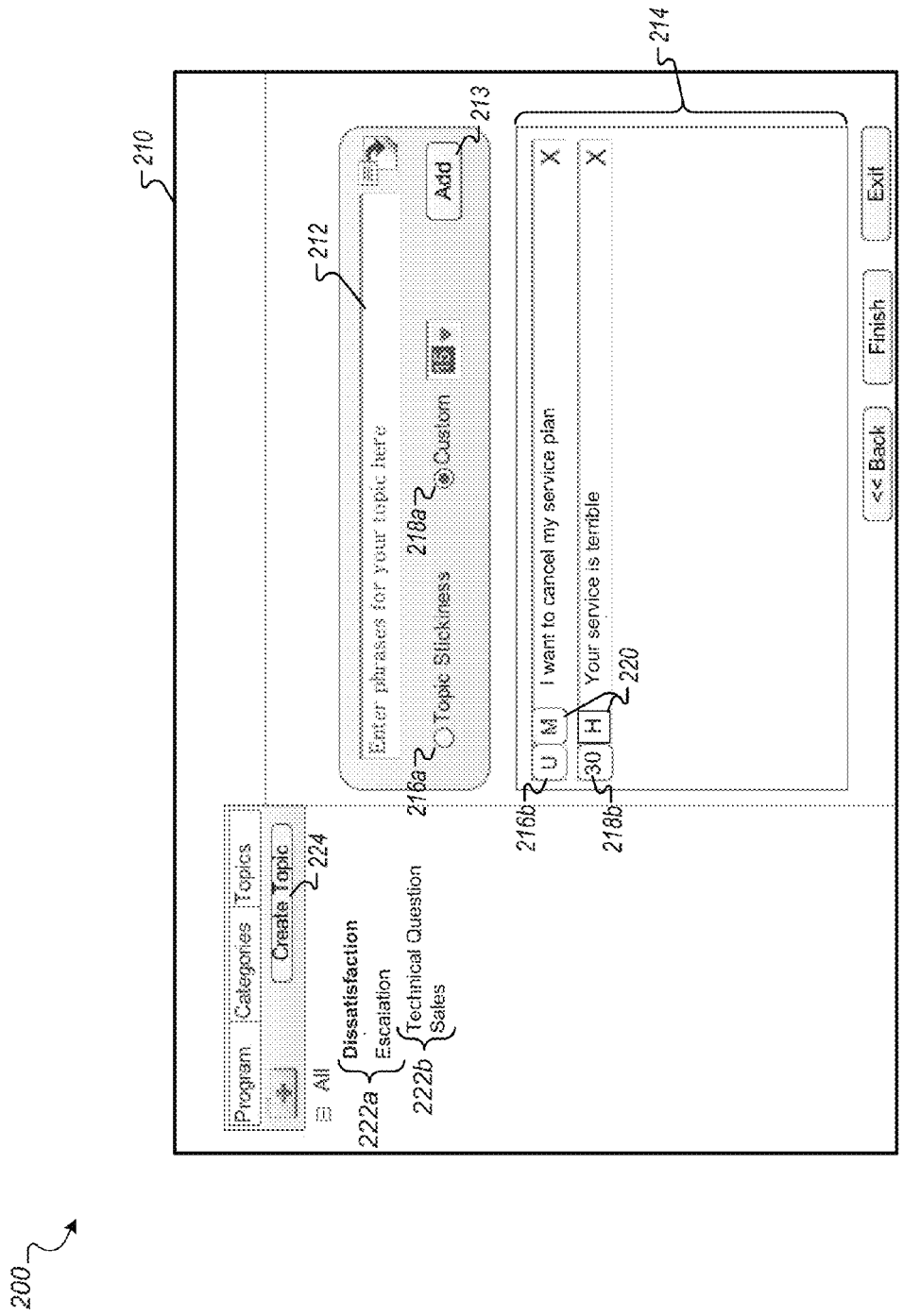

As indicated previously, in some implementations the content provider configures the topics or phrases that are used by the STAM 134 while analyzing the customer's speech for the "Topics/Phrases Recognized" parameter. FIG. 2C illustrates an example GUI 200 showing a settings interface 210 that is presented to the content provider when the content provider configures the topics or phrases that are used for the "Topics/Phrases Recognized" parameter. In particular, the STAM 134 checks whether the customer's speech includes one or more of the topics or phrases configured in the settings interface 210. For every match that is found, the STAM 134 informs the ARM 136, which updates the "Topics/Phrases Recognized" parameter based the associated weight 208a, at the frequency indicated by the unit 208b.

The content provider may access the interface 210 by selecting an interaction site from among a displayed list of interaction sites associated with (e.g., designed by, or for) the content provider, clicking on the desired interaction site (e.g., "Customer Support") and then clicking on the "Speech/Text Engine" tab 201k. Additionally or alternatively, in some implementations, the interface 210 may be accessed by selecting a link in a tab, rather than by selecting the tab 201k. For example, the interface 210 may be accessed by selecting a link in the navigation panel 203 of the "Site Builder" tab 201j.

The interface 210, as shown, includes topics or phrases, or both, that are used when a customer interacts with a call handling system, such as an IVR, during a communications session using voice communications mode. In some implementations, the GUI 200 may include different settings interfaces for different handling systems, such as SMS, email, or web chat, that are used for computing the "Topics/Phrases Recognized" parameter when the corresponding communications mode is used during interaction between the customer and the interaction site. In some implementations, different topics or phrases may be configured for the different settings interfaces, while in other implementations, the different settings interfaces may use the same topics or phrases, but with different values for the topic stickiness, which is describe below. In some implementations, the GUI 200 may include a single settings interface to set the topics or phrases that will be used for all of the different handling systems.

In some implementations, the platform provider may pre-configure the topics or phrases that are shown in the settings interface 210. In other implementations, the platform provider may enable the content provider to select from a set of pre-determined topics and phrases, or enable the content provider to create its own topics and phrases, or a suitable combination of both. For example, the content provider, such as the cellular service provider "Exemplary Cellular" described previously, may enter keywords or phrases in the input field 212 and generate a phrase for use by the STAM 134 by pressing the "Add" button 213. Phrases that are created by the content provider are displayed in the panel 214, such as the phrases "I want to cancel my service plan" and "Your service is terrible," as shown.

When generating a phrase, the content provider may specify the "topic stickiness" for the phrase, which is a confidence-level that provides a threshold value for the system to determine whether a match for the associated phrase is detected in the customer's speech. For example, if the topic stickiness is configured as 70%, then the STAM 134 may determine a match for the corresponding phrase in the customer's speech if the STAM 134 is at least 70% confident in its determination.

For each configured phrase, the content provider may specify universal topic stickiness by selecting the radio button 216a, or custom topic stickiness by selecting the radio button 218a. The universal topic stickiness is a system-wide value that is used by default unless the custom topic stickiness is selected. In some implementations, the universal topic stickiness is pre-configured by the contact handling platform 130, while in other implementations the content provider specifies a value of the universal topic stickiness, such as 80% confidence-level. The value that is configured for the universal topic stickiness provides an indication of the degree of certainty that the content provider desires in the speech analysis and pattern matching performed by the STAM 134. That is, a higher universal topic stickiness value indicates that a higher degree of certainty in the results generated by the STAM 134 is necessary before the STAM 134 concludes that a match has occurred. This may be useful, for example, in cases where the content provider does not have much margin for error in analyzing the customer's speech, such as when the content provider is a compliance-enforcement organization.

The custom topic stickiness is selected by the content provider when it wants to specify a confidence-level other than the default value for particular phrases. This may be useful, for example, when the content provider wants the STAM 134 to determine that a match of a particular phrase has occurred when the match certainty or confidence exceeds a threshold confidence level that is different from that specified by the default confidence-level. In such cases, the content provider specifies the custom confidence-level as part of generating the phrase by selecting the radio button 218a, and specifying the value for the confidence-level in the associated field.

When the universal topic stickiness is selected for a phrase, then the icon "U" 216b is shown next to the associated phrase in the panel 214. On the other hand, when the custom topic stickiness is selected for a phrase, then the icon 218b showing the specified confidence-level value is presented next to the associated phrase in the panel 214. For example, the cellular service provider may configure the default confidence-level to be 70%, and specify the phrase "I want to cancel my service plan" with universal stickiness. On the other hand, the cellular service provider may specify the phrase "Your service is terrible" with a custom stickiness having the confidence-level value of 30%. Consequently, when the STAM 134 analyzes the speech of a cellular subscriber who calls the cellular service provider's interaction site, such as the "Customer Support" site described previously, the STAM 134 determines an affirmative match for the phrase "I want to cancel my service plan" if it is at least 70% confident in its determination. However, the STAM 134 may determine an affirmative match for the phrase "Your service is terrible" if it is even 30% confident in its determination.

When the content provider generates a phrase using the interface 210, the contact handling platform 130 analyzes the phrase and provides a rating for the effectiveness of the keyword or phrase, which is displayed using the icon 220 next to the associated phrase. The effectiveness indicator is a system-generated analysis of the strength of the keywords or the phrase, or the length of the phrase, for use by the STAM 134.

For example, when the cellular service provider configures the phrase "I want to cancel my service plan," the contact handling platform 130 may rate the phrase to be of medium effectiveness, as shown by the "M" icon next to the phrase in the panel 214. The medium effectiveness indicates that the keywords included in the phrase are of medium strength in helping the STAM 134 to find a match for the phrase in a customer's speech. In contrast, if the cellular service provider had configured the same phrase as "cancel," then the contact handling platform may have rated the phrase as low effectiveness (e.g., by affixing the icon "L" next to the phrase), indicating that the keywords included in the phrase are of low strength in helping the STAM 134 to find a match for the phrase in a customer's speech. On the other hand, if the contact handling platform 130 determines a phrase to be highly effective, it indicates such a rating by the icon "H," as shown associated with the phrase "Your service is terrible." In this manner, the contact handling platform uses the effectiveness indicator to help the content provider configure phrases that are easier to recognize by the STAM 130, and accordingly return more accurate results corresponding to customers' speeches.

The content provider may group the phrases into different topic categories, which are shown by the listing 222a in the settings interface 210. In some implementations, the content provider may group the phrases into topic sub-categories of different categories, which are shown by the listing 222b in the settings interface 210. The content provider may create new topic categories and sub-categories using the button 224.

A topic category may be selected by clicking on the name of the category, upon which all the phrases that have been created for that particular category are shown in the panel 214. Any new phrase that is configured using the input field 212 is added to the selected category.

For example, the cellular service provider may specify two topic categories "Dissatisfaction" and "Escalation," and may have selected the "Dissatisfaction" category as shown in FIG. 2C. In the "Dissatisfaction" category, the cellular service provider may include phrases that are indicative of a customer's dissatisfaction with the service provided by the cellular service provider, such as the phrases, "I want to cancel my service plan" and "Your service is terrible," shown in the panel 214. If the cellular service provider now creates a new phrase, that new phrase will be grouped into the "Dissatisfaction" category.

Continuing with the above example, the cellular service provider may specify two topic sub-categories "Technical Question" and "Sales" for the "Escalation" topic category, as shown. Phrases that indicate that the customer is seeking technical help, such as "My phone is not powering on" or "I am not getting a signal," may be grouped under "Technical Question." On the other hand, phrases that indicate that the customer is a prospective subscriber, such as "I want to know about your plans" or "I would like to upgrade," may be grouped under "Sales."

After the various parameters are configured using settings interfaces as described in the preceding sections, the contact handling platform 130 analyzes customer interactions in terms of the configured parameters. In some implementations, the background processes continuously monitor the customer interactions and update the parameter values whenever conditions corresponding to the parameters are detected. For example, the STAM 134 continuously checks for a customer's speech as the customer interacts with the ARS 132, and searches for patterns in the speech that match one or more of the configured phrases.

As described previously, the parameter values are used to compute the customer experience score. In some implementations, the customer experience score may be computed continuously in the background by the ARM 136. In other implementations, the customer experience score may be computed or updated whenever instructions are encountered in an interaction page for using the customer experience score. The instructions may be configured by the content provider. For example, the content provider may include, in an interaction page, a link to the page that includes the instructions dependent on the customer experience score. Accordingly, the customer experience score is computed or updated whenever the script corresponding to this interaction page is executed as part of the interaction flow for the site.

In some implementations, the content provider may include, in every interaction page, a link to the page that includes the instructions dependent on the customer experience score. In such implementations, the customer experience score is computed or updated after every interaction between the customer and the contact handling platform 130.

Figure 2D:
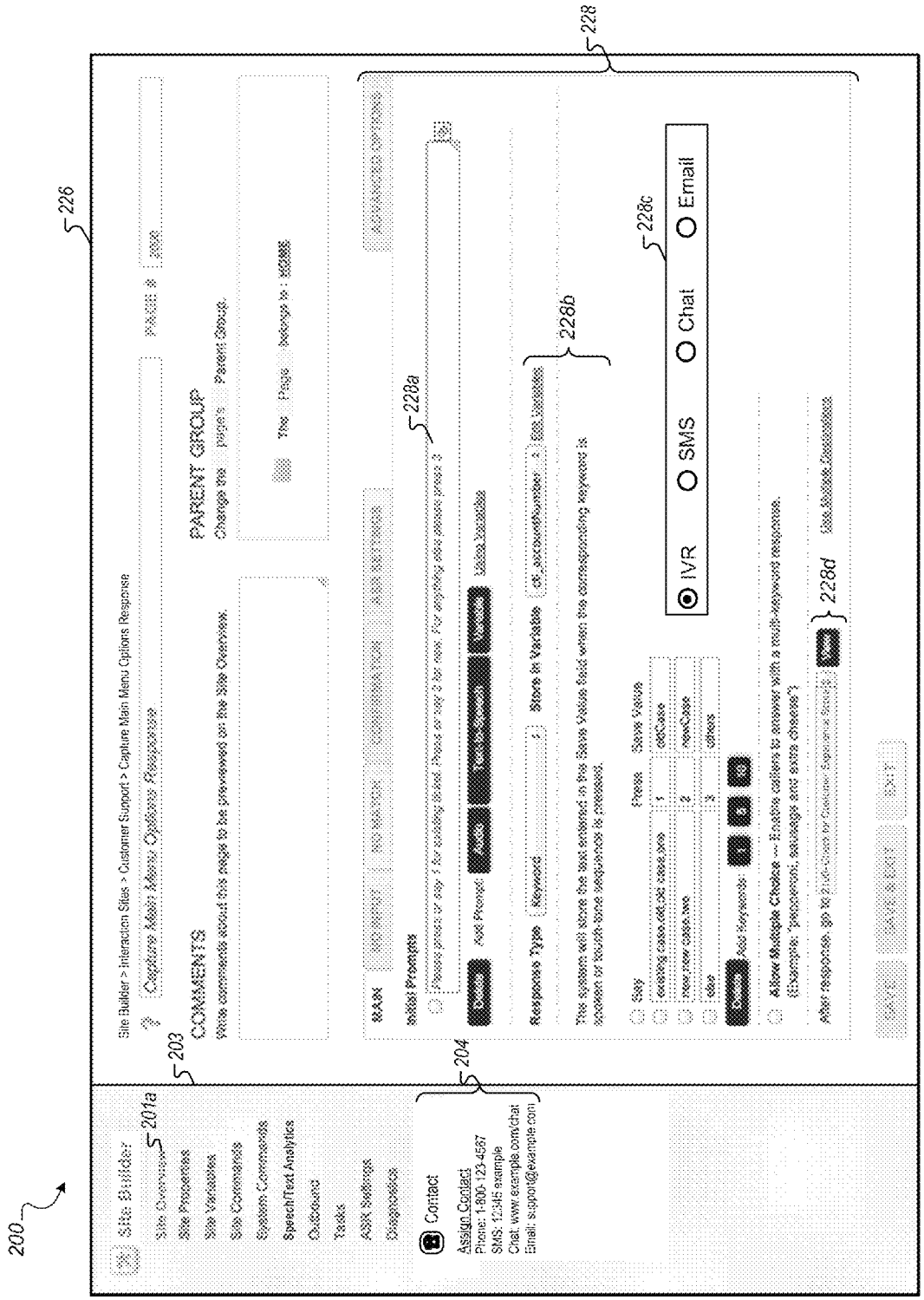

FIG. 2D illustrates an example GUI 200 showing an interaction page 226, titled "Capture Main Menu Options Response" and assigned page number 2000, which includes a link to a page that includes the instructions for routing based on the customer experience score. The interaction page 226 may be accessed by the content provider from the "Site Overview" page 201, by clicking on the link shown in the Page Name field 201d that is part of the page flow 202. For example, the content provider may click on the "Capture Main Menu Options Response" page name in the page flow 202 to access the interaction page 226.

The interaction page 226 includes various information and instructions 228 that are implemented when the script or, more generally, programming language module corresponding to the page 226 is executed as part of the interaction flow for the "Customer Support" interaction site. For example, when the interaction flow implements the instructions 228, the ARS 132 may prompt the customer with the phrase "Please press or say 1 for existing ticket. Press or say 2 for new. For anything else please press 3." The content provider may configure this phrase by inputting the phrase (e.g., by directly typing in the phrase) into an instruction field 228a. The instructions also indicate, as shown by the instruction field 228b, that the response expected from the customer is a keyword, which may be deduced either from the customer's speech or from the touch-tone sequence that is pressed on the customer's communications device.

In some implementations, the interaction page 226 includes a group of radio buttons 228c, which allows the content provider to select a specific communications mode for configuration. The communications modes listed in the group 220 correspond to the enabled communications modes that are supported for the interaction site. As shown, IVR is selected in the group 228c, which indicates that the GUI 200 allows the content provider to input parameters that configure the interaction page 226 for the voice communications mode.

In addition to the above, the instructions 228 may specify that, after the customer response, the interaction flow should jump to page "2100—Check for Customer Experience Score," as shown by the instruction field 228d. As described in greater detail below, the page "2100—Check for Customer Experience Score" includes instructions for routing based on the customer experience score. Accordingly, when the interaction flow reaches the end of the instructions 228, the contact handling platform 130 (specifically, the ARM 136) computes the customer experience score, upon executing the instructions specified in the page "2100—Check for Customer Experience Score." In this manner, the customer experience score may be computed or updated during an interaction flow whenever a link to the page that includes the instructions using the customer experience score is encountered while executing the scripts or programming language modules corresponding to the interaction pages.

Figure 2E:
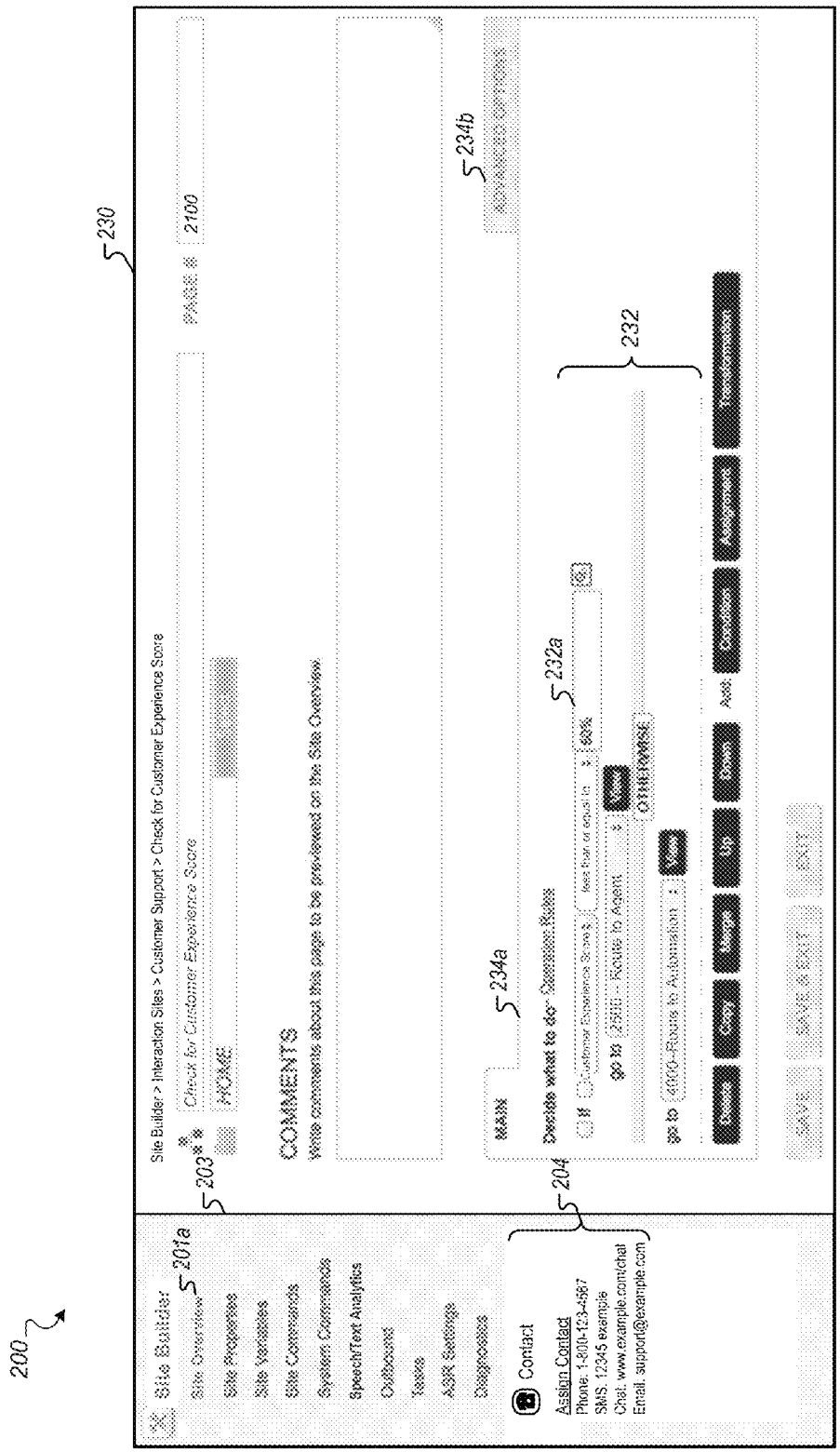

FIG. 2E illustrates an example GUI 200 showing the interaction page 230, titled "Check for Customer Experience Score" and assigned page number 2100, which includes the instructions for routing the interaction flow based on the customer experience score. During site generation, the content provider may access the page 230 from the "Site Overview" page 201, by clicking on the link shown in the Page Name field 201d that is part of the page flow 202. For example, the content provider may click on the "Check for Customer Experience Score" page name in the page flow 202 to access the interaction page 230.

The interaction page 230 includes instructions 232, shown in the "Main" tab 234a, which are implemented when the script corresponding to the page 230 is executed as part of the interaction flow for the "Customer Support" interaction site. For example, after executing the script corresponding to the interaction page 226, the interaction flow executes the instructions 232 in page 230, since the instructions in page 226 include a link to the page 230, as described previously.

As shown, the content provider may configure the instructions 232 to compare the customer experience score to a threshold value of 60%, which is specified by the input field 232a. The threshold value provides a measure of the customer's level of satisfaction in communicating with the interaction site. In implementations where the customer experience score is computed as a percentage, as described with reference to the settings interface 206, higher values of the customer experience score indicate greater customer satisfaction in interacting with the ARS 132. In such implementations, the threshold value indicates a lower limit such that when a customer's experience score reaches or falls below that lower limit, the customer's level of satisfaction in interacting with the ARS 132 is deemed to have fallen so low that the communications session should be routed to a human agent, who may be able to handle the customer's requirements better and consequently increase his or her level of satisfaction. On the other hand, if the customer experience score is above the threshold, then it indicates that the customer's level of satisfaction in interacting with the ARS 132 is sufficiently good that the communications session may be continued with the ARS 132.

The threshold value is configured by the content provider by inputting (e.g., typing in) an intended value into the input field 232a. In some implementations, the contact handling platform 130 may provide a default threshold value that may be modified by the content provider. The content provider may configure a particular value for the threshold based on various factors, which may include its own analysis of the requirements for its customers, the economic incentive that it may have in keeping customers satisfied versus the tradeoff in the cost involved in hiring more agents. For example, the content provider may configure a high value for the threshold in the page 230, such as 80%, if it wants to route a customer communications to a human agent relatively quickly, as compared to the case where the threshold is configured to be 60%. This may be the case because, starting at a default customer experience score of 100% for a customer communications session, as described with reference to the settings interface 206, a fewer number of conditions corresponding to configured parameters need to be measured to reach the 80% threshold, compared to the number of conditions corresponding to the configured parameters to reach the 60% threshold.

However, a high value of the threshold may also mean that more customer communications will be routed to human agents. Therefore, the content provider may have to hire more agents, which would typically be more expensive compared to using the ARS 132.

As described previously, in some implementations, when the interaction flow executes the instructions 232 during a customer communications, the contact handling platform 130 updates the value of the customer experience score and compares the updated value to the configured threshold. If the customer experience score is greater than the threshold, then it indicates that the customer's level of satisfaction in interacting with the ARS 132 is sufficiently good such that the communications session may be routed back to the automated system, which is indicated by the instruction "go to '4000—Route to Automation'." The page "4000—Route to Automation" may provide instructions for continuing the interaction using the ARS 132.

On the other hand, if the customer experience score is below the threshold, then the customer's satisfaction level in interacting with the ARS 132 is so low that the interaction flow should route the communications session to a human agent, which is indicated by the instruction "go to '2500—Route to Agent'." As described in greater detail below, the page "Route to Agent", which has been assigned page number 2500, provides instructions for connecting the customer to a human agent.

Figure 2F:
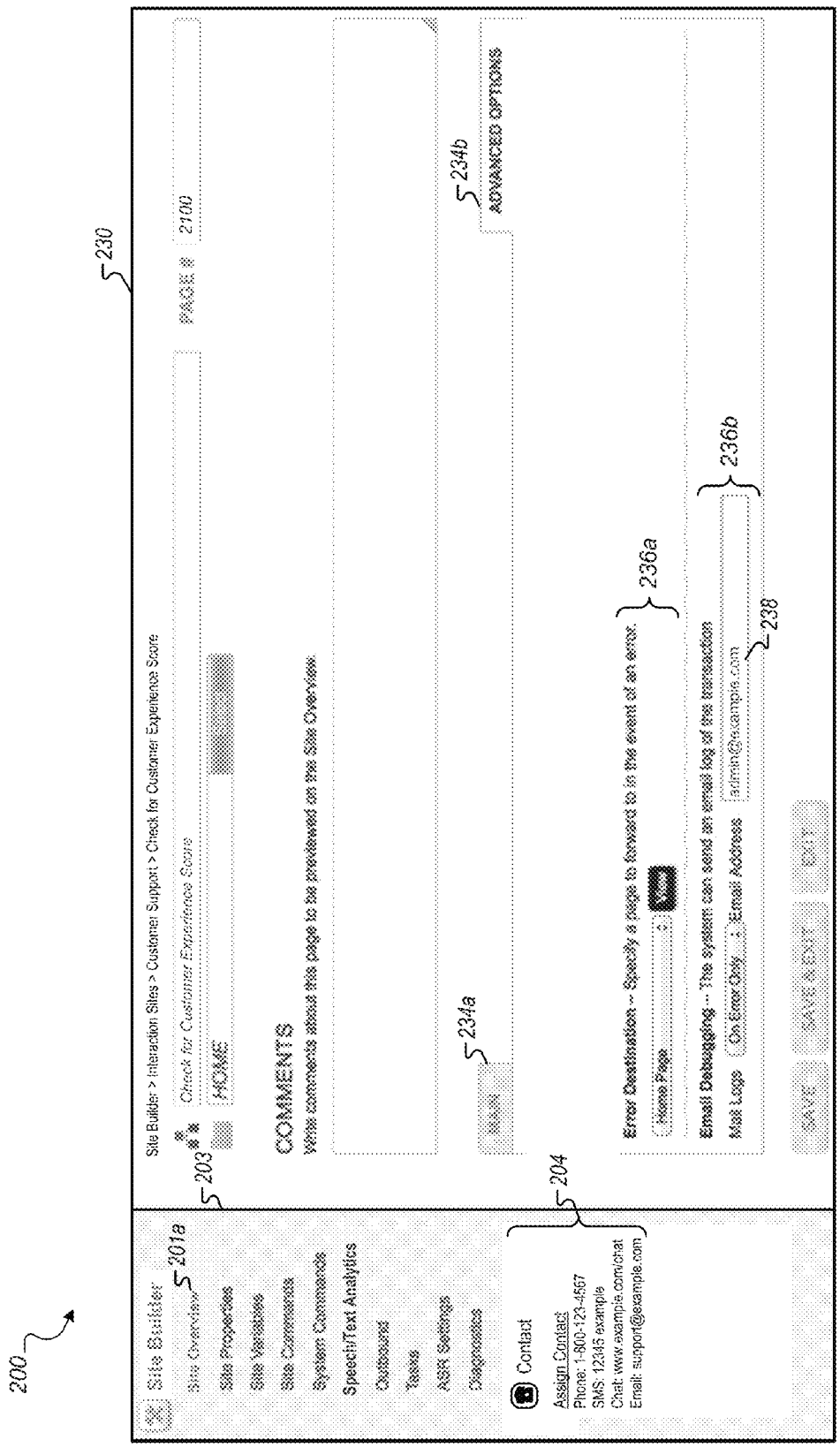

In some implementations, the page 230 may include instructions for handling error conditions. This may be useful if the interaction flow runs into an error while trying to route the call to a human agent, for example, if the application is unable to execute the scripts or programming language modules described by the page 2500 (which may be the case if the page is corrupted for some reason), or if a human agent is not available at that particular time to accept the customer communications session. FIG. 2F shows instructions 236a and 236b provided by the interaction page 230 for handling the interaction flow in case of an error condition.

The content provider may configure the instructions 236a and 236b by selecting the "Advanced Options" tab 234b in the page 230. As shown, the content provider may configure the instructions 236a to specify that upon encountering an error condition, the interaction flow should move to the "Home Page," which is the interaction page "Say Greeting" assigned page number 1000, as specified by 201c in the "Site Overview" page 201. Accordingly, in the event that the interaction flow cannot connect to a human agent while routing based on the instructions 232, then the interaction flow will return to the first page in the interaction flow. Consequently, the customer will re-hear, from the ARS 132, the greeting specified in the interaction page 1000.

In some implementations, the content provider also may configure the instructions 236b such that the contact handling platform 130 will send an email to the email address "admin@example.com," which is specified by the content provider in the field 238. As shown, the content provider may configure the instructions 236b to send an email log of the transaction "on error only." Therefore, a transaction log will be sent to the email address specified only if the interaction flow cannot connect to a human agent while routing based on the instructions 232.

Figure 2G:
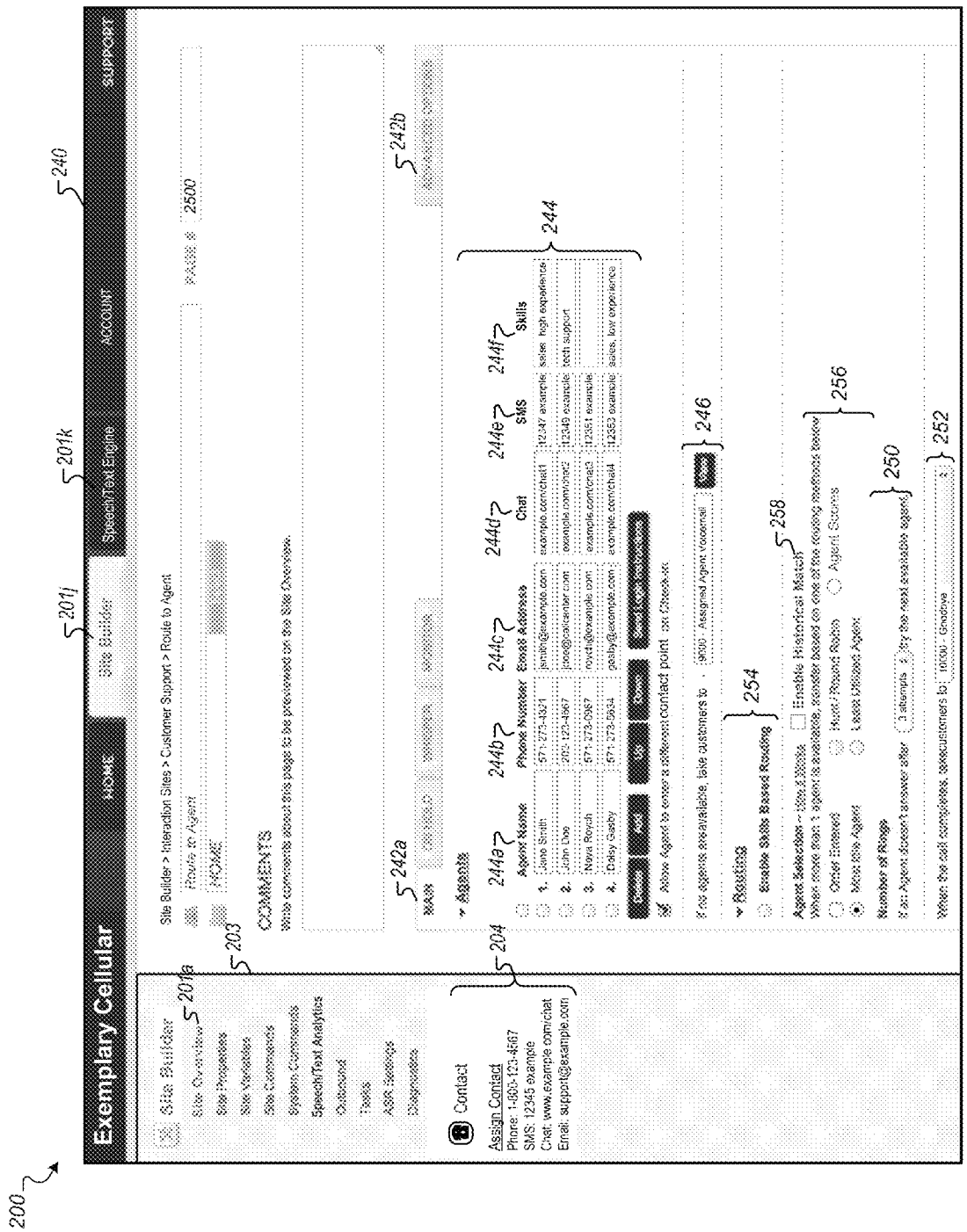

In the normal operation of the interaction site (i.e., no error is encountered), when the customer experience score is below the specified threshold during execution of the instructions 232, the interaction flow processes the instructions specified in the page 2500. FIG. 2G illustrates an example GUI 200 showing the interaction page 240, titled "Route to Agent" and assigned page number 2500, which includes the instructions for routing the customer communications to an agent. During site generation, the content provider may access the page 240 from the "Site Overview" page 201, by clicking on the link shown in the Page Name field 201*d* that is part of the page flow 202. For example, the content provider may click on the "Route to Agent" page name in the page flow 202 to access the interaction page 240.

In the example shown, the interaction page 240 is generated by the cellular service provider as the content provider for routing the communications of its customers who contact the company's "Customer Support" interaction site. The interaction page 240 includes a list of agents 244, shown in the "Main" tab 242*a*. Each agent in the list 244 includes an agent name 244*a*, and a contact point corresponding to each communications mode supported by the interaction site. As discussed previously, the interaction site may support telephone, SMS, email and web chat communications modes. Therefore, for each agent in the list 244 there is a phone number 244*b*, an email address 244*c*, a web chat contact 244*d* and an SMS 244*e*. In addition, some of the agents have skills 244*f* assigned to them, which are used when skills-based routing is enabled, which is described in greater detail below.

In some implementations, the content provider, i.e., the cellular service provider in the present example, configures the names and contact information of the agents in the list 244. The agents may be employees of the cellular service provider, or they may be associated with contractors hired by the cellular service provider to provide support services. The agents may be located in the same location, e.g., in an office associated with the cellular service provider, or they may be located in different places, e.g., in different contact centers, as described previously.

In some implementations, at the time that a customer communications is routed to the page 2500, none of the agents in the list may be available to connect to the customer. This may be the case, for example, when the agents are all on a break (e.g., lunch hour), or all the agents who are on duty are engaged in answering other customer communications. To handle such situations, the content provider may configure instructions 246, which specifies the action to take when no agent is available. For example, the cellular service provider may specify that if agents are not available, then the application should send the customer communications to page 9000, titled "Assigned Agent Voicemail." The page 9000 may include instructions that to connect the customer communications to an agent's voicemail, such that the customer may leave a message. Additionally or alternatively, the page 9000 may include other instructions to connect the customer communications to other agent contact points that are associated with the different communications modes implemented by the interaction site (e.g., an e-mail address).

In some implementations, the default strategy on page 240 for connecting customer communications to agents may be that an incoming customer communications is sent to the first available agent. In such implementations, the customer communications may be sent to an incoming communications queue, and available agents are included in an agent queue. The first customer communications from the head of the communications queue may be connected to the first agent from the head of the agent queue.

The content provider may configure instructions 250, specifying that if the agent selected for a customer communications does not accept the connection after a number of attempts, then the customer communications should be connected to the next agent from the agent queue. The number of attempts may be a configurable parameter that is specified by the content provider.

The content provider also may configure instructions 252 that specify how the interaction flow should proceed once the communications between a customer and an agent is completed. For example, the cellular service provider may specify that the interaction flow should proceed to the page 10000, titled "Goodbye." The page 10000 may include instructions to end call, with the application (e.g., the ARS 132) sending a greeting to the customer. Additionally or alternatively, the page 10000 may include instructions for the application (e.g., the ARS 132) to query the customer to answer a survey regarding the recent communications session.

In some implementations, the content provider may specify a skills-based routing strategy. This may be enabled through the instructions 254, e.g., when the content provider selects the "Enable Skills Based Routing" option. When the skills-based routing strategy is used, the customer communications are not connected to available agents using the default strategy described above. Instead, the application matches customer communications to the most suitable agents for handling the communications, based on one or more factors such as the subject matter of the customer communications, agent characteristics such as agent skills or agent scores, and past history of interactions between the customer and the agents, among others.

For example, when a customer communicates with the "Customer Support" interaction site, the contact handling platform 130 may determine the reason or subject matter for the call, or certain characteristics of the customer, or both, apart from computing the customer experience score. The contact handling platform may make the determinations by analyze the customer's interactions with the ARS 132, or the STAM 134, or both. If a cellular subscriber calls in to the interaction site and says, while interacting with the ARS 132, that "My phone is not working," then the STAM 134 may determine, using speech recognition techniques, that the customer needs technical support. In another case, if the customer calls in and says "I want to upgrade my plan," then the STAM 134 may determine that the customer is seeking sales support. In some implementations, the STAM 134 may determine, using speech recognition techniques, that the customer has a non-native accent, or that the customer is elderly, or some such characteristic. This information may be forwarded to the ARM 136 for selecting the most suitable agent for the particular type of customer communications, or for the specific customer, or both.

Upon receiving the information on the type of the communications, or the characteristics of the customer, or both, the ARM 136 may attempt to match the customer communications to the most suitable agent. In some implementations, the ARM 136 may use the agent skills 244*f* that are configured by the content provider. For example, the cellular service provider may specify that agent "John Doe" has "tech support" skills, indicating that the particular agent has expertise in handling customer communications for which the subject matter are related to technical support issues. The cellular service provider also may specify that agents "Jane Smith" and "Daisy Gasby" have "sales" skills, indicating that the particular agents have expertise in handling customer communications for which the subject matter are related to sales. Accordingly, the ARM 136 may match the customer who needs technical support to agent "John Doe," and the customer who is seeking sales support to the first available agent between "Jane Smith" and "Daisy Gasby." If the matched agent is not available to take the call, then the ARM 136 attempts to connect to the next agent available with the required skills.

The cellular service provider may specify other skills, such as "high experience" and "low experience," which indicate that the corresponding agents have high expertise and limited expertise, respectively, in handling customer communications. Accordingly, when the ARM 136 tries to find a match for a customer who is extremely dissatisfied (indicated, for example, by a very low customer experience score for the associated customer communications), then the ARM 136 may try to find an agent who has high expertise in dealing with customer communications (e.g., agent "Jane Smith"), but try to avoid an agent who has limited expertise in dealing with customer communications (e.g., agent "Daisy Gasby"). This may be because an agent with low experience may get more easily flustered when dealing with a unhappy or angry customer as compared to an agent who has high experience and may have handled many situations like this before.

In some implementations, the contact handling platform 130 determines the satisfaction level of the customer, or the performance of the agent, or both, based on the interaction between the customer and the agent during a communications session. In this manner, the contact handling platform 130 may compute additional metrics that are used for matching customers to agents.

In some implementations, one of the additional metrics may be a second customer experience score, which is a measure of the customer's level of satisfaction in interacting with a human agent. In some implementations, the second customer experience score may be a numerical value, while in other implementations the second customer experience score may be one of several levels, such as "high," "medium," or "low". The second customer experience score may be different from the customer experience score described previously with respect to the page 230. The latter is computed based on the customer's interaction with the ARS 132.

In some implementations, one of the additional metrics may be an agent score, which is a measure of the performance of the agent in handling customer communications. For a particular agent, the agent score may be an aggregate of the second customer experience scores computed for the customer communications handled by the agent. This may be the case because the second customer experience scores provide an indication of how well or poorly the agent can handle different types of customers and various types of communications situations. In some implementations, the agent score may be a numerical value, such as when the agent score is computed using numerical values for the second customer experience score. In other implementations, the second customer experience score may be one of several levels, such as "high," "medium," or "low," for example when the second customer experience scores are based on such levels.

Additionally, or alternatively, the agent score may be based on tracking the agent's behavior during customer communications. For example, the system may measure how composed the agent remains in handling difficult customers or whether the agent gets easily flustered; how well the agent is able to calm an agitated customer; or how quickly the agent is able to resolve the customer's issues.

To compute the additional metrics, the STAM 134 may perform speech recognition on the customer's speech as he or she interacts with the agent at issue during a session, to determine the level of satisfaction of the customer in interacting with the agent. For example, if the customer utters keywords or phrases with a positive connotation, such as "Awesome," "Thank you so much," or "Thank you for helping," then the STAM 134 will interpret the customer's speech as indicating a high level of satisfaction of the customer in interacting with the agent. This information may be passed to the ARM 136, which will accordingly measure the second customer experience score as high. On the other hand, if the customer utters keywords or phrases with a negative connotation, such as "Terrible," "This is a waste of time," or "You are not helping," then the STAM 134 will interpret the customer's speech as indicating a low level of satisfaction of the customer in interacting with the agent. In such cases, the ARM 136 will give measure the second customer experience score as low.

Additionally or alternatively, in some implementations, the customer's satisfaction level may be computed using customer feedback after the customer-agent interaction is over. For example, the customer may complete a survey to indicate his or her satisfaction with the session and the particular interaction with the agent. This survey may be processed by the ARM 136 in determining the second customer experience score.

For each customer, the ARM 136 may store the second customer experience scores for future use in matching the customer with agents, as described in greater detail below. Additionally or alternatively, the ARM 136 may use the second customer experience score for each customer communications to update the agent score for the agent that handled the particular customer communications.

In some implementations, the agent skills 244f configured by the content provider are mapped to the agent scores, or to specific keywords detected in the customer's input, or both. The mapping may be a default mapping provided by the contact handling platform 130, or it may be configured by the content provider. For example, the content provider may configure the skill "high experience" as mapping to an agent score above 67 (on a scale of 1-100, when the agent scores are numerical values), or to a "high" level (when the agent scores are level-based); and the content provider may configure the skill "low experience" as mapping to an agent score below 33 (on a scale of 1-100, when the agent scores are numerical values), or to a "low" level (when the agent scores are level-based). The content provider, i.e., the cellular service provider, may configure the skill "sales" as being a direct match for customer communications associated with the customer's speech in which one or more of the keywords or phrases such as "upgrade," "plan," "sales," or "new phone" are detected. Similarly, the cellular service provider may configure the skill "tech support" as being a hit for customer communications associated with the customer's speech in which one or more of the keywords or phrases such as "phone not working," "signal," or "no connection" are detected.

In some implementations, the content provider may select one of several options for matching customers to agents using the instructions 256. The selected option may be used, for example, when skills-based routing is enabled. The content provider may select an option by clicking on the radio button next to the option. As shown, the options include "Order Entered," "Most Idle Agent," "Hunt/Round Robin," "Least Utilized Agent" and "Agent Scores."

When the "Order Entered" option is selected, the customer communications is matched based on the order the agents are specified by the list 244. The contact handling platform identifies the first agent in the list 244, e.g., "Jane Smith" and selects this agent for routing the customer communications. If agent "Jane Smith" is not available (e.g., the agent is presently handling a customer communications or is away), then the contact handling platform checks whether the next agent specified in the list (e.g., "John Doe") is available, and then the next, and so on.

When the "Most Idle Agent" option is selected, the customer communications is matched to an agent who has not handled a customer session for the longest period, among all the available agents. In some implementations, the contact handling platform may log the times when agents interact with customers. In this manner, the system may have knowledge of when was the last time an agent was engaged in communications with a customer and, accordingly, may compute use this knowledge to compute the idle times for the agents. The contact handling platform may arrange the available agents in an order of decreasing idle times, and match an incoming customer communications to the first agent in the arrangement, i.e., the agent who has been idle for the longest period among the available agents.

When the "Hunt/Round Robin" option is selected, the customer communications is matched to agents using a Round Robin scheduling scheme. In such cases, the contact handling platform schedules the agents as they become available (e.g., in a queue), and selects first available agent from the schedule. If the first agent in the list is not available (e.g., the agent is presently handling a customer communications or is away), then the contact handling platform checks whether the next scheduled agent is available, and then the next, and so on.

When the "Least Utilized Agent" option is selected, the customer communications is matched to an agent who has handled the least number of customer sessions, among all the available agents. In some implementations, the contact handling platform may track how many customer interactions have been handled by each agent. The contact handling platform may arrange the available agents in an order of increasing number of customer interactions handled, and match an incoming customer communications to the first agent in the arrangement, i.e., the agent who has handled the least number of customer sessions among the available agents.

When the "Agent Scores" option is selected, the customer communications is matched to an agent based on the agent scores, which are computed as described in the preceding sections. In some implementations, the contact handling platform arranges the available agents in an order based on the agent scores, e.g., starting with the agent with the highest agent score and ending with the agent with the lowest agent score. The contact handling platform may match an incoming customer communications to the first agent in the arrangement, i.e., the agent who has highest score among the available agents.

In some implementations, the content provider may connect customer communications to agents based on historical match, using the instructions 258. Historical match may be used, for example, when skills-based routing is enabled. The content provider may select the historical match option by clicking on the check box next to "Enable Historical Match" 258.

When historical match is enabled, the contact handling platform looks at past history of a customer's interaction with the different agents in selecting agents for connecting to the customer's present communications session. The contact handling platform may check the past history of the customer's interactions by examining the second customer experience scores of the customer that are stored by the system, e.g., in the data store 138. As described previously, the second customer experience scores may be computed and stored by the ARM 136. In some implementations, the second customer experience scores may be stored along with the customer's contact point information (for the different communications modes). This may be useful when the customer calls at a later point in time using one of the contact points corresponding to which information have been stored. Then the associated second customer experience scores may be retrieved from storage based on the contact point information that is obtained from the present communications session.

The customer's contact point information may include, for example, a phone number corresponding to the customer's voice communications device if the customer communications was made using voice communications mode, or using SMS where the message is sent from the customer's voice communications device. Alternatively or additionally, the contact point information may be the customer's email address, if the customer communications was partly or fully via email messages. The contact point information also may be the customer's online account name (and potentially other information such as contact email address, telephone number, postal mailing address or any suitable combination of these) if the customer communications was made via web chat through a web portal for the interaction site.

In some implementations, the ARM 136 arranges the available agents in an order based on the second customer experience scores for the particular customer for these agents that are retrieved from storage. For example, the ARM 136 may arrange the agents in an order of decreasing second customer experience scores, e.g., starting with the agent corresponding to whom the customer has the highest second customer experience score and ending with the agent with the lowest corresponding to whom the customer has the highest second customer experience score. The contact handling platform may match the associated present customer communications to the first agent in the arrangement, i.e., the agent corresponding to whom the customer's second experience score is highest among the available agents. This matching may be based on the premise that the customer is more likely to have a high satisfaction level by dealing with an agent with whom the customer has had a positive experience in the past, compared to an agent with whom the customer had a less positive, or negative, experience in the past.

Figure 2H:
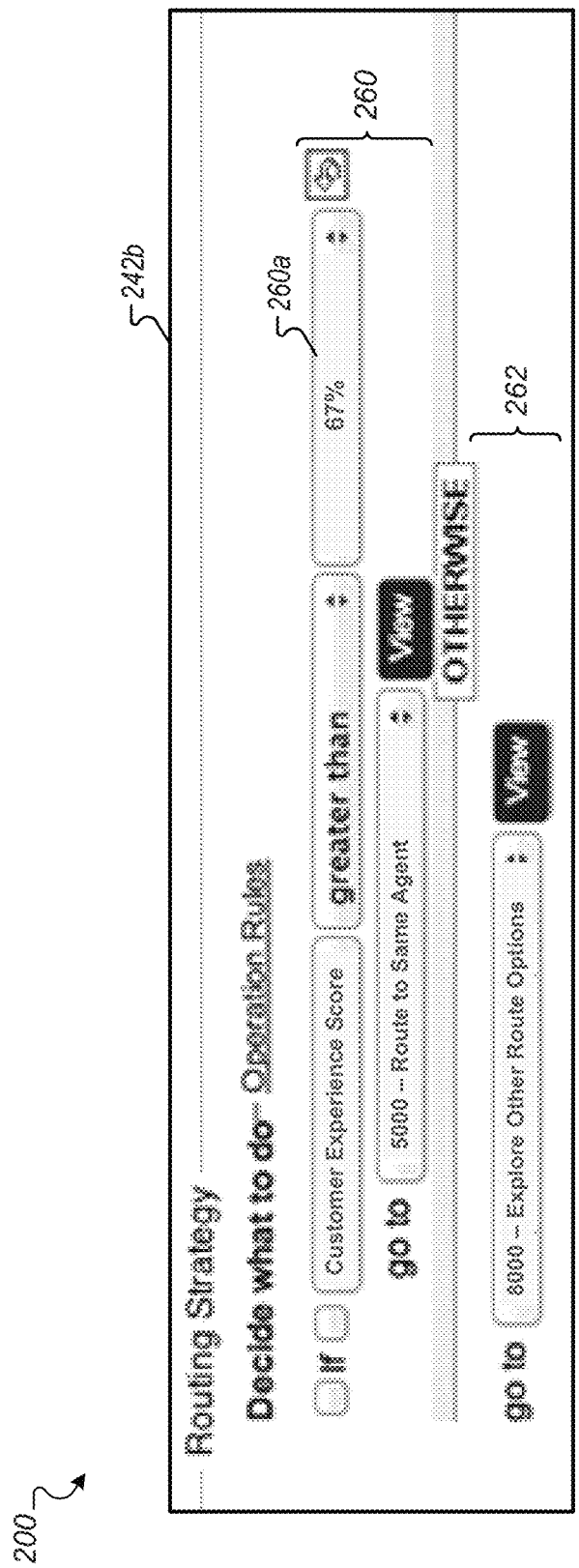

In some implementations, the content provider may specify advanced options for agent selection when historical matching is enabled. FIG. 2H shows instructions 260 and 262 that are configured by the content provider as advanced options for historical match. The content provider may configure the instructions 260 and 262 by selecting the "Advanced Options" tab 242b in the page 240.

In some implementations, the content provider may use the advanced options to specify that an agent may be selected for the customer communications only if the second customer experience score of the customer corresponding to that agent is greater than a certain threshold 260a, e.g., 67%, as shown by the instructions 260. In such a case, when seeking agents based on the customer's corresponding second customer experience scores, the ARM 136 will select only those agents corresponding to whom the customer's second customer experience score is at least 67%.

In some implementations, the ARM 136 will route the customer communications to the first available agent it determines who matches the criterion specified by instructions 260. In these cases, the ARM 136 may not look for other available agents who also may fit the criterion. Therefore, the ARM may route the customer communications quickly, but potentially at the cost of missing an agent who may be more suited to handle the customer communications, e.g., an agent with a higher second customer experience score than that of the selected agent (though both these agents have second customer experience scores above the configured threshold 260a).

In other implementations, the ARM 136 will arrange the agents in an order of decreasing second customer experience scores, similar to that described previously. However, in these cases, the ARM 136 will include only those agents in the arrangement corresponding to whom the customer's second customer experience scores are greater than the threshold 260a. Then the ARM 136 may match the associated present customer communications to the first agent in the arrangement, i.e., the agent corresponding to whom the customer's second customer experience score is highest among the available agents and the second customer experience score is above the threshold 260a configured in instructions 260.

In some implementations, if the ARM 136 determines that no suitable agent is available for routing the customer communications based on the instructions 260, then the ARM 136 will attempt to route the communications based on the instructions 262. In such an event, the interaction flow will move to page 8000, titled "Explore Other Route Options." In such implementations, the content provider may configure the instructions in page 8000 to specify other strategies for routing the customer communications, e.g., select agents based on historical match even if the second customer experience scores are below the threshold 260a; select agents based on order entered, most idle agent, hunt/round robin, least utilized agent, and/or agent scores; and/or send the customer communications to voicemail.

In some other implementations, if the ARM 136 determines that no suitable agent is available for routing the customer communications based on the instructions 260, then the ARM 136 will attempt to route the communications based on the instructions 256. This may be the case, for example, when instructions 262 are not configured, such that when no agents are selected due to the second customer experience scores being less than the threshold 260a, the routing strategy reverts to the options configured in page 240. In such implementations, the content provider may select one of the options from instructions 256, such as select agents based on order entered, most idle agent, hunt/round robin, least utilized agent, or agent scores. The content provider also may configure, e.g., using instructions 246, that if no agents are available, then send the customer communications to voicemail.

Although the above section describes that the ARM 136 performs historical matching based on the instructions 258 and 260 using the agent-specific second customer experience scores, in some implementations the ARM 136 may perform the historical matching using aggregate customer experience scores. This may be the case, for example, when the contact handling platform 130 does not use separate agent-specific customer experience scores for the customer's interactions with the ARS 132 and the agents. Instead, the contact handling platform 130 may compute an overall customer experience score for the customer that includes the customer's satisfaction level based on interactions with the ARM, or with any agent, or with both.

In some implementations, the threshold 260a may be precomputed by the contact handling platform 130. In other implementations, the threshold may be configured by the content provider. It is to be noted that the threshold 260a is distinct from the threshold 232a. The threshold 232a is used by the ARM 136 to make the determination whether to route a customer communications from the ARS 132 to a human agent. On the other hand, the threshold 260a is used by the ARM 136 to determine which of the available agents is suitable for connecting the customer communications. Therefore, threshold 260a is used by the ARM 136 only after a determination is made using the threshold 232a to route the customer communications to a human agent.

In some implementations, historical match may be used in conjunction with one of the options configured by the content provider using the instructions 256. In such implementations, the ARM 136 may initially select the agents based on past interactions between the customer and the agents. If the content provider specifies advance options for the historical match using the instructions 260, then the ARM may shortlist only those agents corresponding to whom the customer's second experience scores are above the threshold 260a. After agents are shortlist based on past interactions between the customer and the agents, the ARM 136 may use the agent selection option specified by the content provider using instructions 256 to arrange the shortlisted agents in an order as described previously, and then connect the customer communications to an agent suitably selected from the arrangement.

As an illustrative example, 10 agents may be active in the contact centers 140 and 150 to handle customer communications for the "Customer Support" interaction site. Of these 10 agents, 6 agents have skill "sales," i.e., they have the expertise to handle a customer communications that is sales-related. Accordingly, the 6 agents are initially shortlisted for handling the customer communications. Out of these shortlisted agents, 4 agents have had a positive experience with the customer in the past. Accordingly, the customer's second experience scores corresponding to these 4 agents is above the 67% threshold configured using instructions 260. The customer's second experience scores corresponding to the other 2 agents in the shortlist is below the 67% threshold and consequently, these two agents are removed from consideration for handling the customer communications. Of the 4 agents remaining in the shortlist, a single agent is selected to handle the customer communications in accordance with the instructions 256 (e.g., the most idle agent of the 4 is selected, the least utilized agent of the 4 is selected, or the agent with the highest agent score of the 4 is selected).

Figure 3:
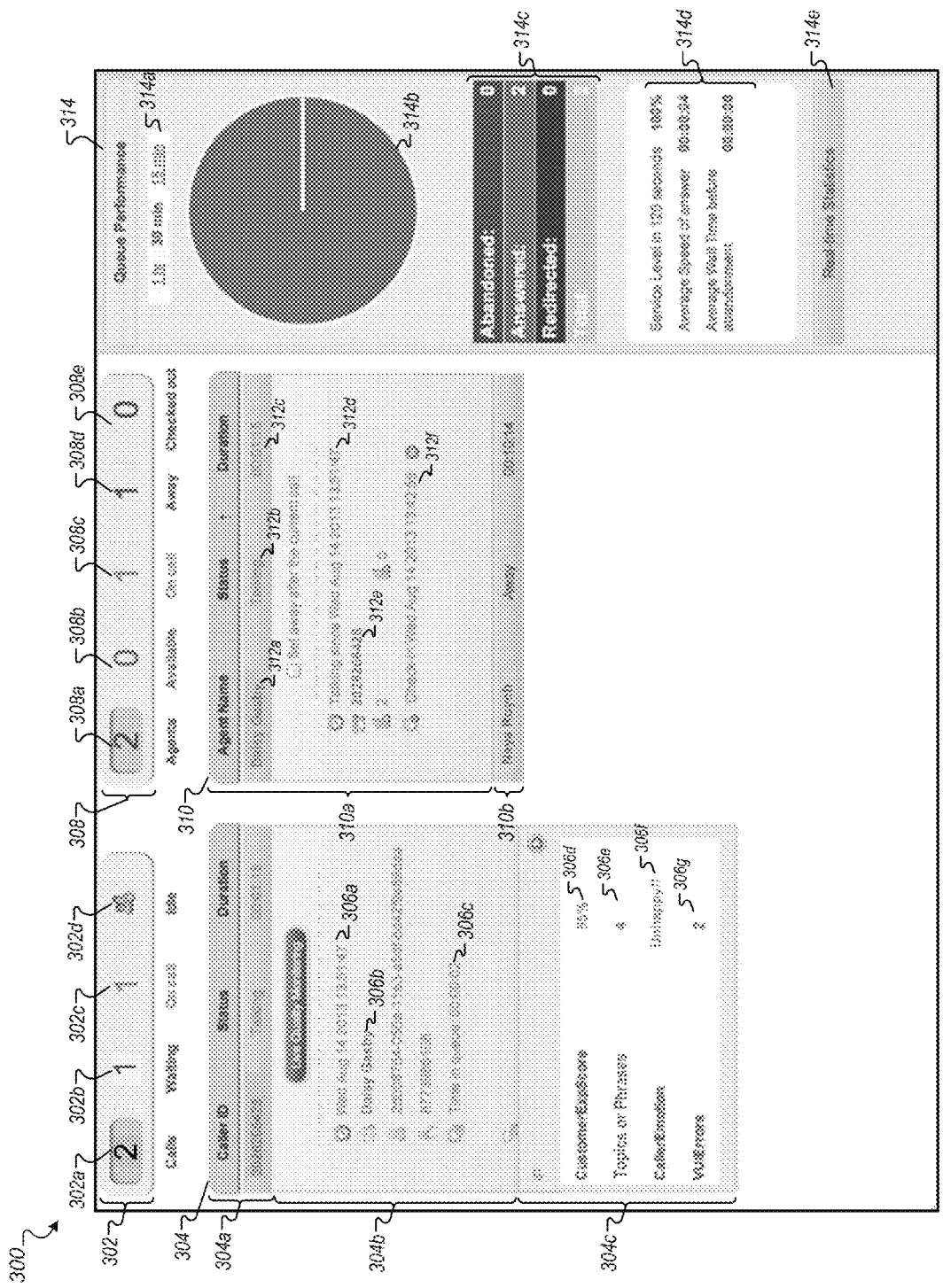
FIG. 3 illustrates an example GUI that is shown to a human agent when customer communications are routed to the agent.

In some implementations, when the ARM 136 selects an agent for handling a customer communications, the information on the communications session is forwarded to the agent's contact point. The information may be displayed to the selected agent, for example, on a computer display coupled to the device used by the agent in answering customer communications. FIG. 3 illustrates an example GUI 300 that is shown to a human agent when customer communications are routed to the agent. The agent may be handling customer communications for an interaction site hosted by the contact handling platform 130. The GUI 300 may be displayed by an application running on a computing device associated with the agent that is connected to the contact handling platform 130, and the application may be displaying information provided by the contact handling platform 130. For example, the application displaying the GUI 300 may be a client application that shows information provided by a server running on the contact handling platform 130, which manages information sent to various agents for the interaction site hosted by the contact handling platform. In some implementations, the GUI 300 may be shown on a web browser running on the agent's computing device. Accordingly, the following sections describe the GUI 300 with respect to the communications system 100. As a specific example, the components of the GUI 300 are described as used by an agent answering customer communications for the interaction site "Customer Support" that is associated with the cellular service provider. However, in other implementations the GUI 300 may be associated with other interaction sites hosted by other platforms or systems.

As shown, the GUI 300 provides information associated with the voice communications mode, e.g., when the customer has called in using a voice communications device and therefore the agent is connected to the call using the voice communications mode. In other implementations, the GUI 300 may provide information for connections in other communications modes, such as SMS, web chat, or email, e.g., when the customer connects to the interaction site using one of these communications modes. In some implementations, the GUI 300 may simultaneously provide information for customer communications made in all the different supported communications modes.

In some implementations, the GUI 300 uses the panel 302 to provide information on the total number of calls 302a for the interaction site that are to be handled by agents, the number of calls that are "On Call" 302c, i.e., connected to agents, and the number of calls that are "Waiting" 302b, i.e., waiting in the call queue for agents to be available for connection. For example, as shown, there are total of two calls, one of which is connected and the other of which is waiting in the call queue. In some implementations, the number of on-duty agents in the call center who are idle is indicated by 302d. The idle agents are not answering any calls currently, nor are they engaged in any other kind of work. Therefore, new incoming calls can be routed to these idle agents.

The panel 304 provides information to the agent who is using the GUI 300 about the current call that the agent is handling. Sub-panel 304a shows the number of the customer's voice communications device (e.g., telephone number "2026266428" as shown), the status of the call (e.g., "Talking," i.e., the call is currently engaged), and the duration of the call, i.e., how long the customer and the agent have been connected. In some implementations, the status of the call may be determined by the STAM 134 by analyzing the participants' speech.

Sub-panel 304b provides miscellaneous bookkeeping information to the agent. For example, the sub-panel 304b indicates the current date and time 306a, the name of the agent 306b who is handling the call indicated by 304a, and how long the call was waiting in the call queue 306c before the call was connected to the agent.

Sub-panel 304c provides information about the customer that are relevant to the call being handled. For example, the sub-panel 304c includes a field 306d showing the customer experience score; a field 306e providing the number of topics or phrases that were detected during the customer's interaction with the ARS 132; a field 306f indicating a parameter "CallerEmotion," which is a measure of the customer's emotional state; and a field 306g showing the number of VUI errors that the customer made while interacting with the ARS 132.

The information provided by the fields 306d, 306e, 306f and 306g are measured by the STAM 134 and the ARM 136 during the customer's interaction with the ARS 132, in a manner described previously. In some implementations, CallerEmotion is a mapping of the customer experience score to a metric that may be more easy for the agent to understand, in comparison to the numerical value of the customer experience score. For example, the ARM 136 may map customer experience score above 67% to CallerEmotion "Happy" or "Satisfied," customer experience score in the range 67%-33% to CallerEmotion "Unhappy" or "Dissatisfied" and customer experience score below 33% to CallerEmotion "Angry."

The information provided by 304c may help the agent infer the customer's state of mind, so that the agent may be prepared to engage the customer with a suitable degree of care. For example, as shown the sub-panel 304c indicates that the customer with whom the agent is presently interacting has an experience score that is 55% and accordingly the customer is in an unhappy emotional state. Part of the reason for the low customer experience score may be that the customer made 2 VUI errors in interacting with the ARS 132. The customer also spoke during interacting with the ARS 132, and the customer's speech included 4 topics or phrases that were detected by the STAM 134 as matching keywords or phrases configured by the content provider. Presumably, correlating to the customer's emotional state, the topics or phrases detected in the customer's speech indicated the customer's dissatisfaction or unhappiness during the interaction with the ARS 132. Knowing this information, the agent may strive to be more patient while engaging the customer, or the agent may be conciliatory in an attempt to mollify the customer, or both. For example, the agent may start the interaction with the customer with an apology, such as by saying "I see that you were having a hard time," or "Do not worry—I will take care of your issues," or some other suitable comments.

The panel 308 provides a snapshot of all the agents who are currently on duty for answering calls from customers of the interaction site. The total number of agents who are assigned for answering calls for the interaction site is shown by the field 308a; the number of agents who are available to accept a call is shown by 308b; the number of agents who are "On call," i.e., currently engaged in calls with customers, is shown by 308c; the number of on-duty agents who are away (e.g., on a break) is shown by 308d; and the number of agents how are "Checked Out," i.e., currently off duty is indicated by 308e. For example, as shown, there are total of two agents assigned to the particular interaction site associated with the GUI 300. One of agents is connected to a caller while the other agent, even though on duty, is away. Therefore, zero agents are available to accept incoming calls and zero agents are off duty.

Panel 310 provides more detailed information about activities of the agents who are on duty. For example, sub-panel 310a shows information on one agent, such as the agent's name 312a, the status of the agent 312b (e.g., the agent is "Talking," i.e., engaged in a call), and how long the agent has been in the current status 312c. Sub-panel 304a may provide other information to the agent. For example, 312d indicates the date and time at which the agent commenced the current call engagement. The number of the caller corresponding to the current call is indicated by 312e. The time of the agent's "Check-in," i.e., the time the agent reported for duty, is shown by 312f.

There may be other sub-panels present displaying information on other agents who are on duty. For example, as shown, sub-panel 304b provides information on the second agent who is currently on duty. The sub-panel provides the agent's name, the status of the agent 312b (e.g., the agent is "Away," i.e., not engaged in a call and not available to accept new calls), and how long the agent has been in the current status.

The panel 314 shows information on the "Queue Performance" of the agent who is using the GUI 300. That is, the panel 314 provides metrics indicating the agent's performance during the current work session of the agent. As shown by 314a, the metrics can be viewed in different time interval granularities, such as 1 hour, 30 minutes or 15 minutes. The agent can select the desired time interval by clicking on the corresponding link in 314a.

The pie chart 314b provides a graphical view of the status of the customer communications that have been handled by the agent in the time interval selected in 314a. The same status is provided in textual form by the field 314c. For example, as shown, in the last 30 minute time interval (that is selected in 314a), the agent has successfully answered 2 calls, which is indicated by the "Answered" stripe in 314c. No call has been abandoned, i.e., the caller has hung up without completing the transaction, the caller disconnected while waiting for the agent to answer the call request, or the call got disconnected for some other reason. This is indicated by the "Abandoned" stripe in 314c. No call has been redirected, i.e., forwarded to a supervising agent who presumably is better suited to handle the issues raised in the call. This is indicated by the "Redirected" stripe in 314c. Therefore, as indicated by the "Total" stripe in 314c, of a total of 2 calls handled by the agent in the last 30 minute time interval, both calls were processed successfully.

The field 314d displays statistics of the agent's performance, with 314e indicating that the statistics are real-time statistics, i.e., the values are updated in real time as the agent interacts with the customers. For example, 314d indicates that the agent's "Service Level in 120 seconds" is 100%, i.e., in the last 120 seconds the agent was fully engaged in communicating with customers. 314d also indicates that the agent's "Average Speed of answer" is 4 seconds, i.e., the average time between a call request received by the agent and the call accepted by the agent is 4 seconds. The "Average Speed of answer" provides a measure of how quickly the agent answers call requests. Lower times indicate better performance of the agent. In addition, 314d indicates that the agent's "Average Wait Time before abandonment" is 0 seconds, i.e., no call handled by the agent was abandoned.

In this manner, as described in the preceding sections, a content provider may easily design an interaction site by using the GUI 200 that is accessed using the application builder 170. While designing the interaction site, the content provider specified instructions and parameters for measuring the satisfaction levels of customers when they interact with the site, and for routing the customer communications to live agents if the satisfaction levels fall below thresholds specified by the content provider.

The interaction site is hosted by the contact handling platform 130 who processes the customer communications and determines, upon processing the content provider-configured instructions, whether to route the communications to agents, e.g., in the call centers 140, or 150, or both. When the customer communications are routed to the agents, the contact handling platform provides information on the customer communications to the agents via the GUI 300 such that the agents are empowered to handle the customer communications with the suitable amount of care.

The systems and processes described in the preceding sections may allow a content provider to design a site that leads to increased customer satisfaction. For example, based on the routing strategies specified by the instructions, customer communications may be handled by agents when a customer is having difficulty with the automated response system. In addition, the customer communications may be routed to the agent who is most suitable for handling the particular situation, thereby leading to a satisfied customer.

The systems and processes also may lead to increased agent satisfaction. By ensuring that an agent is provided with information on a customer's satisfaction level, or emotional state, or both, agents can be ready to engage the customer with the right frame of mind.

Figure 4:
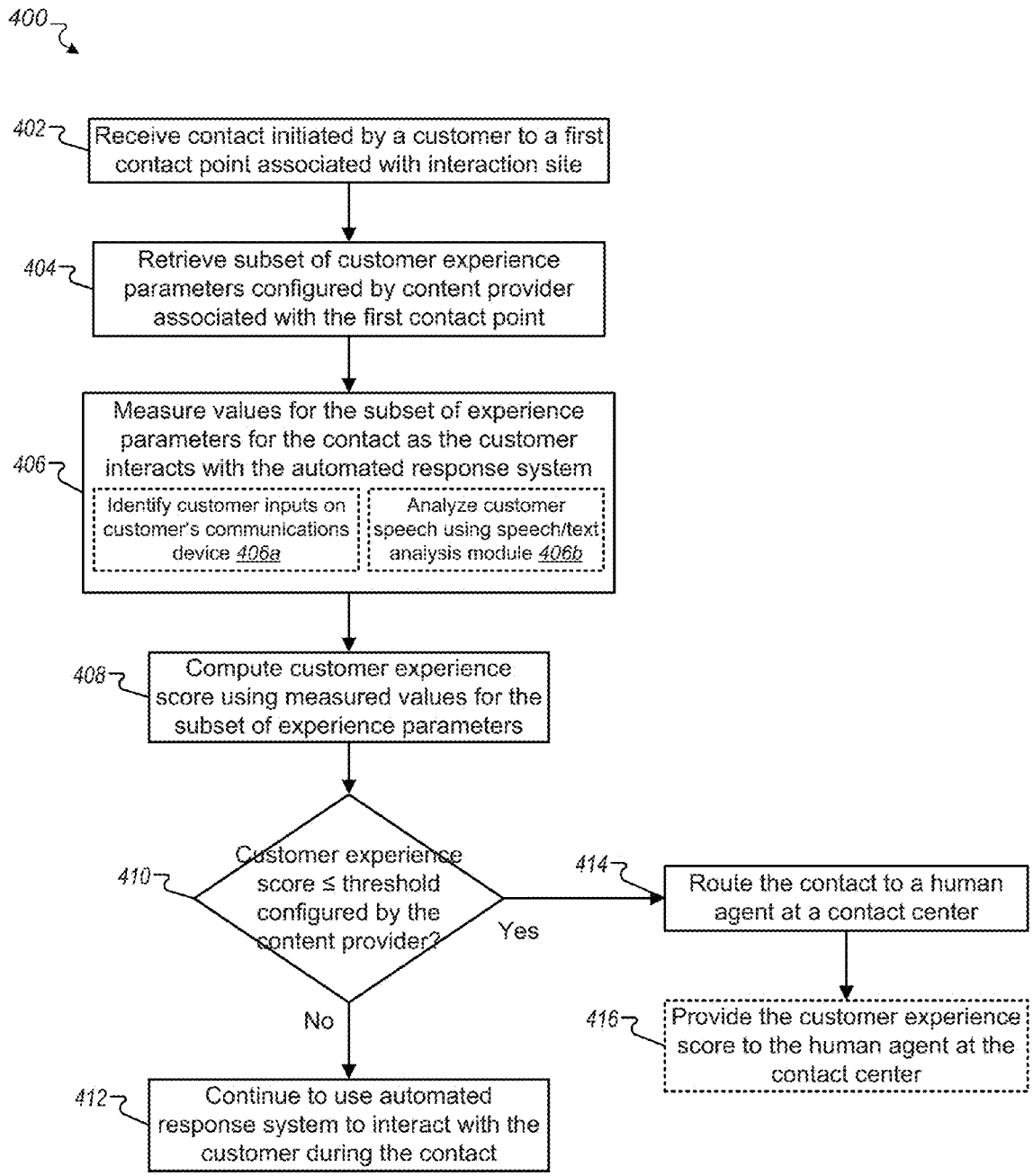
FIG. 4 is a flow chart illustrating an example of a process implemented by a communications system for routing a customer's communications based on the customer's satisfaction level.

FIG. 4 is a flow chart illustrating an example of a process 400 implemented by a communications system for routing a customer communications based on the customer's satisfaction level. The process 400 may be used for routing customer communications corresponding to an interaction site designed using the GUI 200 and hosted by the contact handling platform 130. For example, the process 400 may be used for routing customer communications made by subscribers of the "Exemplary Cellular" cellular service provider who call the company's "Customer Support" site. Accordingly, the following section describes the process 400 as being performed by components of the system 100. However, the process 400 may be performed by other systems or system configurations.

In some implementations, the process 400 is implemented by the contact handling platform 130 and more specifically, by the components of the contact handling platform working in conjunction with one another, such as the ARS 132, the STAM 134, the ARM 136 and the data store 138. These modules use the one or more processors included in the contact handling platform to execute the instructions configured by a content provider that are stored in the data store (e.g. the instructions 139), thereby hosting the interaction site associated with the content provider, and processing customer communications to the interaction site, as described by the process 400. In some implementations, the contact handling platform may simultaneously host multiple interaction sites that are associated with the same content provider, or different content providers.

At 402, the contact handling platform receives a contact initiated by a customer to a first contact point associated with the interaction site. For example, a cellular customer for "Exemplary Cellular" company may call a customer service telephonic number (e.g., "1-800-123-4567") that is associated with the cellular company's "Customer Support" interaction site. The call is received at the contact handling platform 130. Initially, the call is answered by the ARS 132, which determines that the call is intended for the "Customer Support" interaction site based on identifying the telephonic number being called. Since the communications mode used is telephonic, the ARS 132 also may determine that the customer's communications device (e.g., 110) is voice-enabled.

At 404, the subset of customer experience parameters configured by content provider associated with the first contact point are retrieved. For example, the cellular service provider may have configured the parameters 208 while designing the "Customer Support" site. The parameters 208 may be a subset of the parameters that are available in the system, e.g., provided by the contact handling platform 130. The cellular service provider also may have generated some topics including keywords or phrases, or both, using the settings interface 210. The contact handling platform 130 retrieves them from the data store 138 and processes them while handling customer communications for the "Customer Support" interaction site.

Values for the subset of experience parameters for the contact are measured at 406 as the customer interacts with the automated response system. For example, the contact handling platform 130 may track how the cellular subscriber interacts with the ARS 132 when the ARS answers the call.

As part of measuring the experience parameters, the system may identify the customer's inputs on the customer's communications device at 406a. For example, the ARS 132 may track the cellular subscriber's inputs, such as button presses on the subscriber's communications device 110. In this manner, the ARS 132 may determine some of the parameters specified by the cellular service provider, such as whether the subscriber is making any VUI errors, whether the subscriber is not completing tasks, what is the "zero out" time, if any, among others.

In parallel, at 406b the system may analyze the customer's speech using the speech/text analysis module. For example, the STAM 134 listens continuously in the background to determine whether the subscriber speaks while interacting with the ARS 132. If speech is detected, the STAM 134 analyzes the spoken words to look for matches to topics that are configured by the cellular service provider, e.g., phrases that indicate that the subscriber is dissatisfied, such as "I want to cancel my service plan" or "Your service is terrible."

At 408, the customer experience score is computed using measured values for the subset of experience parameters. For example, detecting the phrase "I want to cancel my service plan" as spoken by the subscriber during the interaction, the STAM 134 may pass this information to the ARM 136. At the same time, the ARS 132 may detect that the subscriber did not complete three tasks and made four VUI errors, and these data are also forwarded to the ARM 136. Then the ARM 136 computes the subscriber's customer experience score by subtracting, from the default customer experience score, the weights of the detected parameters as specified by the cellular service provider using the settings interface 206. Therefore, the customer experience score may be computed to be 100%– 10% (5%×2 for the four VUI errors)—30% (10%×3 for the three tasks not completed)—5% (for the one phrase recognized in the subscriber's speech), which equals 55%.

In some implementations, the customer experience score is computed only when the interaction flow reaches a "Check for Customer Experience Score" page 230. However, in other implementations, the customer experience score is computed periodically (e.g., once every 30 seconds) or continuously throughout the whole interaction flow (i.e., the whole interaction site) or throughout a pre-designated portion of the interaction flow (i.e., a pre-determined set of linked interaction pages or a predetermined set of tasks).

In implementations where the customer experience score is computed periodically or continuously, the content provider may configure the frequency at which the computations are performed, e.g., using an interaction site-level setting similar to the Customer Experience settings shown by the settings interface 206. The content provider may access this setting to provide the instructions information 232 on page 230 that identify the appropriate threshold to be used and that identify the page titled "Route to Agent Page" that will be selected if the score falls below the threshold. The customer also may specify the frequency of calculating the score (e.g., that the score should be calculated in intervals of every 30 seconds or that the score should be continuously calculated). In some implementations, the customer also may specify the set of pages or tasks in the interaction flow (e.g., pages 1000 through 4000) during which the continuous or periodic computation of the customer experience score should occur.

In some implementations, the customer may specify different thresholds and/or "Route to Agent" pages for different groupings of linked pages or for different tasks. Notably, no such pages or tasks would have to be specified if the content provider or platform provider configures the experience score calculations to be instead continuously or periodically executed throughout any interaction with the interaction site, irrespective of where that interaction is in the interaction flow, and, moreover, configures the calculations to always route dissatisfied customers using the same "Route to Agent" page.

At 410, it is decided whether the customer experience score is less than or equal to the threshold configured by the content provider. For example, the ARM 136 compares the subscriber's customer experience score to the threshold 232a configured by the cellular service provider using the interaction page 230.

If the customer experience score is not less than or equal to the threshold configured by the content provider, then at 412 the system continues to use the automated response system to interact with the customer during the contact. For example, if the customer experience score computed by the ARM 136 is greater than the threshold 232a value, then the ARM 136 determines that the ARS 132 may continue to handle the call and accordingly the interaction with the customer proceeds using the ARS 132.

On the other hand, if the customer experience score is less than or equal to the threshold configured by the content provider, then at 414 the system routes the contact to a human agent at a contact center. To illustrate, continuing with the above example, the ARM 136 determines that the computed customer experience score 55% is less than the threshold 232a value 60% configured by the cellular service provider. Consequently, the ARM 136 routes the subscriber's communications session to an agent at a contact center that handles customer communications for the "Customer Support" interaction site. For example, the agents in contact center 140 may be employed by the Exemplary Cellular to handle the company's customer contacts. Therefore, the ARM 136 may connect the subscriber's call session to first agent available among the agents 140_1, 140_2, or 140_N.

Optionally, in some implementations, the customer experience score is provided to the human agent at the contact center, at 416. For example, the ARM 136 routes the subscriber's call to the agent 140_2 in the contact center 140. The ARM 136 sends a call request to the agent 140_2, which shows up on the GUI 300 displayed to the agent 140_2 (e.g., in the fields 302a and 302b). When the agent answers the call request and the subscriber is connected to the agent, the ARM 136 "whispers," i.e., silently displays, the subscriber's customer experience score to the agent, e.g., using the field 306d in the GUI 300. In addition, the ARM 136 may provide an indication of the subscriber's emotional state, e.g., using the field 306f, as described previously.

In some implementations, the process 400 may be used as the default routing strategy for connecting customer communications to human agents. As described, the process 400 may connect a subscriber's customer communications to the first agent available to take the call or may connect a subscriber's customer communications to an available agent using, as the default routing strategy, any of the multiple different routing strategies mentioned previously, including routing to the most idle agent, routing to the least utilized agent, and routing using a round robin algorithm. The process 400 does not attempt to find the most suitable agent for handling the subscriber's session. However, in some implementations, a routing strategy may match customer communications to agents most suitable for handling the communications.

Figure 5:
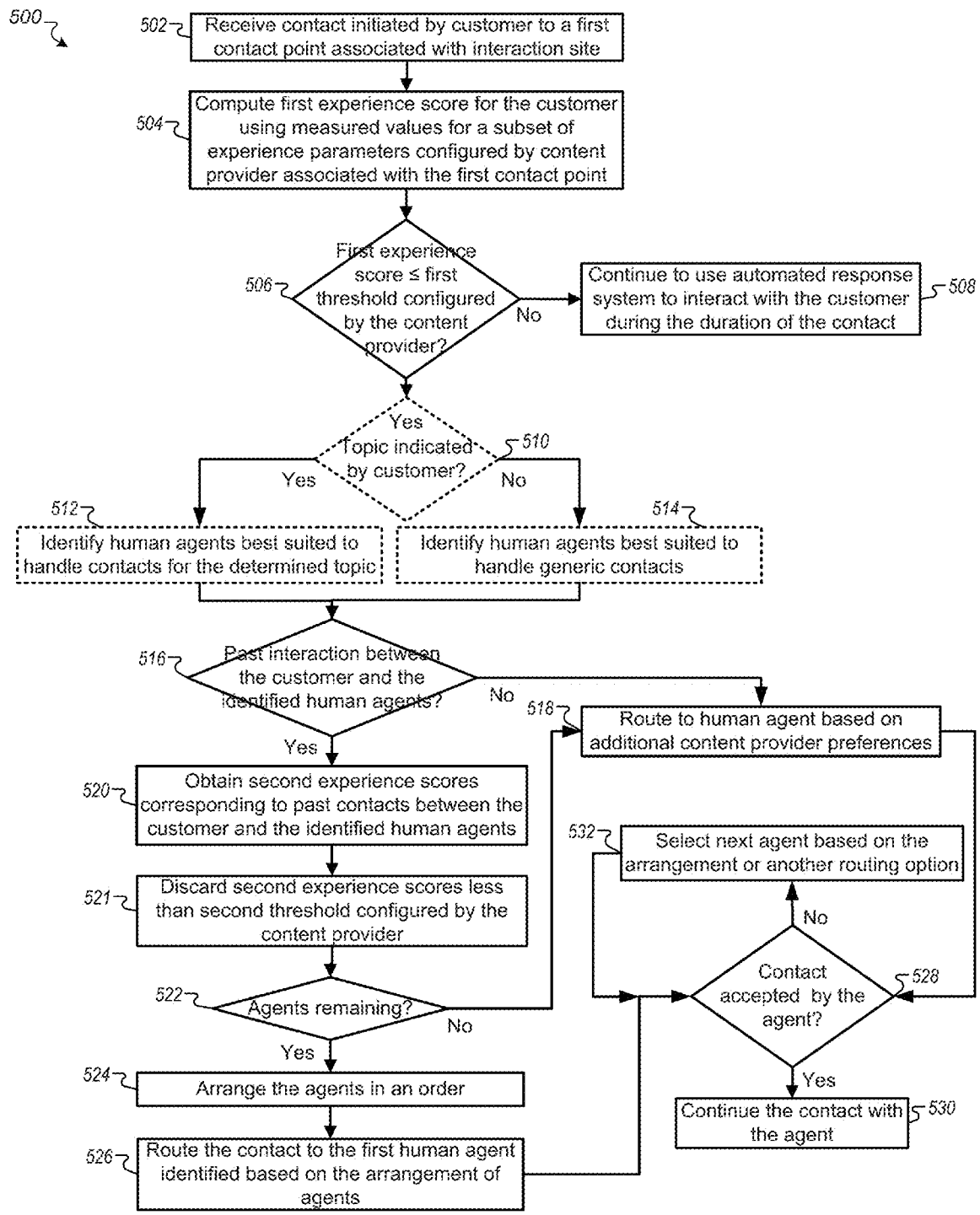
FIG. 5 is a flow chart illustrating an example of a process implemented by a communications system for matching a customer's communications to a human agent who is most suitable for handling the customer's communications.

FIG. 5 is a flow chart illustrating an example of a process 500 implemented by a communications system for matching a customer to a human agent who is most suitable for handling the customer's communications. The process 500 may be used for routing customer communications corresponding to an interaction site designed using the GUI 200 and hosted by the contact handling platform 130. For example, the process 500 may be used for routing customer communications made by subscribers of the "Exemplary Cellular" cellular service provider who call the company's "Customer Support" site. Accordingly, the following section describes the process 500 as being performed by components of the system 100. However, the process 500 may be performed by other systems or system configurations.

In some implementations, the process 500 is implemented by the contact handling platform 130 and more specifically, by the components of the contact handling platform working in conjunction with one another, such as the ARS 132, the STAM 134, the ARM 136 and the data store 138. These modules use the one or more processors included in the contact handling platform to execute the instructions configured by a content provider that are stored in the data store (e.g. the instructions 139), thereby hosting the interaction site associated with the content provider, and processing customer communications to the interaction site, as described by the process 500. In some implementations, the contact handling platform may simultaneously host multiple interaction sites that are associated with the same content provider, or different content providers.

At 502, the contact handling platform receives a contact initiated by a customer to a first contact point associated with the interaction site. For example, a cellular customer for "Exemplary Cellular" company may call a customer service telephone number (e.g., "1-800-123-4567") that is associated with the cellular company's "Customer Support" interaction site. The call is received at the contact handling platform 130. Initially, the call is answered by the ARS 132, which determines that the call is intended for the "Customer Support" interaction site based on identifying the telephonic number being called. Since the communications mode used is telephonic, the ARS 132 also may determine that the customer's communications device (e.g., 110) is voice-enabled.

At 504, the first experience score for the customer is computed using measured values for a subset of experience parameters configured by a content provider associated with the first contact point. In some implementations, the first experience score for the customer is the customer experience score that is based on the customer's interaction with the ARS 132. For example, the contact handling platform 130 (in particular, the ARM 136) may compute the subscriber's first experience score as described by the process 400 at 404, 406 and 408.

At 506, a determination is made whether the first experience score is less than or equal to a first threshold configured by the content provider. For example, the ARM 136 may compare the subscriber's first experience score to the threshold 232a configured by the cellular service provider using the interaction page 230.

If the first experience score is not less than or equal to the threshold configured by the content provider, then at 508 the system continues to use the automated response system to interact with the customer during the contact. For example, if the customer experience score computed by the ARM 136 is greater than the threshold 232a value, then the ARM 136 determines that the ARS 132 may continue to handle the call and accordingly the interaction with the customer proceeds using the ARS 132.

On the other hand, if the customer experience score is less than or equal to the threshold configured by the content provider, then, in some implementations, at 510 the contact handling platform checks whether a topic has been indicated by the customer. For example, the STAM 136 listens continuously for words spoken by the subscriber as he or she interacts with the ARS 132. If customer speech is detected, the STAM checks whether the subscriber utters one or more words that match topic keywords configured by the cellular service provider using the settings interface 210. For example, the STAM 134 checks whether the subscriber says "I need technical support," which is matched by the STAM 134 to the sub-topic "Technical Support" 222b under topic "Escalation" 222a; or whether the subscriber says "Your service is terrible," which is matched by the STAM 134 to the "Dissatisfaction" topic 222a.

In some implementations, if it is determined that a topic has been indicated by the customer, then at 512 the contact handling platform identifies human agents who are best suited to handle contacts for the determined topic. For example, the STAM 134 may recognize that the subscriber said "I want to upgrade my plan," which is determined by the STAM as matching the sub-topic "Sales" 222b. This information is passed to the ARM 136, which examines the list of agents 244 specified by the cellular service provider using the page 204. The ARM 136 determines that agents "Jane Smith" and "Daisy Gasby" have skills that match the determined topic, i.e., sales, and therefore identifies these two agents as best suited to handle contacts for the topic "Sales." Additionally or alternatively, the topic may be determined from the user interaction with the ARS 132 during which the user made selections in response to prompts that identified the topic of interest to the user (e.g., the user selected the button "2" on his or her telephone to indicate a desire for technical support in response to the prompt "If you wish to talk to our sales department, please press 1. If you need technical support, please press 2.")

On the other hand, if it is determined that a topic has not been indicated by the customer, then, in some implementations, at 514 the contact handling platform identifies human agents who are best suited to handle generic contacts. For example, the STAM 134 may determine that the subscriber did not speak anything meaningful while interacting with the ARS 132, or the STAM may not match the subscriber speech to any configured topic 222a or 222b. This information is passed to the ARM 136, which examines the list of agents 244 and determines that agent "Naya Roych" is best suited to handle the generic contact associated with the subscriber. In some implementations, the ARM 136 may determine that all agents in the list 244 are suited to handle generic contacts, since such contacts do not need that the agents have any specific skills.

At 516, the system checks whether there has been past interaction between the customer and the identified human agents. For example, the cellular service provider may have configured instructions 258 on page 240 to enable historical match. Accordingly, the ARM 136 may retrieve, from the data store 138, past interaction data that are associated with the calling subscriber, who is identified by the contact handling platform from its records using the subscriber's calling number. Upon retrieving the past interaction data, the ARM 136 checks whether the data includes information on customer communications that had been handled by any of the human agents identified at 512 or 514.

If past interaction between the customer and the identified human agents is not found, then at 518 the customer communications is routed to a human agent based on additional content provider preferences. For example, the ARM 136 may determine that there is no data on past interactions between the calling subscriber and the identified agents. In such an event, in some implementations the ARM 136 may route the call to one of the identified agents using the default strategy, as described previously by the process 400 at 414 and 416. In some other implementations, the cellular service provider may have enabled skills-based routing by configuring the instructions 254 on page 240. In such cases, the ARM 136 may select the most suitable agent from the identified agents based on the option specified by the cellular service provider using the instructions 256, in a manner as described previously with respect to the page 240.

After selecting the agent, the ARM 136 sends a connection request to the agent to connect the subscriber call at issue with the agent. At 528, the ARM checks whether the contact has been accepted by the agent, as described in greater detail below.

On the other hand, if past interaction between the customer and the identified human agents is found, then at 520 the ARM 136 obtains second experience scores corresponding to past contacts between the customer and the identified human agents. These second experience scores are the second customer experience scores that are computed based on interactions between the customer and the human agents, as described previously. For example, the ARM 136 obtains second customer experience scores that were computed for the calling subscriber during his or her past interactions with the "Customer Support" interaction site, based on the analysis of the subscriber's inputs by the STAM 134.

At 521, second experience scores that are less than the a second threshold configured by the content provider are discarded. For example, in some implementations, the cellular service provider may enable advance options for the historical match by configuring the instructions 260 and 262 using the "Advanced Options" tab 242b on interaction page 230. In such implementations, the ARM 136 may compare the second customer experience scores to the threshold 260a, and remove the identified agents corresponding to whom the subscriber's second customer experience scores based on past interactions are less than the threshold 260a.

In such implementations, the content provider may configure the first threshold 232a and the second threshold 260 such that the ARM 136 discards agents corresponding to whom the subscriber's second customer experience scores are less than the first experience score computed for the present call. This may be achieved by setting the threshold 260a higher than the threshold 232a, such that the agents who are remaining after performing the comparison using the threshold 260a corresponding to second experience scores that are higher than the subscriber's current first experience score that is compared to the threshold 232a. In such implementations, the first and second experience scores may be normalized to a common unit, such as a common spectrum of satisfaction that can range, for example, from 0% indicating that the customer is extremely dissatisfied, to 100% indicating that the customer is extremely satisfied, with 50% indicating that the customer is mildly satisfied.

In some implementations that use a common satisfaction spectrum to express the first experience scores and the second experience scores, which reflect the customer's satisfaction when interacting with the ASR and in conversing with an agent respectively, the content provider and/or the platform provider may select to have the pre-determined threshold 260a to be the same as the first experience score that resulted in the customer communications being routed to an agent. For example, if the first customer experience score for the customer communications is computed to be 57%, which is less than the threshold 60% set in 232a and therefore the customer communications is routed to agents, the threshold 260a may be configured such that it is dynamically set to 57%. Accordingly, the ARM 136 will discard agents corresponding to whom the customer's second customer experience scores for past interactions were less than 57%.

The above filtering may be performed because the system has reached this particular point in the interaction flow only because the value of the subscriber's first customer experience score indicates that the subscriber is dissatisfied with the current interaction. Second customer experience scores that are even less than the first customer experience score, which is already considered to be unsatisfactory for the subscriber, indicates that the subscriber did not have a positive experience in the agent interactions associated with these low second customer experience scores. Therefore, it is likely that the subscriber's satisfaction level will not improve by routing the subscriber's call to one of these agents; rather, the subscriber may have a more negative experience.

At 522, the system checks whether there are agents remaining. For example, in some cases no agent will remain in consideration for routing of the subscriber's call after the ARM 136 removes the identified agents corresponding to whom the subscriber's second customer experience scores are either less than the first customer experience score, or less than the threshold 260a.

If it is determined that no agents are remaining, then the execution of the interaction flow moves to 518 and the customer communications is routed to a human agent based on additional content provider preferences. On the other hand, if it is determined that there are agents are remaining for consideration, then the system, i.e., the ARM 136 selects, from the remaining agents, an agent who is most suitable for handling the current customer communications. In some implementations, this is performed based on one of the agent select options specified by the content provider using the instructions 256 on page 240. At 524, the ARM 136 arranges the agents in an order. For example, the cellular service provider may have selected the "Most Idle Agent" option in 256. Accordingly, the ARM 136 arranges the remaining agents, i.e., the agents corresponding to whom the subscriber's second customer experience scores are either (a) above the subscriber's first customer experience score for this call, or (b) above the threshold 260a configured by the cellular service provider, or both, in an order starting with the agent who has been idle for the longest time period and ending with the agent who has been idle the shortest time.

At 526, the ARM 136 routes the contact to the first human agent identified based on the arrangement of agents. For example, the ARM 136 selects the first agent from the arrangement of agents described above as the agent who has been most idle i.e., who has not handled communications from subscribers of the cellular service provider for the longest period of time among all the remaining agents. Then the ARM 136 sends a call request to the agent for connecting the subscriber call at issue to the agent. For example, the ARM rings the agent's telephone number, or sends a graphical indication to the agent's GUI 300, or both.

At 528, the ARM 136 checks whether the contact has been accepted by the agent. For example, the ARM waits for 3 rings on the agent's telephone, based on the instructions 250 configured by the cellular service provider.

If the contact is accepted by the agent, then at 530 the contact is continued with the agent. For example, if the agent answers the connection request within 3 attempts, then the ARM 136 determines that the agent has accepted the connection request. In some implementations, the ARM 136 sends details on the call and the subscriber to the agent, which are shown to the agent using one or more of the panels 304a, 304b and 304c. The subscriber's call to the "Customer Support" interaction site then proceeds with the subscriber interacting with a human agent.

On the other hand, if the contact is not accepted by the agent, then at 532 the ARM 136 selects the next agent based on the arrangement or another routing option. For example, if the selected agent does not answer the connection request within 3 attempts, then the ARM 136 determines that the agent is unavailable, e.g., the agent is busy interacting with another customer or the agent is away. In such cases, the ARM 136 selects the second most idle agent from the arrangement of agents ordered based on the "Most Idle Agent" option, and sends a connection request to the newly-selected agent. If this agent also does not accept the contact, then the ARM selects the next agent from the arrangement, and so on, till there are no agents remaining.

If there are no agents remaining who meet the criteria of 520-526, then the ARM 136 selects another routing option. For example, the ARM 136 may connect the subscriber to the assigned agent's voicemail, based on the instructions 246. Alternatively, if the cellular service provider has configured advanced options for the historical match, then the ARM 136 may explore other route options specified in page 8000, based on the instructions 262.

Figure 6:
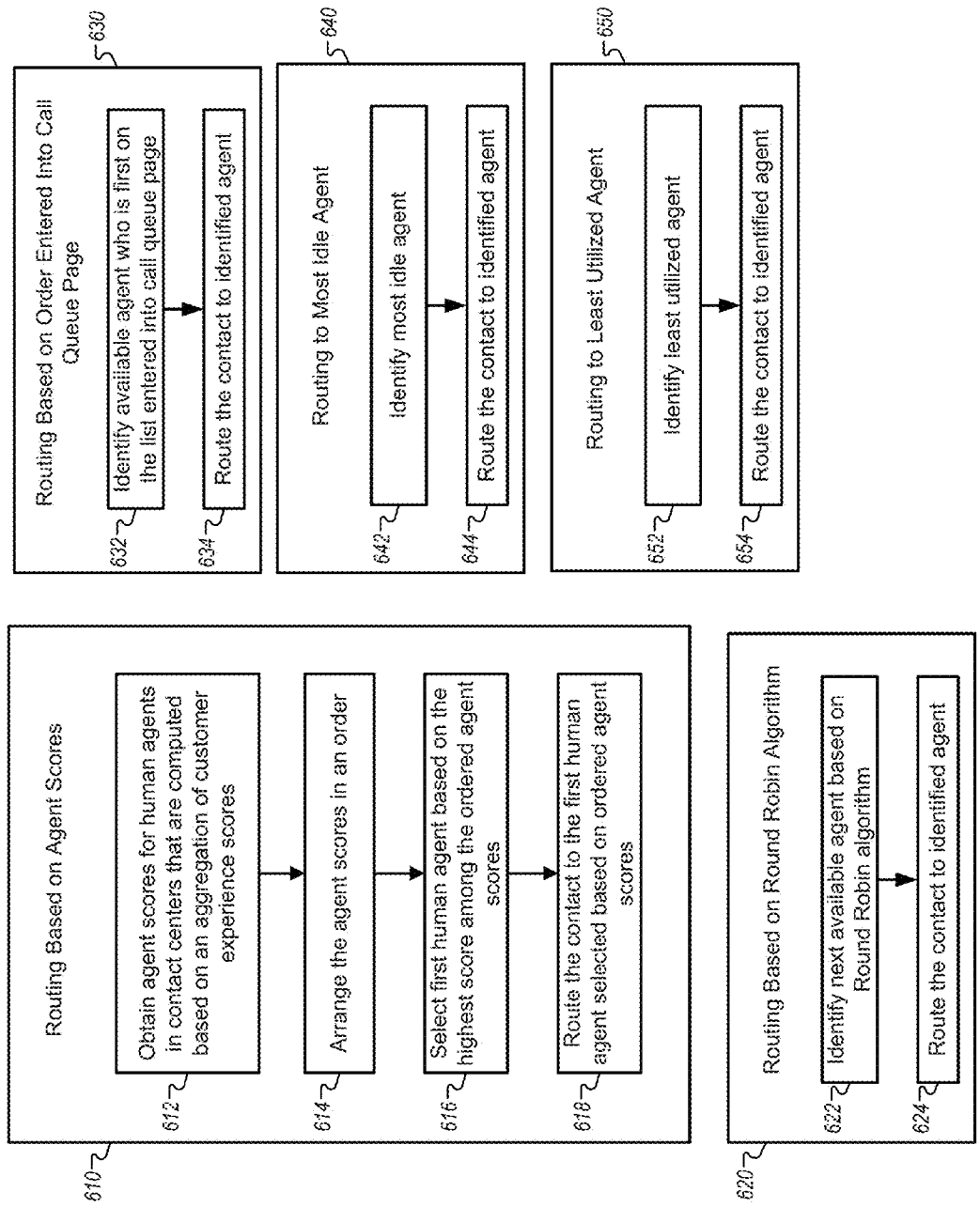
FIG. 6 illustrate flow charts showing examples of processes implemented by a communications system for selecting a human agent for routing user communications based on different agent selection options.

FIG. 6 illustrate flow charts showing examples of processes 610, 620, 630, 640 and 650 implemented by a communications system for selecting a human agent for routing user communications based on different agent selection options. The processes 610, 620, 630, 640 and 650 may be used for agent selection during routing customer communications corresponding to an interaction site designed using the GUI 200 and hosted by the contact handling platform 130. For example, the processes 610, 620, 630, 640 and 650 may be used for agent selection by the contact handling platform while implementing the process 500. When routing a new customer communications using the process 500, the ARM 136 identifies agents who are suitable for handling the customer communications as described at 512, 514, 516, 520, 521 and 522. The contact handling platform arranges the agents in an order at 524, at which point the process selected from 610, 620, 630, 640 and 650 may be used. Accordingly, the following section describes the processes 610, 620, 630, 640 and 650 as being performed by components of the system 100. However, the processes 610, 620, 630, 640 and 650 may be performed by other systems or system configurations.

The contact handling platform 130 uses the process 610 when the content provider has selected the option "Agent Scores" using instructions 256 on page 240. At 612, the contact handling platform obtains agent scores for human agents in contact centers that are computed based on an aggregation of customer experience scores. As described previously, in some implementations, an agent score for an agent is a sum of the second customer experience scores for all the customer communications handled by the agent. The ARM 136 updates the agent score for the agent after every customer communications for which the second customer experience score is computed. Subsequently, when arranging the identified agents based on their agent scores, the ARM 136 retrieves the corresponding agent scores, e.g., from the data store 138.

At 614, the agent scores are arranged in an order. For example, the ARM 136 may arrange the agent scores in an order of decreasing scores, starting with the agent whose score is the highest and ending with the agent whose score is the lowest.

At 616, the first human agent is identified based on the highest score among the ordered agent scores. For example, the ARM 136 selects the first agent who is at the top of the arrangement, i.e., the agent with the highest agent score.

At 618, the contact is routed to the first human agent selected based on ordered agent scores. For example, the ARM 136 sends a connection request to the selected agent for connecting the customer communications at issue to the agent. The ARM also may send a graphical indication to the agent's GUI 300.

The contact handling platform 130 uses the process 620 when the content provider has selected the option "Hunt/Round Robin" using instructions 256 on page 240. At 622, the contact handling platform identifies the next available agent based on a Round Robin algorithm. For example, the ARM 136 schedules the agents as they become available (e.g., in a queue), and selects first available agent from the schedule. If the first agent in the list is not available (e.g., the agent is presently handling a customer communications or is away), then the ARM 136 checks whether the next scheduled agent is available, and then the next, and so on.

At 624, the contact is routed to the identified agent. For example, upon identifying the next available agent based on the order the agents are specified by the list 244, the ARM 136 sends a connection request to the agent for connecting the customer communications at issue to the agent. The ARM also may send a graphical indication to the agent's GUI 300.

The contact handling platform 130 uses the process 630 when the content provider has selected the option "Order Entered" using instructions 256 on page 240. At 632, the contact handling platform identifies the available agent who is first on the list 244 entered in the call queue page 240. For example, the ARM selects an agent based on the order the agents are specified by the list 244. The ARM 136 identifies the first agent in the list 244, e.g., "Jane Smith" and selects this agent for routing the customer communications.

At 634, the contact is routed to the identified agent. For example, the ARM 136 sends a connection request to agent "Jane Smith" for connecting the customer communications at issue to the agent. The ARM also may send a graphical indication to the agent's GUI 300. If agent "Jane Smith" is not available (e.g., the agent is presently handling a customer communications or is away), then the ARM 136 checks whether the next agent specified in the list (e.g., "John Doe") is available, and then the next, and so on.

The contact handling platform 130 uses the process 640 when the content provider has selected the option "Most Idle Agent" using instructions 256 on page 240. At 642, the contact handling platform identifies the most idle agent. In some implementations, the contact handling platform may log the times when agents interact with customers. In this manner, the ARM 136 may have knowledge of the when was the last time an agent was engaged in a customer communications and accordingly compute the idle times for the agents. The ARM 136 arranges the available agents in an order of decreasing idle times, such that the first agent in the arrangement is identified as the most idle agent, i.e., the agent who has been idle for the longest period among the available agents.

At 644, the contact is routed to the identified agent. For example, upon identifying the most idle agent, the ARM 136 sends a connection request to the identified agent for connecting the customer communications at issue to the agent. The ARM also may send a graphical indication to the agent's GUI 300.

The contact handling platform 130 uses the process 650 when the content provider has selected the option "Least Utilized Agent" using instructions 256 on page 240. At 652, the contact handling platform identifies the least utilized agent. For example, the contact handling platform may track how many customer interactions have been handled by each agent. Using this knowledge, the ARM 136 may arrange the available agents in an order of increasing number of customer interactions handled, such that the first agent in the arrangement is identified as the least utilized agent, i.e., the agent who has handled the least number of customer sessions, among all the available agents.

At 654, the contact is routed to the identified agent. For example, upon identifying the least utilized agent, the ARM 136 sends a connection request to the identified agent for connecting the customer communications at issue to the agent. The ARM also may send a graphical indication to the agent's GUI 300.

In some cases, web marketing technologies track client web activity, such as web pages that were visited, links that were clicked, documents that were downloaded, forms that were filled, and the like. Not included are non-web activities, such as phone numbers that were dialed by the client or prospect, types of conversations that they had, and the like. Such information is sometimes sporadically captured, often independent of the web activity. The tracked results may not completely capture views of visitor activities, and may lack information pertaining to the types of activities (for example, making phone calls) that are associated, for example, with moments when a user's interest in the service or product is high.

In some implementations, the method described above can be implemented as a computer software program executable by data processing apparatus to perform operations that may be embedded into web interfaces (including chat windows) and that include "click-to-call" functionalities that can initiate phone calls with the visitor while at the same time storing the context of the phone initiation. The context of the phone initiation can include, for example, the identity of the visitor, as it is defined in the context of web tracking, the time of the call, and the exact web page within which the call was made. In addition to the context, information such as information about the call itself (for example, length of the call, the agent who fielded the call, the IVR selections, etc.) can be stored. In some implementations, the context and the information described above can be stored in a back-end data destination (e.g., a CRM software system) for later analysis.

The techniques described above may offer various benefits. For example, by capturing all activities from a user (for example, a prospect or a client), a more complete narrative of prospect activities across both channels (i.e., the web channel and the phone channel) can be constructed. This will enable tools such as Drip Marketing software to assess more accurately a given prospect's level of interest by tracking the user's cross-channel activities. For example, a prospect who has been visiting web pages and downloading documents, and who then calls a phone number, should be scored as a warm lead. A warm lead is a prospect whose interest in the product or the service is relatively more significant than another prospect who, for example, started a quick chat session and then left. A warm lead is also relatively more significant compared to a prospect who, for example, is only just browsing. More meaningful yet would be a prospect who, for example, has been browsing, has engaged in a chat session, and has now called into the sales line with an inquiry. Such a call can then be marked, in real time, as a warm lead, and handled accordingly.

Additionally, by capturing the web context of the phone call initiation action, web site designers can gain meaningful insight into which pages among the several pages that they have deployed, are converting visitors into callers. This may enable them to focus on replicating those strategies that have effectively resulted in such conversions.

In some cases, medical samples may be securely ordered using mobile devices. Medical professionals, such as doctors, frequently conduct transactions with sources that provide medications, for example, pharmaceutical companies, to procure medical samples. For certain medications, the identities of doctors are authenticated prior to processing and/or completing a transaction, particularly, when the medications are regulated substances. The authentication process ensures that a person who places an order to procure a particular medical sample is authorized to do so. For example, to place an order for a medical sample, a doctor can place a telephone call to a source that provides the medication. To authenticate the doctor's identity, the doctor can be asked a series of questions. The doctor's identity can be authenticated based on the answers to the questions.

Advancements in technology have enabled users to conduct transactions using systems and devices other than telephones. For example, a user and a source of products each can have respective computers that are connected to each other through a network such as the Internet. Using the computer, the user can transmit an order to the source. The source's computer can receive and process the user's order. More recently, mobile devices enable users to communicate with computers over networks such as a Wi-Fi network, 3G or 4G telephonic networks, and the like. To employ computers and mobile devices to procure medical samples through the networks, the systems and devices need to be equipped with authentication capabilities to ensure the security of the transactions.

The systems and methods for secure ordering of medical samples using mobile devices can be implemented, for example, as a computer software application executing on a mobile device. The application, when executed by the mobile device, can be configured to enable a user, for example, a doctor or authorized medical staff, to conduct a transaction with a source that provides medications to procure certain medications, for example, medical samples. In some implementations, the application can connect the user of the mobile device and the source that provides the medications through one or more networks, for example, a Wi-Fi network, a 3G or 4G telephonic network, and the like.

When executed by the mobile device, the application can enable the user to select types and quantities of medications. The application can authenticate the user, i.e., verify that the user is authorized to place orders for the selected medications, through the use of multiple security layers. As described in more detail below, the disclosed techniques for ordering medical samples provide enhanced security by requiring that a person attempting to order the medical samples satisfy one or more of the following exemplary constraints before the order is approved: (1) be in physical possession of the mobile device through which the order will be submitted; (2) provide a password or other authentication credentials to unlock the mobile device for use by the user (i.e., a communication device level unlock); (3) provide a password or other authentication credentials to unlock an application on the mobile device that is used to place the order (i.e., an application level unlock); (4) be in a physical location that matches one of a set of preauthorized physical locations (for example, be physically within the premises of a previously identified hospital as determined by a Global Positioning System (GPS) within the mobile phone); (5) provide a voice sample (or other biometric authentication data) that is successfully authenticated as corresponding to the voice (or other biological attribute) of a user of the mobile device that is authorized to place the order; and (6) provide confirmation of the order by responding to a communication (for example, an e-mail or a phone call) sent to an identity known to correspond to a user of the mobile device that is authorized to place the order.

More generally, one or more of the security layers can, for example, be based on an identity of the mobile device via which the user is attempting to procure the medical samples, a state of the mobile device, and unique information associated with the user's user account. The layers of security used for a given user or user account can, for example, vary by user and may be set by each user through the configuration/modification of user preferences.

Once a user has satisfied all of the security layers, a transaction to procure identified medical samples can be processed. As stated above, subsequent to processing, a communication (for example, an e-mail or a phone call) can be transmitted to a known identity of the authorized user (for example, an e-mail address or a phone number) indicating that the transaction has been processed. The communication can serve as an additional security layer because the authorized user can disavow the transaction if the authorized user did not conduct or authorize the transaction. In another implementation, a communication can be transmitted to the known identity of the authorized user prior to processing the transaction. The transaction is then only processed if the authorized user responds to the communication by confirming the transaction.

The application enables the secure ordering of medical samples by an authorized doctor or medical staff. By implementing multiple identity verification stages to authenticate the user placing the order, the security of the transaction can be enhanced. The user can easily view a history of all transactions using the mobile device. The application can be executed on any mobile device and can be easy to use without significant training.

Figure 7:
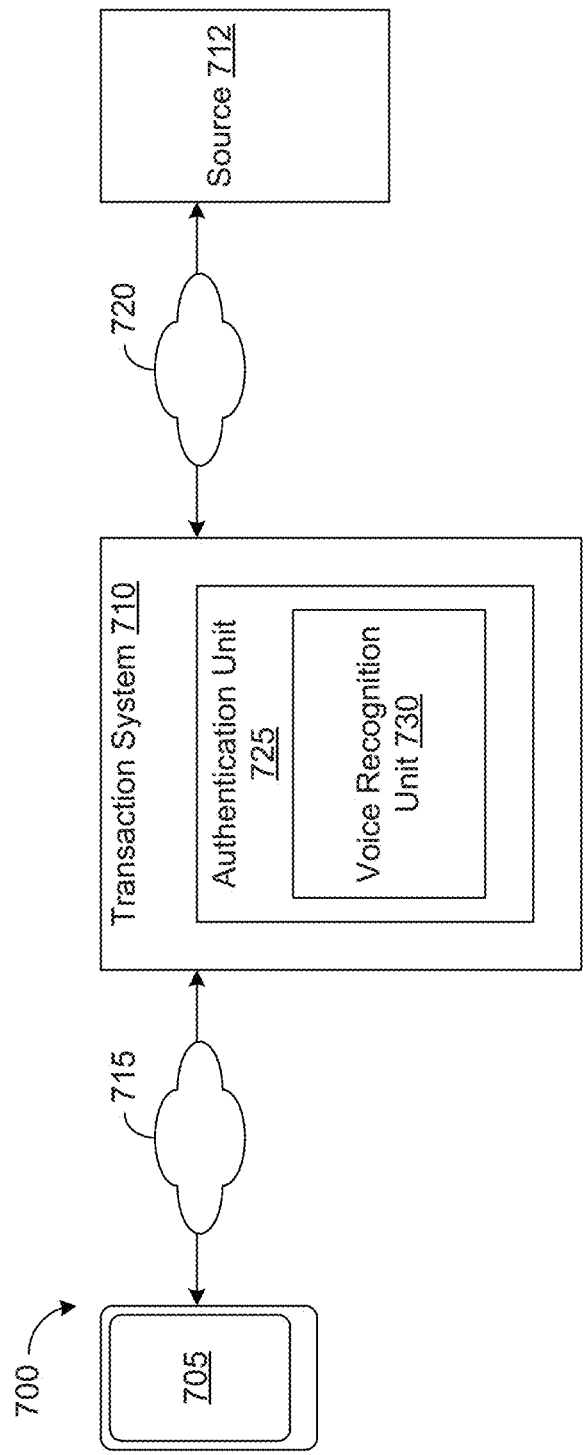
FIG. 7 illustrates an example of an environment for securely ordering medical samples using a mobile device.

FIG. 7 illustrates an example of an environment 700 for securely ordering medical samples using a mobile device 705. A mobile device 705, for example, a smart phone, a personal digital assistant (PDA), and the like, can be operatively coupled to a transaction system 710 through one or more networks 715, for example, a Wi-Fi network, any wireless telephonic network (for example, 3G, 4G), and the like. The mobile device 705 is configured to execute an application that may be employed by a user of the mobile device, for example, a doctor or medical staff, to place an order to procure medical samples. While only the doctor or the medical staff is authorized to procure the medical samples, any user who gains possession of the mobile device 705 can attempt to procure the samples. The application executing on the mobile device, however, is configured to provide several security layers that prevent such unauthorized ordering of medical samples. The application can require that the user clear one or more or all of the security layers to be authenticated as the user who is authorized to procure the medical samples.

The transaction system 710 can be coupled to a source 712 at which the medical samples can be stored. For example, the transaction system 710 can be operatively coupled to a computer server associated with a pharmaceutical company or a distributor of medications. The transaction system 710 can include one or more computer servers that can communicate with one or more servers of the source 712 through networks 720, for example, the Internet. The transaction system 710 can be configured to process the order received from the mobile device 705, as described below, and to communicate a completion of the processing to the source 712. The source 712 can transmit the procured medical samples to the user of the mobile device 705.

The transaction system 710 can include an authentication unit 725 configured to authenticate the user who places an order to procure the medical samples using the mobile device 705. To authenticate a user, the authentication unit 725 can include a voice recognition unit 730 configured to establish an identity of a person based on a voice sample received from the person. The voice recognition unit 730 can be implemented to execute known biometric voice recognition methods.

In some implementations, the transaction system 710 can create user accounts, each associated with a user who is authorized to procure medical samples. To do so, the transaction system 710 can obtain information describing the user (for example, name, address, telephone number, electronic mail address, affiliation to medical institutions, and the like). In addition, the transaction system 710 can obtain a sample of the user's voice based on which the authentication unit 725 can later authenticate the user's identity. In some implementations, the transaction system 710 can receive the voice in the form of an audio file (for example, WAV format, MP3 format, and the like). In alternative implementations, the transaction system 710 can receive the voice in the form of an audio stream. In general, the audio file can be in a format in which the richness of the voice is preserved and data representing the voice is extractable for storage and processing.

The transaction system 710 can associate the received user information and the voice sample to the user's account. In addition, in implementations in which the user conducts the transaction by executing a computer software application on the mobile device 705, the transaction system 710 can also receive an identifier that uniquely identifies the mobile device 705, for example, a Universally Unique Identifier (UUID). In addition, the transaction system 710 can provide the user with an identifier (for example, a login ID) associated with a user-changeable password using which the user can establish a connection between the mobile device 705 and the transaction system 710. During account registration/setup, a user's account may be associated with one or more device identifiers and/or user identifiers.

Having associated the information received from the user with the user's account, the transaction system 705 can employ the received information to authenticate a person who uses the user's account information to procure medical samples during future transactions. Implementations in which the user conducts such transactions using mobile devices are described with reference to the following figures.

In some implementations, the mobile device on which the application is installed includes processors and circuitry to execute the application, and to communicate with the transaction system 710. The mobile device can further include a touch screen through which input can be received and in which output can be displayed. In the touch screen, the mobile device can display visual elements such as images, video, and the like, in a user interface.

Some of the visual elements can be controls through which the application can receive input. For example, the application can display a textbox in the touch screen. Within the textbox, the application can display a name of a medication available for procurement. The textbox is a visual element. The application can enable the user to select the drug by providing input to (for example, touching) the textbox. In such situations, the visual element, i.e., the textbox, is also a control. In addition, the mobile device can include hardware controllers (for example, trackball, track pad, and the like) through which the application can receive input. Other visual elements can represent the output generated by the application in response to the input.

FIGS. 8A-8F illustrate examples of a mobile device executing an application for securely ordering medical samples. When the application is installed on the mobile device, the application can be represented as an icon in the touch screen. To access the icon, the user can first activate the mobile device 705. Mobile devices are typically locked and can be unlocked using a user-created password. Thus, the user can provide an appropriate password to unlock the mobile device 705 to access the icon that represents the application.

If the password is incorrect, then the mobile device 705 remains locked, thereby preventing an unauthorized user of the mobile device 705 from accessing the application. If the password is correct, then the mobile device 705 is unlocked, and the icon representing the application is displayed in the touch screen of the unlocked mobile device 705. Thus, a doctor's input of a password that will unlock the mobile device 705 can be a first security layer that the user of the mobile device 705 needs to clear to conduct a transaction to procure medical samples. Alternatively, the mobile device 705 need not have a password to lock the device. In such situations, the application can be accessed regardless of the user. Additional security layers are described below.

Figure 8A:
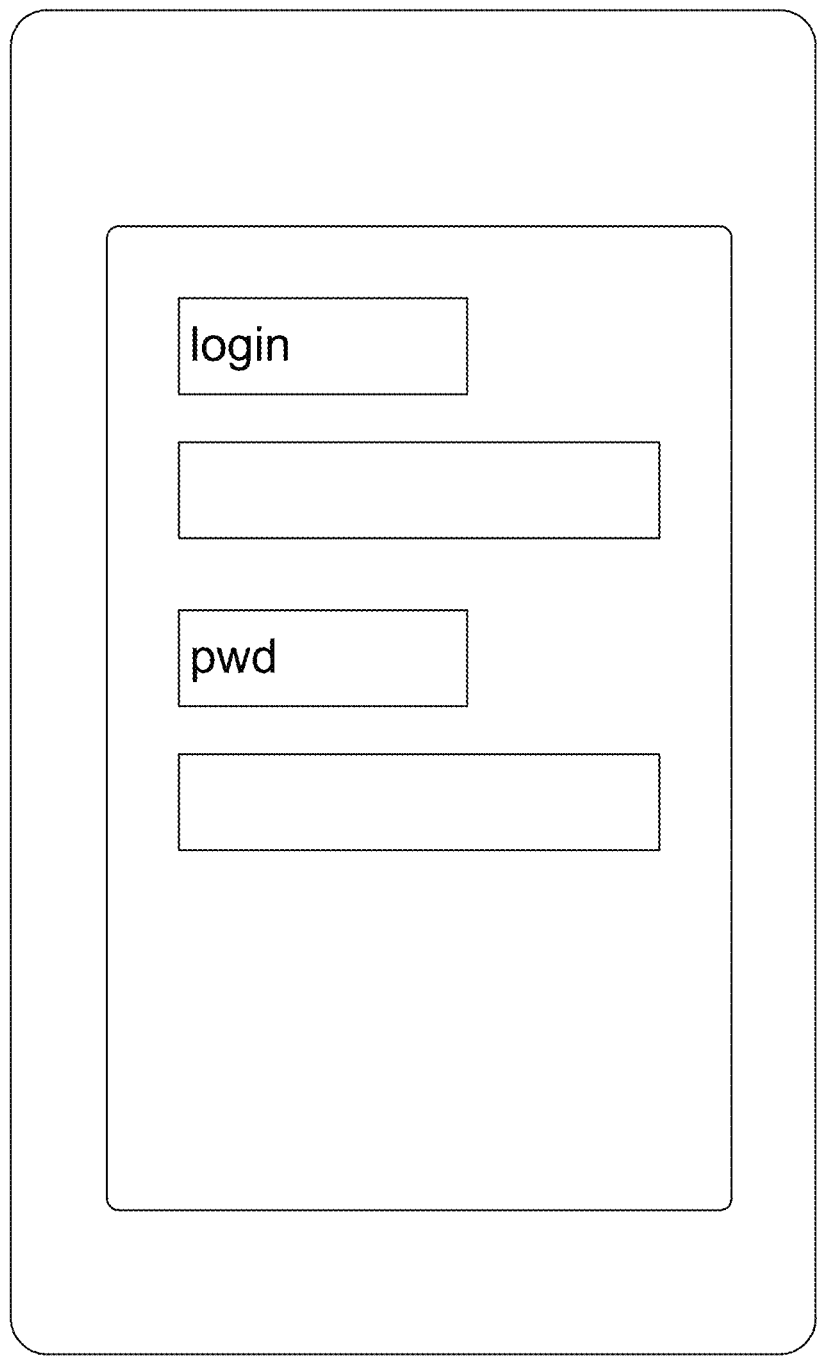
FIGS. 8A-8F illustrate examples of a mobile device executing an application for securely ordering medical samples.

To cause the mobile device to execute the application, the user can select (for example, touch) the icon. In response, the application can display a first user interface in the touch screen, as illustrated in FIG. 8A. In the first user interface, the application can display, two controls, for example, textboxes, within which the user is prompted to enter the login ID and the password that was provided to the user when the user initially created an account with the transaction system 710. If the user provides the correct login identifier and corresponding password, then the application can continue; otherwise, the application can display a message in the first user interface indicating incorrect login information. Subsequently, the application can either allow the user to re-enter the login identifier or terminate.

To enable the user to enter the login identifier and password, the application can provide a keyboard or other suitable input controls. When the user provides the login identifier and the corresponding password, the application can transmit the input to the transaction system 710 (for example, in an encrypted format). If the transaction system 710 determines that the login identifier and the corresponding password match those stored in the system, then the transaction system 710 can transmit an indication of the match to the mobile device 705. In response, the application can allow the user to continue the transaction, for example, by displaying the second user interface shown in FIG. 8B. Alternatively, or in addition, the mobile device 705 itself can store the login identifier and corresponding password, and verify that the user has provided the accurate login identifier and corresponding password to enable the user to proceed with the transaction. Thus, the doctor's input of a login identifier and a corresponding password, that matches the information stored in the transaction system 705, can be a second security layer that the user of the mobile device 705 needs to clear to conduct a transaction to procure medical samples.

Figure 8B:

FIG. 8B illustrates a second user interface in which the application displays a list of available medications. In the second user interface, the application can display the names of medical samples, for example, as multiple visual elements each displaying a medication name. For example, the application can display the visual elements as a list ("DRUG 01," "DRUG 02," "DRUG 03," and so on) that can be scrolled by providing input through either the touch screen or using the hardware controllers or both.

Each of the multiple visual elements can be a control that is selectable. For example, to select a medication name, the user can touch the control that shows the medication name. In response, the application can display a visual element in the second user interface that indicates the selection. For example, the application can display a check symbol adjacent to the selected control. Alternatively, the application can display other types of visual elements, for example, radio buttons. In this manner, the user can select one or more medications from the list displayed in the second user interface.

Figure 8C:
Figure 8D:

In addition to the medication name, the user can additionally select a quantity. For example, after receiving input to select the medication names, the application can display a third user interface that displays multiple controls, each representing a quantity (FIG. 8C). The application can receive a quantity of the medications when the user selects one of the controls displayed in the third user interface.

Having received the medication name and the quantity, the application can display a fourth user interface (FIG. 8D) through which the application can prompt the user to provide vocal input. In the fourth user interface, the application can display a textbox within which the application can display a string of text. For example, the string of text can be a four digit number such as "9542." Further, in the fourth user interface, the application can display a control that the user can select prior to speaking the string of text. For example, the control may be a graphical button having the label "START RECORDING."

After the user selects the control and speaks the string of text, the application can collect the voice sample of the user, information about the medication (medication name and quantity), information about the mobile device, and information about the user. The information about the mobile device can include, for example, the identifier that uniquely identifies the device, location information (such as Global Positioning System coordinates), and the like. The application can transmit the collected information, for example, through Hyper Text Transmission Protocol Secure (HTTPS). Alternatively, or in addition, the application can transmit the collected information as an extensible markup language (XML) post. In some implementations, the application can encrypt the collected information prior to transmitting over the network 715 so that the transmitted information is secure.

The transaction system 710 receives the information transmitted by the application from the mobile device 705. As described previously, when the user created an account with the transaction system 710, the user provided a voice sample that was associated with the user's account. In some implementations, the voice recognition unit 730 is configured to create a data model of the received voice sample and identify characteristics of the voice. When the voice recognition unit 730 receives the voice sample through the fourth user interface during a transaction, the unit 730 can determine that the voice sample received during the transaction and that received when the user's account was created belong to the same person.

The voice recognition unit 730 can provide a signal indicating an outcome of the analysis of the voice sample received during the transaction, to the authentication unit 725. For example, the voice recognition unit 730 can provide a signal indicating that the voice sample received during the transaction and the voice sample received when the user account was created were provided by the same person. Alternatively, the voice recognition unit 730 can provide a signal indicating that the voice samples were from different persons. If the latter, then the transaction system 705 can transmit the indication to the mobile device 705 and, in response, the application can display a message indicating that authentication has failed. Subsequently, the application can display the fourth user interface and enable the user to provide a voice sample again, to repeat the aforementioned process. Alternatively, or after a certain number of attempts, the application can terminate. Thus, a requirement that the user's voice match the voice stored in the transaction system 705 can be a third security layer that the user of the mobile device 705 needs to clear to conduct a transaction to procure medical samples.

As described above, during a transaction, the user provided a voice sample by reading a series of numbers that were displayed in the fourth user interface. The voice recognition unit 730 is configured to select the series of numbers and provide the series to the transaction system 710. The transaction system 710 can transmit the series of numbers to the mobile device 705. The application can display the received series of numbers in the user interface. Each number in the series possesses characteristics based upon which the voice of a user who speaks the number can be analyzed. In some implementations, the voice recognition unit 730 can store multiple series of numbers having certain digits, for example, four digits, three digits, and the like. Alternatively, the voice recognition unit 730 can generate a string of numbers based on predetermined individual numbers.

In alternative implementations, the voice recognition unit 730 can display a string of text in the fourth user interface. Rather than speak a series of numbers, the user can speak the string the text. For example, the string of text can include the medication name. Thus, in such implementations, rather than select the medication using a list, the user can speak the name of the desired medication. This can serve the dual purpose of enabling a user to select a medication name and receiving a voice sample from the user for authentication.

Thus, the authentication unit 725 can authenticate the user who is conducting the transaction when the voice recognition unit 730 transmits a signal to the authentication unit 725 indicating that the voice sample received during the transaction and the voice sample received when the user account was set up are those of the same person. Further, in some implementations, the authentication unit 725 can compare the location information (for example, GPS coordinates) received from the mobile device 705 with location information received from the user when the user account was created. This comparison can serve as an additional security layer that the user of the mobile device 705 needs to clear to conduct a transaction to procure medical samples.

As described above, the application and the transaction system, alone and in combination, subject the user to various security layers. Because the application can be executed using the mobile device 705, the user must possess the mobile device 705. Further, if the mobile device 705 is locked, the user must possess a password to unlock the mobile device 705. After the user has unlocked the mobile device 705 and the user has accessed the application, the user must provide an accurate login identifier and corresponding password to access the transaction system 705. Having successfully crossed these stages of security, the user can select a medication and a quantity. The user must further authenticate his/her identity by providing a sample of his/her voice that must match the voice that the user provided when creating the user account. Further, the user's location information, at a time of conducting the transaction, must match the location information at the time of creating the user account.

Figure 8E:
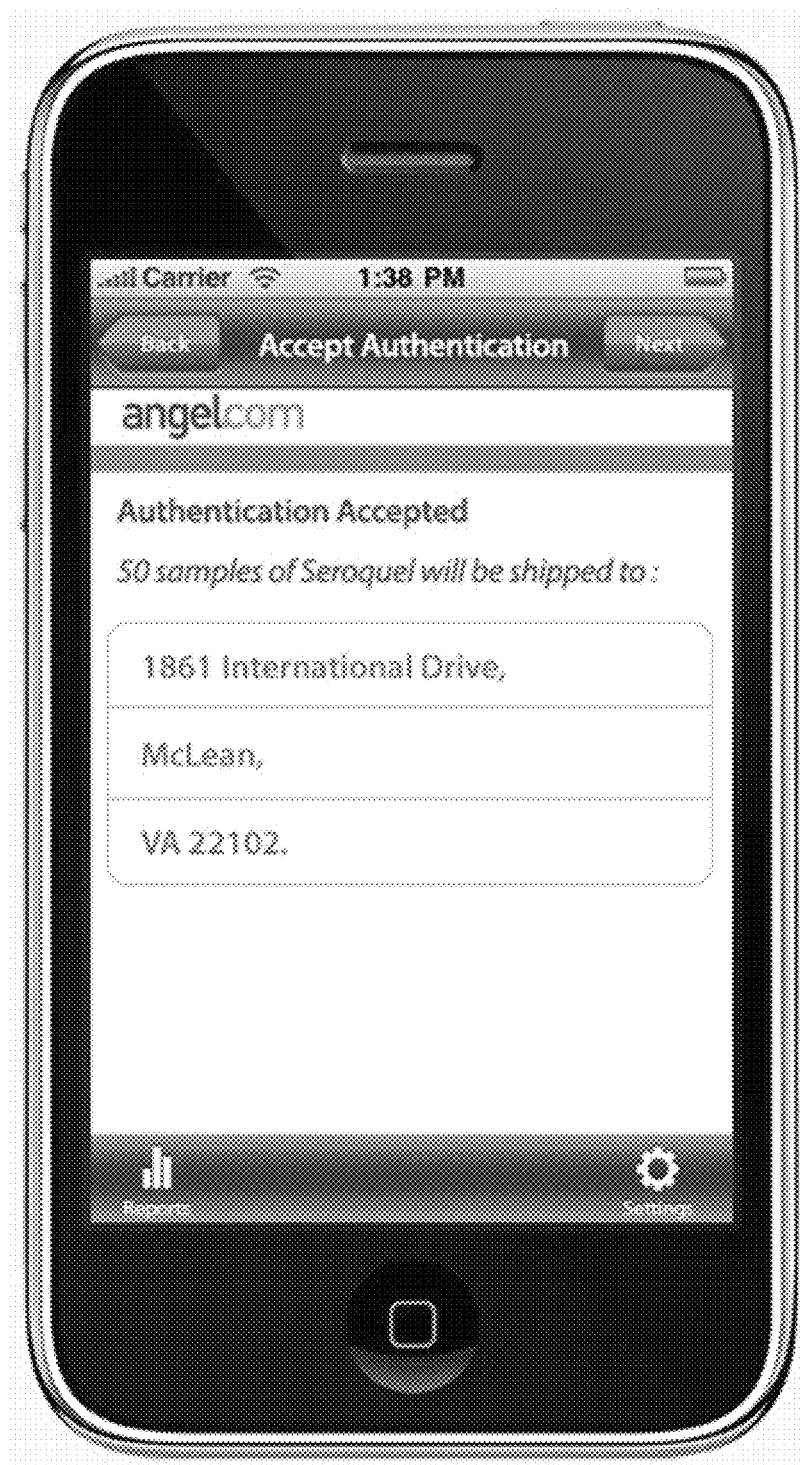
Figure 8F:

Assuming that the user has cleared all of these security layers, the transaction system 710 processes the user's transaction. To do so, the transaction system 710 can transmit the medication names and corresponding quantities to the computer server associated with the source 712. The computer server associated with the source 712 can transmit an acknowledgement to the transaction system 710. The transaction system 710 can transmit the acknowledgement to the mobile device. In some implementations, the application can display the acknowledgement in a fifth user interface (FIG. 8E). For example, in the fifth user interface, the application can display a message indicating that the user has been authenticated, and another message indicating that a selected quantity of the selected medication will be sent to the user's address. In some implementations, the application can further display a sixth user interface (FIG. 8F) in which the application can provide the user with a transaction history of all medical samples that have been procured using the user's account.

Further, in some implementations, after displaying the fifth user interface in the touch screen, the application can transmit a message to the authorized user (for example, to an electronic mail address that the authorized user provided when creating the user account) including the messages displayed in the fifth user interface. In the event that an unauthorized user successfully impersonated the authorized user, the authorized user can disavow the transaction. In some implementations, the transaction system 710 can request the source 712 to withhold sending the medication to the authorized user's address until the authorized user confirms the transaction by responding to the message transmitted after displaying the fifth user interface. In some implementations, the transaction system 710 can request the source 712 to withhold sending the medication for a period of time. If the authorized user does not disavow the transaction within the duration of the period, then the transaction system 710 can request the source 712 to send the medication to the address of the authorized user. Thus, requiring the user to confirm or disavow a processed transaction can be an additional security layer that the user of the mobile device 705 needs to clear to conduct a transaction to procure medical samples.

In some implementations, the transaction system 710 can execute the different security layers in series. For example, the transaction system 710 can wait for an indication from the authentication unit 725 regarding the voice sample before determining if the location coordinates of the mobile device at the time of conducting the transaction match the location coordinates provided by the user when creating the user account. Alternatively, the transaction system 710 can execute the different layers in parallel.

In some implementations, the transaction system 710 can permit only one user to be associated with a user account. For example, the transaction system 710 can receive a voice sample from only one doctor when creating the user account. Thus, the transaction system 710 will authenticate only that doctor's voice in future transactions. Alternatively, the transaction system 710 can associate multiple voices with the same account. This can enable a doctor and the doctor's medical staff to procure medical samples using a single application executing on a single mobile device.

As described previously, the application includes multiple computer program instructions executable by computers. Different mobile devices include different types of computers. The computer program instructions that collectively form the application can be tailored to be executed by different mobile devices. In some implementations, the application can be configured to enable users to order any other regulated items, for example, arms and ammunition.

The disclosed and other examples can be implemented as one or more computer program products, i.e., one or more modules of computer program instructions encoded on a computer readable medium for execution by, or to control the operation of, data processing apparatus. The implementations can include single or distributed processing of algorithms. The computer readable medium can be a machine-readable storage device, a machine-readable storage substrate, a memory device, or a combination of one or more them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A system may encompass all apparatus, devices, and machines for processing data, including by way of example a programmable processor, a computer, or multiple processors or computers. A system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed for execution on one computer or on multiple computers that are located at one site or distributed across multiple sites and interconnected by a communications network.

The processes and logic flows described in this document can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer can include a processor for performing instructions and one or more memory devices for storing instructions and data. Generally, a computer can also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data can include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

While this document may describe many specifics, these should not be construed as limitations on the scope of an invention that is claimed or of what may be claimed, but rather as descriptions of features specific to particular embodiments. For example, a communications channel may include the Web, where a user may interact with an interaction site via a webpage generated dynamically according to the interaction flow. As another example, a communications channel may include a smart phone application, where a user may interact with an interaction site by starting a smart phone application, and the smart phone application then contacts the interaction site and provides a communications interface between the user and the interaction site. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination in some cases can be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Only a few examples and implementations are disclosed. Variations, modifications, and enhancements to the described examples and implementations and other implementations can be made based on what is disclosed.

What is claimed is:

1. A computer-implemented method comprising:
   receiving, at a call handling platform, a first call placed by a first caller to a first calling number;
   computing, by the call handling platform, a first experience score for the first caller based on measuring a first subset of data points corresponding to an interaction between the first caller and an interactive voice response (IVR) module associated with the call handling platform, wherein the first experience score provides a numerical measure of a level of satisfaction of the first caller in interacting with the IVR module during the first call;
   determining, by the call handling platform, to route the first call to a human agent based on the first experience score;
   in response to determining to route the first call to a human agent:
      accessing, by the call handling platform, historical data corresponding to past calls placed by the first caller and received by human agents, wherein the historical data includes information on interactions between the first caller and the human agents during the past calls;
      obtaining, by the call handling platform, agent scores associated with the human agents, wherein the agent scores provide information on a level of performance skills associated with the human agents in interacting with callers; matching, by the call handling platform, the first caller to a first human agent at a first call center based on one or both of the historical data and the agent scores; and
      routing, by the call handling platform, the first call to the first human agent at the first call center;
   enabling a first customer of the call handling platform that is associated with the first calling number to select the first subset of data points from a group of data points available at the call handling platform; and
   enabling the first customer of the call handling platform to configure values for the first subset of data points.

2. The method of claim 1, wherein enabling the first customer of the call handling platform to configure the values for the first subset of data points comprises enabling the first customer to use an Internet-based browser user interface associated with the call handling platform to configure the values for the first subset of data points.

3. The method of claim 1, further comprising:
selecting the first subset of data points from the group consisting of:
a number of no inputs by a caller placing a call to the call handling platform, wherein each no input corresponds to an instance of failure of the caller to respond to a query by the call handling platform,
a number of no matches by a caller placing a call to the call handling platform, wherein each no match corresponds to an instance of the caller providing a response to a query by the call handling platform that does not match a pre-determined response expected by the call handling platform, a number of tasks not completed by a caller placing a call to the call handling platform, wherein each task not completed indicates an instance of the caller failing to complete successfully a task that has been requested by the call handling platform,
a number of zero actions by a caller placing a call to the call handling platform, wherein each zero action corresponds to an instance of the caller providing a pre-configured input indicating an attempt to connect to a human agent irrespective of a query by the call handling platform,
a time to zero out by a caller placing a call to the call handling platform, wherein the time to zero out indicates how quickly the caller attempts to talk to a human agent after the call is connected, and
a wait time of a caller placing a call to the call handling platform, wherein the wait time of the caller indicates how long the caller has to wait before being connected to a human agent.

4. The method of claim 1, wherein determining to route the first call to a human agent based on the first experience score comprises:
accessing a predetermined first threshold that indicates a minimum level of caller satisfaction, wherein the first threshold is configured by a first customer of the call handling platform that is associated with the first calling number;
comparing the first experience score to the first threshold;
determining, by the call handling platform and based on the comparing, that the first experience score for the first caller indicates that the first caller has a lower level of satisfaction than the minimum level of satisfaction; and
routing the first call to the human agent conditioned on determining that the first experience score for the first caller indicates that the first caller has a lower level of satisfaction than the minimum level of satisfaction.

5. The method of claim 1, wherein obtaining the agent scores associated with the human agents comprises:
measuring, by the call handling platform, a first subset of agent skills that are configured by a first customer of the call handling platform that is associated with the first calling number; and
computing, by the call handling platform, an agent score for each human agent trained to answer the first call as a numerical score based on the measuring the first subset of the agent skills.

6. The method of claim 5, wherein measuring the first subset of agent skills comprises:
measuring, by the call handling platform the first subset of agent skills using speech analytics, and wherein the first subset of agent skills are selected from the group consisting of:
courtesy of a human agent in interacting with a caller, which indicates how politely an agent speaks while interacting with a caller,
skill of a human agent in calming an agitated caller, which indicates how well an agent is able to soothe an agitated caller while interacting with the caller,
skill of a human agent in up-selling products to caller, which indicates whether an agent successfully sells a product or service to a caller while interacting with the caller,
skill of a human agent in providing explanations to a caller, which indicates how well an agent is able to answer questions from a caller while interacting with the caller, and
clarity of speech in interacting with a caller, which indicates how clearly an agent speaks while interacting with a caller.

7. The method of claim 1, wherein matching the first caller to a first human agent at a first call center comprises:
determining, by the call handling platform, that no suitable human agent is available based on the historical data corresponding to calls placed by the first caller; and
in response to determining that no suitable human agent is available based on the historical data, identifying, as the first human agent, a human agent having an agent score deemed most compatible with the first call from among the obtained agent scores.

8. The method of claim 1, wherein the historical data includes demographic information associated with the first caller, and wherein matching the first caller to a first human agent at a first call center comprises identifying, by the call handling platform, a human agent who is trained to handle calls from callers with demographic information matching the demographic information associated with the first caller, as the first human agent.

9. The method of claim 1, wherein the historical data includes a speech accent associated with the first caller, and wherein matching the first caller to a first human agent at a first call center comprises identifying, by the call handling platform, a human agent who is trained to handle calls from callers with speech accents matching the speech accent associated with the first caller, as the first human agent.

10. A computer-implemented method comprising:
receiving, at a call handling platform, a first call placed by a first caller to a first calling number;
computing, by the call handling platform, a first experience score for the first caller based on measuring a first subset of data points corresponding to an interaction between the first caller and an interactive voice response (IVR) module associated with the call handling platform, wherein the first experience score provides a numerical measure of a level of satisfaction of the first caller in interacting with the IVR module during the first call;
determining, by the call handling platform, to route the first call to a human agent based on the first experience score;
in response to determining to route the first call to a human agent:
accessing, by the call handling platform, historical data corresponding to past calls placed by the first caller and received by human agents, wherein the historical data includes information on interactions between the first caller and the human agents during the past calls;

obtaining, by the call handling platform, agent scores associated with the human agents, wherein the agent scores provide information on a level of performance skills associated with the human agents in interacting with callers;

matching, by the call handling platform, the first caller to a first human agent at a first call center based on one or both of the historical data and the agent scores; and routing, by the call handling platform, the first call to the first human agent at the first call center, wherein accessing the historical data corresponding to past calls placed by the first caller comprises:

determining, by the call handling platform, a subject matter of the first call;

identifying, by the call handling platform, human agents who are trained to handle calls corresponding to the determined subject matter;

determining, by the call handling platform, whether the first caller had interacted with each of the identified human agents in the past; and obtaining, by the call handling platform, historical data of interactions between the first caller and the identified human agents with whom the first caller had interacted in the past, wherein the historical data includes second experience scores for the first caller, each of the second experience scores being specific to one of the identified human agents with whom the first caller had previously interacted and reflecting an estimated level of satisfaction of the first caller with past interactions with the corresponding one of the identified human agents.

11. The method of claim 10, further comprising:

enabling a first customer of the call handling platform that is associated with the first calling number to configure one or more predetermined keywords, and generating the second experience scores using a speech analysis module that is operable to detect the one or more predetermined keywords in voice speech made by the first caller or a human agent during a call.

12. The method of claim 10, wherein matching the first caller to a first human agent at a first call center comprises identifying the first human agent based on determining, by the call handling platform, that a second experience score indicating that a level of satisfaction of the first caller regarding past interactions with the first human agent is greater than that of the first caller regarding past interactions with other of the identified human agents with whom the first caller had interacted in the past.

13. The method of claim 10, further comprising:

determining, by the call handling platform, that the first human agent is not available to answer the first call based on the first human agent not answering the first call within a predetermined wait period;

identifying a second human agent at a second call center based on identification of a second experience score that indicates that a level of satisfaction of the first caller with past interactions with the second human agent is less than that of the first caller with past interactions with the first human agent but is greater than that of the first caller with past interactions with remaining identified human agents with whom the first caller had interacted in the past; and based on determining that the first human agent is not available to answer the first call, routing, by the call handling platform, the first call to the identified second human agent at the second call center.

14. A system comprising:

a call handling platform that includes a processor and instructions stored in a machine-readable medium that, when executed by the processor, are configured to cause the processor to perform operations comprising:

receiving, at the call handling platform, a first call placed by a first caller to a first calling number;

computing, by the call handling platform, a first experience score for the first caller based on measuring a first subset of data points corresponding to an interaction between the first caller and an interactive voice response (IVR) module associated with the call handling platform, wherein the first experience score provides a numerical measure of a level of satisfaction of the first caller in interacting with the IVR module during the first call;

determining, by the call handling platform, to route the first call to a human agent based on the first experience score;

in response to determining to route the first call to a human agent:

accessing, by the call handling platform, historical data corresponding to past calls placed by the first caller and received by human agents, wherein the historical data includes information on interactions between the first caller and the human agents during the past calls;

obtaining, by the call handling platform, agent scores associated with the human agents, wherein the agent scores provide information on a level of performance skills associated with the human agents in interacting with callers;

matching, by the call handling platform, the first caller to a first human agent at a first call center based on one or both of the historical data and the agent scores; and routing, by the call handling platform, the first call to the first human agent at the first call center, wherein accessing the historical data corresponding to past calls placed by the first caller comprises:

determining, by the call handling platform, a subject matter of the first call;

identifying, by the call handling platform, human agents who are trained to handle calls corresponding to the determined subject matter;

determining, by the call handling platform, whether the first caller had interacted with each of the identified human agents in the past; and obtaining, by the call handling platform, historical data of interactions between the first caller and the identified human agents with whom the first caller had interacted in the past, wherein the historical data includes second experience scores for the first caller, each of the second experience scores being specific to one of the identified human agents with whom the first caller had previously interacted and reflecting an estimated level of satisfaction of the first caller with past interactions with the corresponding one of the identified human agents.

15. The system of claim 14, wherein determining to route the first call to a human agent based on the first experience score comprises:

accessing a predetermined first threshold that indicates a minimum level of caller satisfaction, wherein the first threshold is configured by a first customer of the call handling platform that is associated with the first calling number;

comparing the first experience score to the first threshold;

determining, by the call handling platform and based on the comparing, that the first experience score for the first caller indicates that the first caller has a lower level of satisfaction than the minimum level of satisfaction; and routing the first call to the human agent conditioned on determining that the first experience score for the first caller indicates that the first caller has a lower level of satisfaction than the minimum level of satisfaction.

16. The system of claim 14, wherein obtaining the agent scores associated with the human agents comprises:

measuring, by the call handling platform, a first subset of agent skills that are configured by a first customer of the call handling platform that is associated with the first calling number; and computing, by the call handling platform, an agent score for each human agent trained to answer the first call as a numerical score based on the measuring the first subset of the agent skills.

17. The system of claim 14, wherein the instructions are configured to cause the processor to perform operations further comprising:

enabling a first customer of the call handling platform that is associated with the first calling number to configure one or more predetermined keywords, and generating the second experience scores using a speech analysis module that is operable to detect the one or more predetermined keywords in voice speech made by the first caller or a human agent during a call.

18. The system of claim 14, wherein matching the first caller to a first human agent at a first call center comprises identifying the first human agent based on identification, by the call handling platform, of a second experience score that indicates that a level of satisfaction of the first caller with past interactions with the first human agent is greater than that of the first caller with past interactions with other of the identified human agents with whom the first caller had interacted in the past.

* * * * *